(12) United States Patent
Zelder et al.

(10) Patent No.: US 8,048,651 B2
(45) Date of Patent: Nov. 1, 2011

(54) **METHODS FOR THE PREPARATION OF LYSINE BY FERMENTATION OF *CORYNEBACTERIUM GLUTAMICUM***

(75) Inventors: Oskar Zelder, Speyer (DE); Corinna Klopprogge, Mannheim (DE); Hartwig Schroder, Nussloch (DE); Stefan Haefner, Ludwigshafen (DE); Burkhard Kröger, Limburgerhof (DE); Patrick Kiefer, Zurich (DE); Elmar Heinzle, Saarbrücken (DE); Christoph Wittmann, Saarbrücken (DE)

(73) Assignee: BASF SE (DE)

( * ) Notice: Subject to any disclaimer, the term of this patent is extended or adjusted under 35 U.S.C. 154(b) by 0 days.

(21) Appl. No.: 12/533,677

(22) Filed: Jul. 31, 2009

(65) Prior Publication Data

US 2010/0015674 A1 Jan. 21, 2010

Related U.S. Application Data

(62) Division of application No. 12/021,081, filed on Jan. 28, 2008, now abandoned, which is a division of application No. 10/579,690, filed as application No. PCT/IB2004/004429 on Dec. 17, 2004, now abandoned.

(30) Foreign Application Priority Data

Dec. 18, 2003 (WO) .................. PCT/IB2003/006456

(51) Int. Cl.
*C12P 13/06* (2006.01)
*C12P 13/08* (2006.01)
*C12P 13/10* (2006.01)
*C12P 13/12* (2006.01)
*C12P 23/00* (2006.01)
*C12N 9/16* (2006.01)
*C12N 15/70* (2006.01)
*C12N 1/20* (2006.01)
*C12N 15/74* (2006.01)
*C07H 21/04* (2006.01)

(52) U.S. Cl. ........ 435/115; 435/113; 435/114; 435/116; 435/69.1; 435/196; 435/252.32; 435/471; 536/23.2

(58) Field of Classification Search .................. None
See application file for complete search history.

(56) References Cited

U.S. PATENT DOCUMENTS

2003/0044943 A1* 3/2003 Farwick et al. ............... 435/106
2009/0158452 A1* 6/2009 Johnson et al. ............... 800/260

FOREIGN PATENT DOCUMENTS

| EP | 1108790 A2 | 6/2001 |
| WO | WO-01/00844 A2 | 1/2001 |
| WO | WO-01/07626 A2 | 2/2001 |

OTHER PUBLICATIONS

Kiefer et al. J Industrial Microbiol & Biotechnology 2002, 28:338-343.*
Dominguez, H., et al., "Carbon-flux distribution in the central metabolic pathways of *Corynebacterium glutamicum* during growth on fructose", Eur. J. Biochem., 1998, vol. 254, pp. 96-102.
Kiefer, P., et al., "Influence of glucose, fructose and sucrose as carbon sources on kinetics and stoichiometry of lysine production by *Corynebacterium glutamicum*", Journal of Industrial Microbiology & Biotechnology, 2002, vol. 28, pp. 338-343.
Kiefer, P., et al., "Comparative metabolic flux analysis of lysine-producing *Corynebacterium glutamicum* cultured on glucose or fructose", Applied and Environmental Microbiology, 2004, vol. 70, No. 1, pp. 229-239.
Marx, A., et al., "Metabolic phenotype of phosphoglucose isomerase mutants of *Corynebacterium glutamicum*", Journal of Biotechnology, 2003, vol. 104, pp. 185-197.
Ohnishi, J., et al., "A novel methodology employing *Corynebacterium glutamicum* genome information to generate a new L-lysine-producing mutant", Appl. Microbiol. Biotechnol., 2002, vol. 58, No. 2, pp. 217-223.
Pfefferle, W., et al., "Biotechnological manufacture of lysine", Advances in Biochemical Engineering/Biotechnology, 2003, vol. 79, pp. 59-112.
Rittman, D., et al,, "Fructose-1,6-bisphosphatase from *Corynebacterium glutamicum*: expression and deletion of the fbp gene and biochemical characterization of the enzyme", Arch. Microbio., 2003, vol. 180, pp. 285-292.
Sahm, H., et al., "Pathway analysis and metabolic engineering in *Corynebacterium glutamicum*", Biol. Chem., 2000, vol. 381, pp. 899-910.
Wittmann, C., et al., "Genealogy profiling through strain improvement by using metabolic network analysis: metabolic flux genealogy of several generations of lysine-producing *corynebacteria*", Applied and Environmental Microbiology, 2002, vol. 68, No. 12, pp. 5843-5859.
Eikmanns et al., "Molecular Aspects of Lysine, Threonine, and Isoleucine Biosynthesis in *Corynebacterium glutamicum*", Kluwer Academic Publishers, 1993, vol. 64, pp. 145-163.
Eggeling et al., "$_L$-Glutamate and $_L$-Lysine: Traditional Products with Impetuous Developments", Appl. Microbiol Biotechnol, 1999, vol. 52, pp. 146-153.

* cited by examiner

*Primary Examiner* — Anand Desai
*Assistant Examiner* — Iqbal H Chowdhury
(74) *Attorney, Agent, or Firm* — Connolly Bove Lodge & Hutz, LLP

(57) ABSTRACT

The present invention features methods of increasing the production of a fine chemical, e.g., lysine from a microorganism, e.g., *Corynebacterium* by way of deregulating an enzyme encoding gene, i.e., fructose-1,6-bisphosphatase. In a preferred embodiment, the invention provides methods of increasing the production of lysine in *Corynebacterium glutamicum* by way of increasing the expression of fructose-1,6-bisphosphatase activity. The invention also provides a novel process for the production of lysine by way of regulating carbon flux towards oxaloacetate (OAA). In a preferred embodiment, the invention provides methods for the production of lysine by way of utilizing fructose or sucrose as a carbon source.

13 Claims, 6 Drawing Sheets

SEQUENCE LISTING

<160> NUMBER OF SEQ ID NOS: 24

<210> SEQ ID NO 1
<211> LENGTH: 1070
<212> TYPE: DNA
<213> ORGANISM: Corynebacterium glutamicum
<220> FEATURE:
<221> NAME/KEY: CDS
<222> LOCATION: (22)...(1029)

<400> SEQUENCE: 1

```
gtgcccagg aggcccttca g atg aac cta aag aac ccc gaa acg cca gac        51
                      Met Asn Leu Lys Asn Pro Glu Thr Pro Asp
                       1               5                  10 cgt aac ctt gct atg gag ctg gtg cga gtt acg gaa gca gct gca ctg        99
Arg Asn Leu Ala Met Glu Leu Val Arg Val Thr Glu Ala Ala Ala Leu
                15                  20                  25 gct tct gga cgt tgg gtt gga cgt ggc atg aag aat gaa ggc gac ggt       147
Ala Ser Gly Arg Trp Val Gly Arg Gly Met Lys Asn Glu Gly Asp Gly
            30                  35                  40 gcc gct gtt gac gcc atg cgc cag ctc atc aac tca gtg acc atg aag       195
Ala Ala Val Asp Ala Met Arg Gln Leu Ile Asn Ser Val Thr Met Lys
        45                  50                  55 ggc gtc gtt gtt atc ggc gag ggc gaa aaa gac gaa gct cca atg ctg       243
Gly Val Val Val Ile Gly Glu Gly Glu Lys Asp Glu Ala Pro Met Leu
    60                  65                  70 tac aac ggc gaa gag gtc gga acc ggc ttt gga cct gag gtt gat atc       291
Tyr Asn Gly Glu Glu Val Gly Thr Gly Phe Gly Pro Glu Val Asp Ile
75                  80                  85                  90 gca gtt gac cca gtt gac ggc acc acc ctg atg gct gag ggt cgc ccc       339
Ala Val Asp Pro Val Asp Gly Thr Thr Leu Met Ala Glu Gly Arg Pro
                95                 100                 105 aac gca att tcc att ctc gca gct gca gag cgt ggc acc atg tac gat       387
Asn Ala Ile Ser Ile Leu Ala Ala Ala Glu Arg Gly Thr Met Tyr Asp
            110                 115                 120 cca tcc tcc gtc ttc tac atg aag aag atc gcc gtg gga cct gag gcc       435
Pro Ser Ser Val Phe Tyr Met Lys Lys Ile Ala Val Gly Pro Glu Ala
```

```
                     125                 130                     135
gca ggc aag atc gac atc gaa gct cca gtt gcc cac aac atc aac gcg      483
Ala Gly Lys Ile Asp Ile Glu Ala Pro Val Ala His Asn Ile Asn Ala
    140                 145                     150 gtg gca aag tcc aag gga atc aac cct tcc gac gtc acc gtt gtc gtg      531
Val Ala Lys Ser Lys Gly Ile Asn Pro Ser Asp Val Thr Val Val Val
155                 160                     165                 170 ctt gac cgt cct cgc cac atc gaa ctg atc gca gac att cgt cgt gca      579
Leu Asp Arg Pro Arg His Ile Glu Leu Ile Ala Asp Ile Arg Arg Ala
                175                     180                 185 ggc gca aag gtt cgt ctc atc tcc gac ggc gac gtt gca ggt gca gtt      627
Gly Ala Lys Val Arg Leu Ile Ser Asp Gly Asp Val Ala Gly Ala Val
            190                     195                 200 gca gca gct cag gat tcc aac tcc gtg gac atc atg atg ggc acc ggc      675
Ala Ala Ala Gln Asp Ser Asn Ser Val Asp Ile Met Met Gly Thr Gly
        205                     210                 215 gga acc cca gaa ggc atc atc act gcg tgc gcc atg aag tgc atg ggt      723
Gly Thr Pro Glu Gly Ile Ile Thr Ala Cys Ala Met Lys Cys Met Gly
220                     225                 230 ggc gaa atc cag ggc atc ctg gcc cca atg aac gat ttc gag cgc cag      771
Gly Glu Ile Gln Gly Ile Leu Ala Pro Met Asn Asp Phe Glu Arg Gln
235                 240                     245                 250 aag gca cac gac gct ggt ctg gtt ctt gat cag gtt ctg cac acc aac      819
Lys Ala His Asp Ala Gly Leu Val Leu Asp Gln Val Leu His Thr Asn
                255                     260                 265 gat ctg gtg agc tcc gac aac tgc tac ttc gtg gca acc ggt gtg acc      867
Asp Leu Val Ser Ser Asp Asn Cys Tyr Phe Val Ala Thr Gly Val Thr
            270                     275                 280 aac ggt gac atg ctc cgt ggc gtt tcc tac cgc gca aac ggc gca acc      915
Asn Gly Asp Met Leu Arg Gly Val Ser Tyr Arg Ala Asn Gly Ala Thr
        285                     290                 295 acc cgt tcc ctg gtt atg cgc gca aag tca ggc acc atc cgc cac atc      963
Thr Arg Ser Leu Val Met Arg Ala Lys Ser Gly Thr Ile Arg His Ile
300                     305                 310 gag tct gtc cac cag ctg tcc aag ctg cag gaa tac tcc gtg gtt gac     1011
Glu Ser Val His Gln Leu Ser Lys Leu Gln Glu Tyr Ser Val Val Asp
315                 320                     325                 330 tac acc acc gcg acc taa gagctcttag ttcgaaaaac cgccggccat            1059
Tyr Thr Thr Ala Thr *
                335 tgtggtcggc g                                                        1070

<210> SEQ ID NO 2
<211> LENGTH: 335
<212> TYPE: PRT
<213> ORGANISM: Corynebacterium glutamicum

<400> SEQUENCE: 2

Met Asn Leu Lys Asn Pro Glu Thr Pro Asp Arg Asn Leu Ala Met Glu
1               5                   10                  15

Leu Val Arg Val Thr Glu Ala Ala Leu Ala Ser Gly Arg Trp Val
            20                  25                  30

Gly Arg Gly Met Lys Asn Glu Gly Asp Gly Ala Ala Val Asp Ala Met
        35                  40                  45

Arg Gln Leu Ile Asn Ser Val Thr Met Lys Gly Val Val Val Ile Gly
    50                  55                  60

Glu Gly Glu Lys Asp Glu Ala Pro Met Leu Tyr Asn Gly Glu Glu Val
65                  70                  75                  80

Gly Thr Gly Phe Gly Pro Glu Val Asp Ile Ala Val Asp Pro Val Asp
```

```
                            85                  90                  95
Gly Thr Thr Leu Met Ala Glu Gly Arg Pro Asn Ala Ile Ser Ile Leu
            100                 105                 110
Ala Ala Ala Glu Arg Gly Thr Met Tyr Asp Pro Ser Ser Val Phe Tyr
        115                 120                 125
Met Lys Lys Ile Ala Val Gly Pro Glu Ala Gly Lys Ile Asp Ile
    130                 135                 140
Glu Ala Pro Val Ala His Asn Ile Asn Ala Val Ala Lys Ser Lys Gly
145                 150                 155                 160
Ile Asn Pro Ser Asp Val Thr Val Val Leu Asp Arg Pro Arg His
                165                 170                 175
Ile Glu Leu Ile Ala Asp Ile Arg Arg Ala Gly Ala Lys Val Arg Leu
            180                 185                 190
Ile Ser Asp Gly Asp Val Ala Gly Val Ala Ala Gln Asp Ser
        195                 200                 205
Asn Ser Val Asp Ile Met Met Gly Thr Gly Thr Pro Glu Gly Ile
    210                 215                 220
Ile Thr Ala Cys Ala Met Lys Cys Met Gly Glu Ile Gln Gly Ile
225                 230                 235                 240
Leu Ala Pro Met Asn Asp Phe Glu Arg Gln Lys Ala His Asp Ala Gly
                245                 250                 255
Leu Val Leu Asp Gln Val Leu His Thr Asn Asp Leu Val Ser Ser Asp
            260                 265                 270
Asn Cys Tyr Phe Val Ala Thr Gly Val Thr Asn Gly Asp Met Leu Arg
        275                 280                 285
Gly Val Ser Tyr Arg Ala Asn Gly Ala Thr Thr Arg Ser Leu Val Met
    290                 295                 300
Arg Ala Lys Ser Gly Thr Ile Arg His Ile Glu Ser Val His Gln Leu
305                 310                 315                 320
Ser Lys Leu Gln Glu Tyr Ser Val Asp Tyr Thr Thr Ala Thr
                325                 330                 335

<210> SEQ ID NO 3
<211> LENGTH: 35
<212> TYPE: DNA
<213> ORGANISM: Artificial Sequence
<220> FEATURE:
<223> OTHER INFORMATION: Synthetic construct

<400> SEQUENCE: 3
gagagagaga cgcgtcccag tggctgagac gcatc                              35

<210> SEQ ID NO 4
<211> LENGTH: 34
<212> TYPE: DNA
<213> ORGANISM: Artificial Sequence
<220> FEATURE:
<223> OTHER INFORMATION: Synthetic construct

<400> SEQUENCE: 4
ctctctctgt cgacgaattc aatcttacgg cctg                               34

<210> SEQ ID NO 5
<211> LENGTH: 4323
<212> TYPE: DNA
<213> ORGANISM: Corynebacterium glutamicum

<400> SEQUENCE: 5
tcgagaggcc tgacgtcggg cccggtacca cgcgtcatat gactagttcg gacctaggga    60
```

-continued

```
tatcgtcgac atcgatgctc ttctgcgtta attaacaatt gggatcctct agacccggga    120
tttaaatcgc tagcgggctg ctaaaggaag cggaacacgt agaaagccag tccgcagaaa    180
cggtgctgac cccggatgaa tgtcagctac tgggctatct ggacaaggga aaacgcaagc    240
gcaaagagaa agcaggtagc ttgcagtggg cttacatggc gatagctaga ctgggcggtt    300
ttatggacag caagcgaacc ggaattgcca gctggggcgc cctctggtaa ggttgggaag    360
ccctgcaaag taaactggat ggcttttcttg ccgccaagga tctgatggcg cagggatca    420 agatctgatc aagagacagg atgaggatcg tttcgcatga ttgaacaaga tggattgcac    480
gcaggttctc cggccgcttg ggtggagagg ctattcggct atgactgggc acaacagaca    540
atcggctgct ctgatgccgc cgtgttccgg ctgtcagcgc aggggcgccc ggttcttttt    600
gtcaagaccg acctgtccgg tgccctgaat gaactgcagg acgaggcagc gcggctatcg    660
tggctggcca cgacgggcgt tccttgcgca gctgtgctcg acgttgtcac tgaagcggga    720
agggactggc tgctattggg cgaagtgccg gggcaggatc tcctgtcatc tcaccttgct    780
cctgccgaga agtatccat catggctgat gcaatgcggc ggctgcatac gcttgatccg    840
gctacctgcc cattcgacca ccaagcgaaa catcgcatcg agcgagcacg tactcggatg    900
gaagccggtc ttgtcgatca ggatgatctg gacgaagagc atcaggggct cgcgccagcc    960
gaactgttcg ccaggctcaa ggcgcgcatg cccgacggcg aggatctcgt cgtgacccat    1020
ggcgatgcct gcttgccgaa tatcatggtg gaaaatggcc gcttttctgg attcatcgac    1080
tgtggccggc tgggtgtggc ggaccgctat caggacatag cgttggctac ccgtgatatt    1140
gctgaagagc ttggcggcga atgggctgac cgcttcctcg tgctttacgg tatcgccgct    1200
cccgattcgc agcgcatcgc cttctatcgc cttcttgacg agttcttctg agcgggactc    1260
tggggttcga atgaccgac caagcgacgc ccaacctgcc atcacgagat ttcgattcca    1320
ccgccgcctt ctatgaaagg ttgggcttcg gaatcgtttt ccgggacgcc ggctggatga    1380
tcctccagcg cggggatctc atgctggagt tcttcgccca cgctagcggc gcgccggccg    1440
gcccggtgtg aaataccgca cagatgcgta aggagaaaat accgcatcag cgctcttcc    1500 gcttcctcgc tcactgactc gctgcgctcg tcgttcggc tgcggcgagc ggtatcagct    1560
cactcaaagg cggtaatacg gttatccaca gaatcagggg ataacgcagg aaagaacatg    1620
tgagcaaaag gccagcaaaa ggccaggaac cgtaaaaagg ccgcgttgct ggcgtttttc    1680
cataggctcc gccccctga cgagcatcac aaaaatcgac gctcaagtca gaggtggcga    1740
aacccgacag gactataaag ataccaggcg tttccccctg gaagctccct cgtgcgctct    1800
cctgttccga ccctgccgct taccggatac ctgtccgcct ttctcccttc gggaagcgtg    1860
gcgctttctc atagctcacg ctgtaggtat ctcagttcgg tgtaggtcgt tcgctccaag    1920
ctgggctgtg tgcacgaacc ccccgttcag cccgaccgct gcgccttatc cggtaactat    1980
cgtcttgagt ccaacccggt aagacacgac ttatcgccac tggcagcagc cactggtaac    2040
aggattagca gagcgaggta tgtaggcggt gctacagagt tcttgaagtg gtggcctaac    2100
tacggctaca ctagaaggac agtatttggt atctgcgctc tgctgaagcc agttaccttc    2160
ggaaaaagag ttggtagctc ttgatccggc aaacaaacca ccgctggtag cggtggtttt    2220
tttgtttgca agcagcagat tacgcgcaga aaaaaggat ctcaagaaga tcctttgatc    2280
ttttctacgg ggtctgacgc tcagtggaac gaaaactcac gttaagggat tttggtcatg    2340
agattatcaa aaaggatctt cacctagatc cttttaaagg ccgccgcgg ccgccatcgg    2400 cattttcttt tgcgttttta tttgttaact gttaattgtc cttgttcaag gatgctgtct    2460
```

```
ttgacaacag atgttttctt gcctttgatg ttcagcagga agctcggcgc aaacgttgat    2520
tgtttgtctg cgtagaatcc tctgtttgtc atatagcttg taatcacgac attgtttcct    2580
ttcgcttgag gtacagcgaa gtgtgagtaa gtaaaggtta catcgttagg atcaagatcc    2640
atttttaaca caaggccagt tttgttcagc ggcttgtatg ggccagttaa agaattagaa    2700
acataaccaa gcatgtaaat atcgttagac gtaatgccgt caatcgtcat ttttgatccg    2760
cgggagtcag tgaacaggta ccatttgccg ttcattttaa agacgttcgc gcgttcaatt    2820
tcatctgtta ctgtgttaga tgcaatcagc ggtttcatca cttttttcag tgtgtaatca    2880
tcgtttagct caatcatacc gagagcgccg tttgctaact cagccgtgcg tttttttatcg   2940 ctttgcagaa gttttgact tcttgacgg aagaatgatg tgcttttgcc atagtatgct     3000
ttgttaaata aagattcttc gccttggtag ccatcttcag ttccagtgtt tgcttcaaat    3060
actaagtatt tgtggccttt atcttctacg tagtgaggat ctctcagcgt atggttgtcg    3120
cctgagctgt agttgcctc atcgatgaac tgctgtacat tttgatacgt ttttccgtca     3180
ccgtcaaaga ttgatttata atcctctaca ccgttgatgt tcaaagagct gtctgatgct    3240
gatacgttaa cttgtgcagt tgtcagtgtt tgtttgccgt aatgtttacc ggagaaatca    3300
gtgtagaata aacggatttt tccgtcagat gtaaatgtgg ctgaacctga ccattcttgt    3360
gtttggtctt ttaggataga atcatttgca tcgaatttgt cgctgtcttt aaagacgcgg    3420
ccagcgtttt tccagctgtc aatagaagtt tcgccgactt tttgatagaa catgtaaatc    3480
gatgtgtcat ccgcattttt aggatctccg gctaatgcaa agacgatgtg gtagccgtga    3540
tagtttgcga cagtgccgtc agcgttttgt aatggccagc tgtcccaaac gtccaggcct    3600
tttgcagaag agatattttt aattgtggac gaatcaaatt cagaaacttg atatttttca    3660 ttttttttgct gttcagggat ttgcagcata tcatggcgtg taatatggga aatgccgtat   3720
gtttccttat atggctttg gttcgttct ttcgcaaacg cttgagttgc gcctcctgcc      3780
agcagtgcgg tagtaaaggt taatactgtt gcttgttttg caaactttt gatgttcatc    3840 gttcatgtct cctttttat gtactgtgtt agcggtctgc ttcttccagc cctcctgttt    3900
gaagatggca agttagttac gcacaataaa aaaagaccta aaatatgtaa ggggtgacgc    3960
caaagtatac actttgccct ttacacattt taggtcttgc ctgctttatc agtaacaaac    4020
ccgcgcgatt tacttttcga cctcattcta ttagactctc gtttggattg caactggtct    4080
attttcctct tttgtttgat agaaaatcat aaaaggattt gcagactacg ggcctaaaga    4140 actaaaaat ctatctgttt cttttcattc tctgtatttt ttatagtttc tgttgcatgg     4200
gcataaagtt gccttttaa tcacaattca gaaatatca taatatctca tttcactaaa      4260
taatagtgaa cggcaggtat atgtgatggg ttaaaaagga tcggcggccg ctcgatttaa    4320
atc                                                                  4323
```

<210> SEQ ID NO 6
<211> LENGTH: 5860
<212> TYPE: DNA
<213> ORGANISM: Corynebacterium glutamicum

<400> SEQUENCE: 6

```
cccggtacca cgcgtcccag tggctgagac gcatccgcta aagccccagg aaccctgtgc     60
agaaagaaaa cactcctctg gctaggtaga cacagtttat aaaggtagag ttgagcgggt    120
aactgtcagc acgtagatcg aaaggtgcac aaaggtggcc ctggtcgtac agaaatatgg    180
cggttcctcg cttgagagtg cggaacgcat tagaaacgtc gctgaacgga tcgttgccac    240
```

```
caagaaggct ggaaatgatg tcgtggttgt ctgctccgca atgggagaca ccacggatga   300
acttctagaa cttgcagcgg cagtgaatcc cgttccgcca gctcgtgaaa tggatatgct   360
cctgactgct ggtgagcgta tttctaacgc tctcgtcgcc atggctattg agtcccttgg   420
cgcagaagcc caatctttca cgggctctca ggctggtgtg ctcaccaccg agcgccacgg   480
aaacgcacgc attgttgatg tcactccagg tcgtgtgcgt gaagcactcg atgagggcaa   540
gatctgcatt gttgctggtt ccagggtgt taataaagaa acccgcgatg tcaccacgtt   600
gggtcgtggt ggttctgaca ccactgcagt tgcgttggca gctgctttga acgctgatgt   660
gtgtgagatt tactcggacg ttgacggtgt gtataccgct gacccgcgca tcgttcctaa   720
tgcacagaag ctggaaaagc tcagcttcga agaaatgctg gaacttgctg ctgttggctc   780
caagattttg gtgctgcgca gtgttgaata cgctcgtgca ttcaatgtgc cacttcgcgt   840
acgctcgtct tatagtaatg atcccggcac tttgattgcc ggctctatgg aggatattcc   900
tgtggaagaa gcagtcctta ccggtgtcgc aaccgacaag tccgaagcca agtaaccgt   960 tctgggtatt tccgataagc caggcgaggc tgcgaaggtt ttccgtgcgt tggctgatgc   1020
agaaatcaac attgacatgg ttctgcagaa cgtctcttct gtagaagacg gcaccaccga   1080
catcaccttc acctgccctc gttccgacgg ccgccgcgcg atggagatct gaagaagct   1140 tcaggttcag ggcaactgga ccaatgtgct ttacgacgac caggtcggca aagtctccct   1200
cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
cgaagacgaa gccgtcgttt atgcaggcac cggacgctaa agttttaaag gagtagtttt   1440
acaatgacca ccatcgcagt tgttggtgca accggccagg tcggccaggt tatgcgcacc   1500
cttttggaag agcgcaattt cccagctgac actgttcgtt tctttgcttc cccacgttcc   1560
gcaggccgta agattgaatt cgtcgacatc gatgctcttc tgcgttaatt aacaattggg   1620
atcctctaga cccgggattt aaatcgctag cgggctgcta aggaagcgg aacacgtaga   1680 aagccagtcc gcagaaacgg tgctgacccc ggatgaatgt cagctactgg gctatctgga   1740
caagggaaaa cgcaagcgca aagagaaagc aggtagcttg cagtgggctt acatggcgat   1800
agctagactg ggcggttta tggacagcaa gcgaaccgga attgccagct ggggcgccct   1860
ctggtaaggt tgggaagccc tgcaaagtaa actggatggc tttcttgccg ccaaggatct   1920
gatggcgcag gggatcaaga tctgatcaag agacaggatg aggatcgttt cgcatgattg   1980
aacaagatgg attgcacgca ggttctccgg ccgcttgggt ggagaggcta ttcggctatg   2040
actgggcaca acagacaatc ggctgctctg atgccgccgt gttccggctg tcagcgcagg   2100
ggcgcccggt tcttttttgtc aagaccgacc tgtccggtgc cctgaatgaa ctgcaggacg   2160
aggcagcgcg gctatcgtgg ctggccacga cgggcgttcc ttgcgcagct gtgctcgacg   2220
ttgtcactga agcgggaagg gactggctgc tattgggcga agtgccgggg caggatctcc   2280
tgtcatctca ccttgctcct gccgagaaag tatccatcat ggctgatgca atgcggcggc   2340
tgcatacgct tgatccggct acctgcccat tcgaccacca agcgaaacat cgcatcgagc   2400
gagcacgtac tcggatggaa gccggtcttg tcgatcagga tgatctggac gaagagcatc   2460
aggggctcgc gccagccgaa ctgttcgcca ggctcaaggc gcgcatgccc gacggcgagg   2520
atctcgtcgt gacccatggc gatgcctgct tgccgaatat catggtggaa aatggccgct   2580
tttctggatt catcgactgt ggccggctgg gtgtggcgga ccgctatcag gacatagcgt   2640
```

```
tggctacccg tgatattgct gaagagcttg gcggcgaatg ggctgaccgc ttcctcgtgc   2700
tttacggtat cgccgctccc gattcgcagc gcatcgcctt ctatcgcctt cttgacgagt   2760
tcttctgagc gggactctgg ggttcgaaat gaccgaccaa gcgacgccca acctgccatc   2820
acgagatttc gattccaccg ccgccttcta tgaaaggttg ggcttcggaa tcgttttccg   2880
ggacgccggc tggatgatcc tccagcgcgg ggatctcatg ctggagttct tcgcccacgc   2940
tagcggcgcg ccggccggcc cggtgtgaaa taccgcacag atgcgtaagg agaaaatacc   3000
gcatcaggcg ctcttccgct tcctcgctca ctgactcgct gcgctcggtc gttcggctgc   3060
ggcgagcggt atcagctcac tcaaaggcgg taatacggtt atccacagaa tcagggggata   3120 acgcaggaaa gaacatgtga gcaaaaggcc agcaaaaggc caggaaccgt aaaaaggccg   3180
cgttgctggc gtttttccat aggctccgcc cccctgacga gcatcacaaa aatcgacgct   3240
caagtcagag gtggcgaaac ccgacaggac tataaagata ccaggcgttt ccccctggaa   3300
gctccctcgt gcgctctcct gttccgaccc tgccgcttac cggatacctg tccgcctttc   3360
tcccttcggg aagcgtggcg ctttctcata gctcacgctg taggtatctc agttcggtgt   3420
aggtcgttcg ctccaagctg ggctgtgtgc acgaaccccc cgttcagccc gaccgctgcg   3480
ccttatccgg taactatcgt cttgagtcca acccggtaag acacgactta tcgccactgg   3540
cagcagccac tggtaacagg attagcagag cgaggtatgt aggcggtgct acagagttct   3600
tgaagtggtg gcctaactac ggctacacta aaggacagt atttggtatc tgcgctctgc   3660
tgaagccagt taccttcgga aaaagagttg gtagctcttg atccggcaaa caaaccaccg   3720
ctggtagcgg tggttttttt gtttgcaagc agcagattac gcgcagaaaa aaaggatctc   3780
aagaagatcc tttgatcttt tctacggggt ctgacgctca gtggaacgaa aactcacgtt   3840
aagggatttt ggtcatgaga ttatcaaaaa ggatcttcac ctagatcctt ttaaaggccg   3900
gccgcggccg ccatcggcat tttcttttgc gttttatttt gttaactgtt aattgtcctt   3960
gttcaaggat gctgtctttg acaacagatg ttttcttgcc tttgatgttc agcaggaagc   4020
tcggcgcaaa cgttgattgt ttgtctgcgt agaatcctct gtttgtcata tagcttgtaa   4080
tcacgacatt gtttcctttc gcttgaggta cagcgaagtg tgagtaagta aaggttacat   4140
cgttaggatc aagatccatt tttaacacaa ggccagtttt gttcagcggc ttgtatgggc   4200
cagttaaaga attagaaaca taaccaagca tgtaaatatc gttagacgta atgccgtcaa   4260
tcgtcatttt tgatccgcgg gagtcagtga acaggtacca tttgccgttc attttaaaga   4320
cgttcgcgcg ttcaatttca tctgttactg tgttagatgc aatcagcggt ttcatcactt   4380
ttttcagtgt gtaatcatcg tttagctcaa tcataccgag agcgccgttt gctaactcag   4440
ccgtgcgttt tttatcgctt tgcagaagtt tttgactttc ttgacggaag aatgatgtgc   4500
ttttgccata gtatgctttg ttaaataaag attcttcgcc ttggtagcca tcttcagttc   4560
cagtgtttgc ttcaaatact aagtatttgt ggcctttatc ttctacgtag tgaggatctc   4620
tcagcgtatg gttgtcgcct gagctgtagt tgccttcatc gatgaactgc tgtacatttt   4680
gatacgtttt tccgtcaccg tcaaagattg atttataatc ctctacaccg ttgatgttca   4740
aagagctgtc tgatgctgat acgttaactt gtgcagttgt cagtgtttgt ttgccgtaat   4800
gtttaccgga gaaatcagtg tagaataaac ggattttcc gtcagatgta aatgtggctg   4860
aacctgacca ttcttgtgtt tggtctttta ggatagaatc atttgcatcg aatttgtcgc   4920
tgtctttaaa gacgcggcca gcgttttcc agctgtcaat agaagtttcg ccgactttt   4980 gatagaacat gtaaatcgat gtgtcatccg cattttagg atctccggct aatgcaaaga   5040
```

```
cgatgtggta gccgtgatag tttgcgacag tgccgtcagc gttttgtaat ggccagctgt    5100
cccaaacgtc caggccttt  gcagaagaga tatttttaat tgtggacgaa tcaaattcag    5160
aaacttgata ttttcatt   ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttgat  gttcatcgtt catgtctcct ttttatgta  ctgtgttagc ggtctgcttc    5400
ttccagccct cctgtttgaa gatggcaagt tagttacgca caataaaaaa agacctaaaa    5460
tatgtaaggg gtgacgccaa agtatacact ttgcccttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
tagtttctgt tgcatgggca taaagttgcc tttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                          5860
```

<210> SEQ ID NO 7
<211> LENGTH: 38
<212> TYPE: DNA
<213> ORGANISM: Artificial Sequence
<220> FEATURE:
<223> OTHER INFORMATION: Synthetic construct

<400> SEQUENCE: 7

```
cggcaccacc gacatcatct tcacctgccc tcgttccg                             38
```

<210> SEQ ID NO 8
<211> LENGTH: 38
<212> TYPE: DNA
<213> ORGANISM: Artificial Sequence
<220> FEATURE:
<223> OTHER INFORMATION: Synthetic construct

<400> SEQUENCE: 8

```
cggaacgagg gcaggtgaag atgatgtcgg tggtgccg                             38
```

<210> SEQ ID NO 9
<211> LENGTH: 1263
<212> TYPE: DNA
<213> ORGANISM: Corynebacterium glutamicum

<400> SEQUENCE: 9

```
gtggccctgg tcgtacagaa atatggcggt tcctcgcttg agagtgcgga acgcattaga    60
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat ctttcacggg ctctcaggct    300
ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg ctttgaacgc tgatgtgtgt gagatttact cggacgttga cggtgtgtat    540
accgctgacc cgcgcatcgt tcctaatgca cagaagctgg aaaagctcag cttcgaagaa    600
```

```
atgctggaac ttgctgctgt tggctccaag attttggtgc tgcgcagtgt tgaatacgct      660
cgtgcattca atgtgccact tcgcgtacgc tcgtcttata gtaatgatcc cggcactttg      720
attgccggct ctatggagga tattcctgtg aagaagcag tccttaccgg tgtcgcaacc       780
gacaagtccg aagccaaagt aaccgttctg ggtatttccg ataagccagg cgaggctgcg      840
aaggttttcc gtgcgttggc tgatgcagaa atcaacattg acatggttct gcagaacgtc      900
tcttctgtag aagacggcac caccgacatc accttcacct gccctcgttc cgacggccgc      960
cgcgcgatgg agatcttgaa gaagcttcag gttcagggca actggaccaa tgtgctttac     1020
gacgaccagg tcggcaaagt ctccctcgtg ggtgctggca tgaagtctca cccaggtgtt     1080
accgcagagt tcatggaagc tctgcgcgat gtcaacgtga acatcgaatt gatttccacc     1140
tctgagattc gtatttccgt gctgatccgt gaagatgatc tggatgctgc tgcacgtgca     1200
ttgcatgagc agttccagct gggcggcgaa gacgaagccg tcgtttatgc aggcaccgga     1260
cgc                                                                   1263

<210> SEQ ID NO 10
<211> LENGTH: 5860
<212> TYPE: DNA
<213> ORGANISM: Corynebacterium glutamicum

<400> SEQUENCE: 10
cccggtacca cgcgtcccag tggctgagac gcatccgcta aagccccagg aaccctgtgc       60
agaaagaaaa cactcctctg ctaggtagaa cacagtttat aaaggtagag ttgagcgggt      120
aactgtcagc acgtagatcg aaaggtgcac aaaggtggcc ctggtcgtac agaaatatgg      180
cggttcctcg cttgagagtg cggaacgcat tagaaacgtc gctgaacgga tcgttgccac      240
caagaaggct ggaaatgatg tcgtggttgt ctgctccgca atgggagaca ccacggatga      300
acttctagaa cttgcagcgg cagtgaatcc cgttccgcca gctcgtgaaa tggatatgct      360
cctgactgct ggtgagcgta tttctaacgc tctcgtcgcc atggctattg agtcccttgg      420
cgcagaagcc caatctttca cgggctctca ggctggtgtg ctcaccaccg agcgccacgg      480
aaacgcacgc attgttgatg tcactccagg tcgtgtgcgt gaagcactcg atgagggcaa      540
gatctgcatt gttgctggtt tccagggtgt taataaagaa accgcgatg tcaccacgtt       600 gggtcgtggt ggttctgaca ccactgcagt tgcgttggca gctgctttga acgctgatgt      660
gtgtgagatt tactcggacg ttgacggtgt gtataccgct gacccgcgca tcgttcctaa      720
tgcacagaag ctggaaaagc tcagcttcga agaaatgctg gaacttgctg ctgttggctc      780
caagattttg gtgctgcgca gtgttgaata cgctcgtgca ttcaatgtgc cacttcgcgt      840
acgctcgtct tatagtaatg atccccggcac tttgattgcc ggctctatgg aggatattcc      900 tgtgaagaa gcagtcctta ccggtgtcgc aaccgacaag tccgaagcca agtaaccgt       960 tctgggtatt tccgataagc caggcgaggc tgcgaaggtt ttccgtgcgt tggctgatgc     1020
agaaatcaac attgacatgg ttctgcagaa cgtctcttct gtagaagacg gcaccaccga     1080
catcatcttc acctgccctc gttccgacgg ccgccgcgcg atggagatct tgaagaagct     1140
tcaggttcag ggcaactgga ccaatgtgct ttacgacgac caggtcggca agtctccct       1200 cgtgggtgct ggcatgaagt ctcacccagg tgttaccgca gagttcatgg aagctctgcg     1260
cgatgtcaac gtgaacatcg aattgatttc cacctctgag attcgtattt ccgtgctgat     1320
ccgtgaagat gatctggatg ctgctgcacg tgcattgcat gagcagttcc agctgggcgg     1380
cgaagacgaa gccgtcgttt atgcaggcac cggacgctaa agtttta aag gagtagtttt    1440
```

```
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg gcggttttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg    2880 ggacgccggc tggatgatcc tccagcgcgg ggatctcatg ctggagttct cgcccacgc    2940 tagcggcgcg ccgcccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt atttggtatc tgcgctctgc    3660
tgaagccagt taccttcgga aaaagagttg gtagctcttg atccggcaaa caaaccaccg    3720
ctggtagcgg tggttttttt gtttgcaagc agcagattac gcgcagaaaa aaggatctc    3780 aagaagatcc tttgatcttt tctacggggt ctgacgctca gtggaacgaa aactcacgtt    3840
```

```
aagggattttt ggtcatgaga ttatcaaaaa ggatcttcac ctagatcctt ttaaaggccg      3900
gccgcggccg ccatcggcat tttcttttgc gttttttattt gttaactgtt aattgtcctt      3960
gttcaaggat gctgtctttg acaacagatg ttttcttgcc tttgatgttc agcaggaagc      4020
tcggcgcaaa cgttgattgt tgtctgcgt agaatcctct gtttgtcata tagcttgtaa       4080
tcacgacatt gtttcctttc gcttgaggta cagcgaagtg tgagtaagta aaggttacat      4140
cgttaggatc aagatccatt tttaacacaa ggccagtttt gttcagcggc ttgtatgggc      4200
cagttaaaga attagaaaca taaccaagca tgtaaatatc gttagacgta atgccgtcaa      4260 tcgtcattt tgatccgcgg gagtcagtga acaggtacca tttgccgttc attttaaaga       4320
cgttcgcgcg ttcaatttca tctgttactg tgttagatgc aatcagcggt ttcatcactt      4380
ttttcagtgt gtaatcatcg tttagctcaa tcataccgag agcgccgttt gctaactcag      4440
ccgtgcgttt tttatcgctt tgcagaagtt tttgactttc ttgacggaag aatgatgtgc      4500
ttttgccata gtatgctttg ttaaataaag attcttcgcc ttggtagcca tcttcagttc      4560
cagtgtttgc ttcaaatact aagtatttgt ggcctttatc ttctacgtag tgaggatctc      4620
tcagcgtatg gttgtcgcct gagctgtagt tgccttcatc gatgaactgc tgtacatttt      4680
gatacgtttt tccgtcaccg tcaaagattg atttataatc ctctacaccg ttgatgttca      4740
aagagctgtc tgatgctgat acgttaactt gtgcagttgt cagtgtttgt ttgccgtaat      4800
gtttaccgga gaaatcagtg tagaataaac ggattttcc gtcagatgta aatgtggctg       4860
aacctgacca ttcttgtgtt tggtctttta ggatagaatc atttgcatcg aatttgtcgc      4920
tgtctttaaa gacgcggcca gcgttttttcc agctgtcaat agaagtttcg ccgacttttt      4980
gatagaacat gtaaatcgat gtgtcatccg cattttagg atctccggct aatgcaaaga       5040
cgatgtggta gccgtgatag tttgcgacag tgccgtcagc gttttgtaat ggccagctgt      5100
cccaaacgtc caggcctttt gcagaagaga tatttttaat tgtggacgaa tcaaattcag      5160
aaacttgata ttttttcattt ttttgctgtt cagggatttg cagcatatca tggcgtgtaa     5220
tatgggaaat gccgtatgtt tccttatatg gcttttggtt cgtttctttc gcaaacgctt     5280
gagttgcgcc tcctgccagc agtgcggtag taaaggttaa tactgttgct tgttttgcaa     5340 acttttttgat gttcatcgtt catgtctcct tttttatgta ctgtgttagc ggtctgcttc    5400
ttccagccct cctgtttgaa gatggcaagt tagttacgca caataaaaaa agacctaaaa     5460
tatgtaaggg gtgacgccaa agtatacact ttgccctttta cacattttag gtcttgcctg    5520
ctttatcagt aacaaacccg cgcgatttac ttttcgacct cattctatta gactctcgtt     5580
tggattgcaa ctggtctatt ttcctctttt gtttgataga aaatcataaa aggatttgca     5640
gactacgggc ctaaagaact aaaaaatcta tctgtttctt ttcattctct gtattttta      5700 tagtttctgt tgcatgggca taaagttgcc tttttaatca caattcagaa aatatcataa     5760
tatctcattt cactaaataa tagtgaacgg caggtatatg tgatgggtta aaaaggatcg     5820
gcggccgctc gatttaaatc tcgagaggcc tgacgtcggg                           5860
```

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
tggccgttac cctgcgaatg                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
tgtatgtcct cctggacttc                                          20

<210> SEQ ID NO 13
<211> LENGTH: 40
<212> TYPE: DNA
<213> ORGANISM: Artificial Sequence
<220> FEATURE:
<223> OTHER INFORMATION: Synthetic construct

<400> SEQUENCE: 13
gaagtccagg aggacataca atgaacctaa agaaccccga                    40

<210> SEQ ID NO 14
<211> LENGTH: 31
<212> TYPE: DNA
<213> ORGANISM: Artificial Sequence
<220> FEATURE:
<223> OTHER INFORMATION: Synthetic construct

<400> SEQUENCE: 14
atctacgtcg acccaggatg ccctggattt c                             31

<210> SEQ ID NO 15
<211> LENGTH: 31
<212> TYPE: DNA
<213> ORGANISM: Artificial Sequence
<220> FEATURE:
<223> OTHER INFORMATION: Synthetic construct

<400> SEQUENCE: 15
tatcaacgcg ttcttcatcg gtagcagcac c                             31

<210> SEQ ID NO 16
<211> LENGTH: 37
<212> TYPE: DNA
<213> ORGANISM: Artificial Sequence
<220> FEATURE:
<223> OTHER INFORMATION: Synthetic construct

<400> SEQUENCE: 16
cattcgcagg gtaacggcca ctgaagggcc tcctggg                       37

<210> SEQ ID NO 17
<211> LENGTH: 5928
<212> TYPE: DNA
<213> ORGANISM: Corynebacterium glutamicum

<400> SEQUENCE: 17
tcgagaggcc tgacgtcggg cccggtacca cgcgttcttc atcggtagca gcacccgaga        60
ccatgacgcg ggcatcgccc agatccatca cacgcagatc acgcacatca gattcctgtg       120
aggtgtaaat tcccacgtcg tggccatcaa gatcataaga ctcagaaaga tcacgccagc       180
gagtatcata accagccaca gcatcctcaa cggtttcacc agtttgagtg agctgaatat       240
agccctcatc tgcggtgaca tatccaacta cagatgccgg ggtgtcatcc accatggtgc       300
gtcgagctga atttgtggtc cagccttcag gagtttccgg caacctagtt gcatgatcag       360

```
tcattgcgcg cgcttccatt gacataaaag tggaagcatc aacttcaggt acctgcccat    420
tttcagggga tcctgtattg aaagaacaca ttcccgtgaa tcccaccgct accaacatga    480
tgatcgcgga gactaccaac gagataatca tgtctcgact gccatcaaaa attttcggtc    540
gtttctcagc cacccgccta gtatgtcacg agtttggtac gaaacccct tttgggtgtc     600 cagaatccaa aattccgggc acaaaagtgc aacaatagat gacgtgcggg ttgatacagc    660
ccaagcgccg atacatttat aatgcgccta gatacgtgca acccacgtaa ccaggtcaga    720
tcaagtgccc caggaggccc ttcagtggcc gttaccctgc gaatgtccac agggtagctg    780
gtagtttgaa aatcaacgcc gttgcccta ggattcagta actggcacat tttgtaatgc     840
gctagatctg tgtgctcagt cttccaggct gcttatcaca gtgaaagcaa aaccaattcg    900
tggctgcgaa agtcgtagcc accacgaagt ccaggaggac atacaatgaa cctaaagaac    960
cccgaaacgc cagaccgtaa ccttgctatg gagctggtgc gagttacgga agcagctgca   1020
ctggcttctg gacgttgggt tggacgtggc atgaagaatg aaggcgacgg tgccgctgtt   1080
gacgccatgc gccagctcat caactcagtg accatgaagg gcgtcgttgt tatcggcgag   1140
ggcgaaaaag acgaagctcc aatgctgtac aacggcgaag aggtcggaac cggctttgga   1200
cctgaggttg atatcgcagt tgacccagtt gacggcacca ccctgatggc tgagggtcgc   1260
cccaacgcaa tttccattct cgcagctgca gagcgtggca ccatgtacga tccatcctcc   1320
gtcttctaca tgaagaagat cgccgtggga cctgaggccg caggcaagat cgacatcgaa   1380
gctccagttg cccacaacat caacgcgtgt gcaaagtcca agggaatcaa cccttccgac   1440
gtcaccgttg tcgtgcttga ccgtcctcgc cacatcgaac tgatcgcaga cattcgtcgt   1500
gcaggcgcaa aggttcgtct catctccgac ggcgacgttg caggtgcagt tgcagcagct   1560
caggattcca actccgtgga catcatgatg ggcaccggcg aacccccaga aggcatcatc   1620
actgcgtgcg ccatgaagtg catggtggc gaaatccagg gcatcctggg tcgacatcga    1680
tgctcttctg cgttaattaa caattgggat cctctagacc cgggatttaa atcgctagcg   1740
ggctgctaaa ggaagcggaa cacgtagaaa gccagtccgc agaaacggtg ctgacccgg    1800 atgaatgtca gctactgggc tatctggaca agggaaaacg caagcgcaaa gagaaagcag   1860
gtagcttgca gtgggcttac atggcgatag ctagactggg cggttttatg gacagcaagc   1920
gaaccggaat tgccagctgg ggcgccctct ggtaaggttg ggaagccctg caaagtaaac   1980
tggatggctt tcttgccgcc aaggatctga tggcgcaggg gatcaagatc tgatcaagag   2040
acaggatgag gatcgtttcg catgattgaa caagatggat tgcacgcagg ttctccggcc   2100
gcttgggtgg agaggctatt cggctatgac tgggcacaac agacaatcgg ctgctctgat   2160
gccgccgtgt tccggctgtc agcgcagggg cgcccggttc ttttttgtcaa gaccgacctg   2220 tccggtgccc tgaatgaact gcaggacgag gcagcgcggc tatcgtggct ggccacgacg   2280
ggcgttcctt gcgcagctgt gctcgacgtt gtcactgaag cgggaaggga ctggctgcta   2340
ttgggcgaag tgccggggca ggatctcctg tcatctcacc ttgctcctgc cgagaaagta   2400
tccatcatgg ctgatgcaat gcggcggctg catacgcttg atccggctac ctgcccattc   2460
gaccaccaag cgaaacatcg catcgagcga cacgtactc ggatggaagc cggtcttgtc    2520
gatcaggatg atctggacga agagcatcag gggctcgcgc cagccgaact gttcgccagg   2580
ctcaaggcgc gcatgcccga cggcgaggat ctcgtcgtga cccatggcga tgcctgcttg   2640
ccgaatatca tggtggaaaa tggccgcttt tctggattca tcgactgtgg ccggctgggt   2700
gtggcggacc gctatcagga catagcgttg gctacccgtg atattgctga agagcttggc   2760
```

```
ggcgaatggg ctgaccgctt cctcgtgctt tacggtatcg ccgctcccga ttcgcagcgc   2820
atcgccttct atcgccttct tgacgagttc ttctgagcgg gactctgggg ttcgaaatga   2880
ccgaccaagc gacgcccaac ctgccatcac gagatttcga ttccaccgcc gccttctatg   2940
aaaggttggg cttcggaatc gttttccggg acgccggctg gatgatcctc cagcgcgggg   3000
atctcatgct ggagttcttc gcccacgcta gcggcgcgcc ggccggcccg gtgtgaaata   3060
ccgcacagat gcgtaaggag aaaataccgc atcaggcgct cttccgcttc ctcgctcact   3120
gactcgctgc gctcggtcgt tcggctgcgg cgagcggtat cagctcactc aaaggcggta   3180
atacggttat ccacagaatc aggggataac gcaggaaaga acatgtgagc aaaaggccag   3240
caaaaggcca ggaaccgtaa aaaggccgcg ttgctggcgt ttttccatag gctccgcccc   3300
cctgacgagc atcacaaaaa tcgacgctca agtcagaggt ggcgaaaccc gacaggacta   3360
taaagatacc aggcgtttcc ccctggaagc tccctcgtgc gctctcctgt tccgaccctg   3420
ccgcttaccg gatacctgtc cgcctttctc ccttcgggaa gcgtggcgct ttctcatagc   3480
tcacgctgta ggtatctcag ttcggtgtag tcgttcgctc caagctgggc tgtgtgcac    3540 gaaccccccg ttcagcccga ccgctgcgcc ttatccggta actatcgtct tgagtccaac   3600
ccggtaagac acgacttatc gccactggca gcagccactg gtaacaggat tagcagagcg   3660
aggtatgtag gcggtgctac agagttcttg aagtggtggc ctaactacgg ctacactaga   3720
aggacagtat ttggtatctg cgctctgctg aagccagtta ccttcggaaa aagagttggt   3780
agctcttgat ccggcaaaca aaccaccgct ggtagcggtg gtttttttgt ttgcaagcag   3840
cagattacgc gcagaaaaaa aggatctcaa gaagatcctt tgatcttttc tacggggtct   3900
gacgctcagt ggaacgaaaa ctcacgttaa gggattttgg tcatgagatt atcaaaaagg   3960
atcttcacct agatcctttt aaaggccggc gcggccgcc atcggcattt tcttttgcgt    4020
ttttatttgt taactgttaa ttgtccttgt tcaaggatgc tgtctttgac aacagatgtt   4080
ttcttgcctt tgatgttcag caggaagctc ggcgcaaacg ttgattgttt gtctgcgtag   4140
aatcctctgt ttgtcatata gcttgtaatc acgacattgt ttcctttcgc ttgaggtaca   4200
gcgaagtgtg agtaagtaaa ggttacatcg ttaggatcaa gatccatttt taacacaagg   4260
ccagttttgt tcagcggctt gtatgggcca gttaaagaat tagaaacata accaagcatg   4320
taaatatcgt tagacgtaat gccgtcaatc gtcattttg atccgcggga gtcagtgaac    4380
aggtaccatt tgccgttcat tttaaagacg ttcgcgcgtt caatttcatc tgttactgtg   4440
ttagatgcaa tcagcggttt catcactttt ttcagtgtgt aatcatcgtt tagctcaatc   4500
ataccgagag cgccgtttgc taactcagcc gtgcgttttt tatcgctttg cagaagtttt   4560
tgactttctt gacggaagaa tgatgtgctt ttgccatagt atgctttgtt aaataaagat   4620
tcttcgcctt ggtagccatc ttcagttcca gtgtttgctt caaatactaa gtatttgtgg   4680
cctttatctt ctacgtagtg aggatctctc agcgtatggt tgtcgcctga gctgtagttg   4740
ccttcatcga tgaactgctg tacatttga tacgttttc cgtcaccgtc aaagattgat    4800
ttataatcct ctacaccgtt gatgttcaaa gagctgtctg atgctgatac gttaacttgt   4860
gcagttgtca gtgtttgttt gccgtaatgt ttaccggaga atcagtgta gaataaacgg     4920 atttttccgt cagatgtaaa tgtggctgaa cctgaccatt cttgtgtttg gtcttttagg   4980
atagaatcat ttgcatcgaa tttgtcgctg tctttaaaga cgcggccagc gttttttccag  5040 ctgtcaaatag aagtttcgcc gacttttga tagaacatga aaatcgatgt gtcatccgca   5100
tttttaggat ctccggctaa tgcaaagacg atgtggtagc cgtgatagtt tgcgacagtg   5160
```

```
ccgtcagcgt ttgtaatgg ccagctgtcc caaacgtcca ggccttttgc agaagagata    5220 ttttaattg tggacgaatc aaattcagaa acttgatatt tttcattttt ttgctgttca    5280
gggatttgca gcatatcatg gcgtgtaata tgggaaatgc cgtatgtttc cttatatggc    5340
ttttggttcg tttctttcgc aaacgcttga gttgcgcctc ctgccagcag tgcggtagta    5400
aaggttaata ctgttgcttg ttttgcaaac ttttttgatgt tcatcgttca tgtctccttt    5460
tttatgtact gtgttagcgg tctgcttctt ccagccctcc tgtttgaaga tggcaagtta    5520
gttacgcaca ataaaaaaag acctaaaata tgtaagggt gacgccaaag tatacacttt    5580 gcccttaca catttaggt cttgcctgct ttatcagtaa caaacccgcg cgatttactt    5640
ttcgacctca ttctattaga ctctcgtttg gattgcaact ggtctatttt cctcttttgt    5700
ttgatagaaa atcataaag gatttgcaga ctacgggcct aaagaactaa aaaatctatc    5760
tgtttctttt cattctctgt attttttata gtttctgttg catgggcata aagttgcctt    5820
tttaatcaca attcagaaaa tatcataata tctcatttca ctaaataata gtgaacggca    5880
ggtatatgtg atgggttaaa aaggatcggc ggccgctcga tttaaatc                5928
```

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
tagctgccaa ttattccggg                                                 20

<210> SEQ ID NO 19
<211> LENGTH: 20
<212> TYPE: DNA
<213> ORGANISM: Artificial Sequence
<220> FEATURE:
<223> OTHER INFORMATION: synthetic construct

<400> SEQUENCE: 19
gggtaaaaaa tcctttcgta                                                 20

<210> SEQ ID NO 20
<211> LENGTH: 37
<212> TYPE: DNA
<213> ORGANISM: Artificial Sequence
<220> FEATURE:
<223> OTHER INFORMATION: synthetic construct

<400> SEQUENCE: 20
cccggaataa ttggcagcta ctgaagggcc tcctggg                              37

<210> SEQ ID NO 21
<211> LENGTH: 31
<212> TYPE: DNA
<213> ORGANISM: Artificial Sequence
<220> FEATURE:
<223> OTHER INFORMATION: synthetic construct

<400> SEQUENCE: 21
tatcaacgcg ttcttcatcg gtagcagcac c                                    31

<210> SEQ ID NO 22
<211> LENGTH: 40
<212> TYPE: DNA
<213> ORGANISM: Artificial Sequence
<220> FEATURE:
<223> OTHER INFORMATION: synthetic construct

<400> SEQUENCE: 22
tacgaaagga ttttttaccc atgaacctaa agaaccccga        40

<210> SEQ ID NO 23
<211> LENGTH: 31
<212> TYPE: DNA
<213> ORGANISM: Artificial Sequence
<220> FEATURE:
<223> OTHER INFORMATION: synthetic construct

<400> SEQUENCE: 23
atctacgtcg acccaggatg ccctggattt c        31

<210> SEQ ID NO 24
<211> LENGTH: 5920
<212> TYPE: DNA
<213> ORGANISM: Artificial Sequence
<220> FEATURE:
<223> OTHER INFORMATION: synthetic construct

<400> SEQUENCE: 24
cgcgttcttc atcggtagca gcacccgaga ccatgacgcg ggcatcgccc agatccatca        60
cacgcagatc acgcacatca gattcctgtg aggtgtaaat tcccacgtcg tggccatcaa       120
gatcataaga ctcagaaaga tcacgccagc gagtatcata accagccaca gcatcctcaa       180
cggtttcacc agtttgagtg agctgaatat agccctcatc tgcggtgaca tatccaacta       240
cagatgccgg ggtgtcatcc accatggtgc gtcgagctga atttgtggtc agccttcag       300
gagtttccgg caacctagtt gcatgatcag tcattgcgcg cgcttccatt gacataaaag       360
tggaagcatc aacttcaggt acctgcccat tttcagggga tcctgtattg aaagaacaca       420
ttcccgtgaa tcccaccgct accaacatga tgatcgcgga gactaccaac gagataatca       480
tgtctcgact gccatcaaaa atttctcggtc gtttctcagc cacccgccta gtatgtcacg       540
agtttggtac gaaacccct tttgggtgtc cagaatccaa aattccgggc acaaaagtgc       600
aacaatagat gacgtgcggg ttgatacagc ccaagcgccg atacatttat aatgcgccta       660
gatacgtgca acccacgtaa ccaggtcaga tcaagtgccc caggaggccc ttcagtagct       720
gccaattatt ccgggcttgt gacccgctac ccgataaata ggtcggctga aaaatttcgt       780
tgcaatatca acaaaaaggc ctatcattgg gaggtgtcgc accaagtact tttgcgaagc       840
gccatctgac ggattttcaa aagatgtata tgctcggtgc ggaaacctac gaaaggattt       900
tttacccatg aacctaaaga ccccgaaac gccagaccgt aaccttgcta tggagctggt       960
gcgagttacg gaagcagctg cactggcttc tggacgttgg gttggacgtg gcatgaagaa      1020
tgaaggcgac ggtgccgctg ttgacgccat gcgccagctc atcaactcag tgaccatgaa      1080
gggcgtcgtt gttatcggcg agggcgaaaa agacgaagct ccaatgctgt acaacggcga      1140
agaggtcgga accggctttg gacctgaggt tgatatcgca gttgacccag ttgacggcac      1200
caccctgatg gctgagggtc gccccaacgc aatttccatt ctcgcagctg cagagcgtgg      1260
caccatgtac gatccatcct ccgtcttcta catgaagaag atcgccgtgg acctgaggc      1320
cgcaggcaag atcgacatcg aagctccagt tgcccacaac atcaacgcgg tggcaaagtc      1380
caagggaatc aacccttccg acgtcaccgt tgtcgtgctt gaccgtcctc gccacatcga      1440
actgatcgca gacattcgtc gtgcaggcgc aaaggttcgt ctcatctccg acggcgacgt      1500
tgcaggtgca gttgcagcag ctcaggattc caactccgtg gacatcatga tgggcaccgg      1560

```
cggaacccca gaaggcatca tcactgcgtg cgccatgaag tgcatgggtg gcgaaatcca   1620
gggcatcctg ggtcgacatc gatgctcttc tgcgttaatt aacaattggg atcctctaga   1680
cccgggattt aaatcgctag cgggctgcta aggaagcgga acacgtaga aagccagtcc    1740 gcagaaacgg tgctgacccc ggatgaatgt cagctactgg gctatctgga caagggaaaa   1800
cgcaagcgca aagagaaagc aggtagcttg cagtgggctt acatggcgat agctagactg   1860
ggcggtttta tggacagcaa gcgaaccgga attgccagct ggggcgccct ctggtaaggt   1920
tgggaagccc tgcaaagtaa actggatggc tttcttgccg ccaaggatct gatggcgcag   1980
gggatcaaga tctgatcaag agacaggatg aggatcgttt cgcatgattg aacaagatgg   2040
attgcacgca ggttctccgg ccgcttgggt ggagaggcta ttcggctatg actgggcaca   2100
acagacaatc ggctgctctg atgccgccgt gttccggctg tcagcgcagg ggcgcccggt   2160 tcttttgtc aagaccgacc tgtccggtgc cctgaatgaa ctgcaggacg aggcagcgcg   2220
gctatcgtgg ctggccacga cgggcgttcc ttgcgcagct gtgctcgacg ttgtcactga   2280
agcgggaagg gactggctgc tattgggcga agtgccgggg caggatctcc tgtcatctca   2340
ccttgctcct gccgagaaag tatccatcat ggctgatgca atgcggcggc tgcatacgct   2400
tgatccggct acctgcccat tcgaccacca agcgaaacat cgcatcgagc gagcacgtac   2460
tcggatggaa gccggtcttg tcgatcagga tgatctggac gaagagcatc aggggctcgc   2520
gccagccgaa ctgttcgcca ggctcaaggc gcgcatgccc gacggcgagg atctcgtcgt   2580
gacccatggc gatgcctgct tgccgaatat catggtggaa aatggccgct tttctggatt   2640
catcgactgt ggccggctgg gtgtggcgga ccgctatcag gacatagcgt tggctacccg   2700
tgatattgct gaagagcttg gcggcgaatg ggctgaccgc ttcctcgtgc tttacggtat   2760
cgccgctccc gattcgcagc gcatcgcctt ctatcgcctt cttgacgagt tcttctgagc   2820
gggactctgg ggttcgaaat gaccgaccaa gcgacgccca acctgccatc acgagatttc   2880
gattccaccg ccgccttcta tgaaaggttg ggcttcggaa tcgttttccg gacgccggc   2940 tggatgatcc tccagcgcgg ggatctcatg ctggagttct cgcccacgc tagcggcgcg   3000 ccggccggcc cggtgtgaaa taccgcacag atgcgtaagg agaaaatacc gcatcaggcg   3060
ctcttccgct tcctcgctca ctgactcgct gcgctcggtc gttcggctgc ggcgagcggt   3120
atcagctcac tcaaaggcgg taatacggtt atccacagaa tcaggggata acgcaggaaa   3180
gaacatgtga gcaaaaggcc agcaaaaggc caggaaccgt aaaaaggccg cgttgctggc   3240
gtttttccat aggctccgcc cccctgacga gcatcacaaa aatcgacgct caagtcagag   3300
gtggcgaaac ccgacaggac tataaagata ccaggcgttt ccccctggaa gctccctcgt   3360
gcgctctcct gttccgaccc tgccgcttac cggatacctg tccgcctttc tcccttcggg   3420
aagcgtggcg ctttctcata gctcacgctg taggtatctc agttcggtgt aggtcgttcg   3480
ctccaagctg ggctgtgtgc acgaaccccc cgttcagccc gaccgctgcg ccttatccgg   3540
taactatcgt cttgagtcca acccggtaag acacgactta tcgccactgg cagcagccac   3600
tggtaacagg attagcagag cgaggtatgt aggcggtgct acagagttct tgaagtggtg   3660
gcctaactac ggctacacta gaaggacagt atttggtatc tgcgctctgc tgaagccagt   3720
taccttcgga aaaagagttg gtagctcttg atccggcaaa caaaccaccg ctggtagcgg   3780 tggtttttt gtttgcaagc agcagattac gcgcagaaaa aaggatctc aagaagatcc   3840 tttgatcttt tctacggggt ctgacgctca gtggaacgaa aactcacgtt aagggatttt   3900
ggtcatgaga ttatcaaaaa ggatcttcac ctagatcctt ttaaaggccg ccgcggccg   3960
```

-continued

```
ccatcggcat tttcttttgc gttttattt gttaactgtt aattgtcctt gttcaaggat    4020
gctgtctttg acaacagatg ttttcttgcc tttgatgttc agcaggaagc tcggcgcaaa    4080
cgttgattgt ttgtctgcgt agaatcctct gtttgtcata tagcttgtaa tcacgacatt    4140
gtttcctttc gcttgaggta cagcgaagtg tgagtaagta aaggttacat cgttaggatc    4200
aagatccatt tttaacacaa ggccagtttt gttcagcggc ttgtatgggc cagttaaaga    4260
attagaaaca taaccaagca tgtaaatatc gttagacgta atgccgtcaa tcgtcatttt    4320
tgatccgcgg gagtcagtga acaggtacca tttgccgttc atttaaaga cgttcgcgcg    4380
ttcaatttca tctgttactg tgttagatgc aatcagcggt ttcatcactt ttttcagtgt    4440
gtaatcatcg tttagctcaa tcataccgag agcgccgttt gctaactcag ccgtgcgttt    4500
tttatcgctt tgcagaagtt tttgactttc ttgacggaag aatgatgtgc ttttgccata    4560
gtatgctttg ttaaataaag attcttcgcc ttggtagcca tcttcagttc cagtgtttgc    4620
ttcaaatact aagtatttgt ggcctttatc ttctacgtag tgaggatctc tcagcgtatg    4680
gttgtcgcct gagctgtagt tgccttcatc gatgaactgc tgtacatttt gatacgtttt    4740
tccgtcaccg tcaaagattg atttataatc ctctacaccg ttgatgttca aagagctgtc    4800
tgatgctgat acgttaactt gtgcagttgt cagtgtttgt ttgccgtaat gtttaccgga    4860
gaaatcagtg tagaataaac ggattttttcc gtcagatgta aatgtggctg aacctgacca    4920
ttcttgtgtt tggtcttta ggatagaatc atttgcatcg aatttgtcgc tgtctttaaa    4980
gacgcggcca gcgttttttcc agctgtcaat agaagtttcg ccgactttt gatagaacat    5040
gtaaatcgat gtgtcatccg catttttagg atctccggct aatgcaaaga cgatgtggta    5100
gccgtgatag tttgcgacag tgccgtcagc gttttgtaat ggccagctgt cccaaacgtc    5160
caggcctttt gcagaagaga tattttttaat tgtggacgaa tcaaattcag aaacttgata    5220
tttttcattt ttttgctgtt cagggatttg cagcatatca tggcgtgtaa tatgggaaat    5280
gccgtatgtt tccttatatg gcttttggtt cgtttctttc gcaaacgctt gagttgcgcc    5340
tcctgccagc agtgcggtag taaaggttaa tactgttgct tgttttgcaa acttttgat    5400
gttcatcgtt catgtctcct tttttatgta ctgtgttagc ggtctgcttc ttccagccct    5460
cctgtttgaa gatggcaagt tagttacgca caataaaaaa agacctaaaa tatgtaaggg    5520
gtgacgccaa agtatacact ttgcccttta cacattttag gtcttgcctg ctttatcagt    5580
aacaaacccg cgcgatttac ttttcgacct cattctatta gactctcgtt tggattgcaa    5640
ctggtctatt ttcctctttt gtttgataga aaatcataaa aggatttgca gactacgggc    5700
ctaaagaact aaaaaatcta tctgtttctt ttcattctct gtattttta tagtttctgt    5760
tgcatgggca taaagttgcc tttttaatca caattcagaa aatatcataa tatctcatttt    5820
cactaaataa tagtgaacgg caggtatatg tgatgggtta aaaaggatcg gcggccgctc    5880
gatttaaatc tcgagaggcc tgacgtcggg cccggtacca                          5920
```

METHODS FOR THE PREPARATION OF LYSINE BY FERMENTATION OF CORYNEBACTERIUM GLUTAMICUM

RELATED APPLICATIONS

The present application is a divisional of U.S. application Ser. No. 12/021,081 filed Jan. 28, 2008, now abandoned, which is a divisional of U.S. application Ser. No. 10/579,690, filed Mar. 6, 2007, now abandoned, which is a 35 U.S.C. 371 national stage filing of International Application No. PCT/IB2004/004429, filed Dec. 17, 2004, which claims priority to International Application No. PCT/IB2003/006456, filed Dec. 18, 2003. The entire contents of each of these applications are hereby incorporated by reference herein.

SEQUENCE LISTING

This application incorporates herein by reference the sequence listing filed concurrently herewith, i.e., the file "SEQLIST.txt" (45.0 KB) created on Jul. 31, 2009.

BACKGROUND OF THE INVENTION

The industrial production of the amino acid lysine has became an economically important industrial process. Lysine is used commercially as an animal feed supplement, because of its ability to improve the quality of feed by increasing the absorption of other amino acids, in human medicine, particularly as ingredients of infusion solutions, and in the pharmaceutical industry.

Commercial production of this lysine is principally done utilizing the gram positive *Corynebacterium glutamicum*, *Brevibacterium flavum* and *Brevibacterium lactofermentum* (Kleemann, A., et. al., "Amino Acids," in ULLMANN'S ENCYCLOPEDIA OF INDUSTRIAL CHEMISTRY, vol. A2, pp. 57-97, Weinham: VCH-Verlagsgesellschaft (1985)). These organisms presently account for the approximately 250,000 tons of lysine produced annually. A significant amount of research has gone into isolating mutant bacterial strains which produce larger amounts of lysine. Microorganisms employed in microbial process for amino acid production are divided into 4 classes: wild-type strain, auxotrophic mutant, regulatory mutant and auxotrophic regulatory mutant (K. Nakayama et al., in *Nutritional Improvement of Food and Feed Proteins*, M. Friedman, ed., (1978), pp. 649-661). Mutants of *Corynebacterium* and related organisms enable inexpensive production of amino acids from cheap carbon sources, e.g., molasses, acetic acid and ethanol, by direct fermentation. In addition, the stereospecificity of the amino acids produced by fermentation (the L isomer) makes the process advantageous compared with synthetic processes.

Another method in improving the efficiency of the commercial production of lysine is by investigating the correlation between lysine production and metabolic flux through the pentose phosphate pathway. Given the economic importance of lysine production by the fermentive process, the biochemical pathway for lysine synthesis has been intensively investigated, ostensibly for the purpose of increasing the total amount of lysine produced and decreasing production costs (reviewed by Sahm et al, (1996) *Ann. N.Y. Acad. Sci.* 782:25-39). There has been some success in using metabolic engineering to direct the flux of glucose derived carbons toward aromatic amino acid formation (Flores, N. et al., (1996) *Nature Biotechnol.* 14:620-623). Upon cellular absorption, glucose is phosphorylated with consumption of phosphoenolpyruvate (phosphotransferase system) (Malin & Bourd, (1991) *Journal of Applied Bacteriology* 71, 517-523) and is then available to the cell as glucose-6-phosphate. Sucrose is converted into fructose and glucose-6-phosphate by a phosphotransferase system (Shio et ah, (1990) *Agricultural and Biological Chemistry* 54, 1513-1519) and invertase reaction (Yamamoto et al, (1986) *Journal of Fermentation Technology* 64, 285-291).

During glucose catabolism, the enzymes glucose-6-phosphate dehydrogenase (EC 1.1.14.9) and glucose-6-phosphate isomerase (EC 5.3.1.9) compete for the substrate glucose-6-phosphate. The enzyme glucose-6-phosphate isomerase catalyses the first reaction step of the Embden-Meyerhof-Parnas pathway, or glycolysis, namely conversion into fructose-6-phosphate. The enzyme glucose-6-phosphate dehydrogenase catalyses the first reaction step of the oxidative portion of the pentose phosphate cycle, namely conversion into 6-phosphogluconolactone.

In the oxidative portion of the pentose phosphate cycle, glucose-6-phosphate is converted into ribulose-5-phosphate, so producing reduction equivalents in the form of NADPH. As the pentose phosphate cycle proceeds further, pentose phosphates, hexose phosphates and triose phosphates are interconverted. Pentose phosphates, such as for example 5-phosphoribosyl-1-pyrophosphate are required, for example, in nucleotide biosynthesis. 5-Phosphoribosyl-1-pyrophosphate is moreover a precursor for aromatic amino acids and the amino acid L-histidine. NADPH acts as a reduction equivalent in numerous anabolic biosyntheses. Four molecules of NADPH are thus consumed for the biosynthesis of one molecule of lysine from oxalacetic acid. Thus, carbon flux towards oxaloacetate (OAA) remains constant regardless of system perturbations (J. Vallino et al, (1993) *Biotechnol. Bioeng.*, 41, 633-646).

SUMMARY OF THE INVENTION

The present invention is based, at least in part, on the discovery of key enzyme-encoding genes, e.g., fructose-1,6-bisphosphatase, of the pentose phosphate pathway in *Corynebacterium glutamicum*, and the discovery that deregulation, e.g., increasing expression or activity of fructose-1,6-bisphosphatase results in increased lysine production. Furthermore, it has been found that increasing the carbon yield during production of lysine by deregulating, e.g., increasing, fructose-1,6 bisphosphatase expression or activity leads to increased lysine production. In one embodiment, the carbon source is fructose or sucrose. Accordingly, the present invention provides methods for increasing production of lysine by microorganisms, e.g., *C. glutamicum*, where fructose or sucrose is the substrate.

Accordingly, in one aspect, the invention provides methods for increasing metabolic flux through the pentose phosphate pathway in a microorganism comprising culturing a microorganism comprising a gene which is deregulated under conditions such that metabolic flux through the pentose phosphate pathway is increased. In one embodiment, the microorganism is fermented to produce a fine chemical, e.g., lysine. In another embodiment, fructose or sucrose is used as a carbon source. In still another embodiment, the gene is fructose-1,6-bisphosphatase. In a related embodiment, the fructose-1,6-bisphosphatase gene is derived from *Corynebacterium*, e.g., *Corynebacterium glutamicum*. In another embodiment, fructose-1,6 bisphosphatase gene is overexpressed. In a further embodiment, the protein encoded by the fructose-1,6-bisphosphatase gene has increased activity.

In another embodiment, the microorganism further comprises one or more additional deregulated genes. The one or more additional deregulated gene can include, but is not limited to, an ask gene, a dapA gene, an asd gene, a dapB gene, a ddh gene, a lysA gene, a lysE gene, a pycA gene, a zwf gene, a pepCL gene, a gap gene, a zwa1 gene, a tkt gene, a tad gene, a mqo gene, a tpi gene, a pgk gene, and a sigC gene. In a particular embodiment, the gene may be overexpressed or underexpressed. Moreover, the deregulated gene can encode a protein selected from the group consisting of a feed-back resistant aspartokinase, a dihydrodipicolinate synthase, an aspartate semialdehyde dehydrogenase, a dihydrodipicolinate reductase, a diaminopimelate dehydrogenase, a diaminopimelate epimerase, a lysine exporter, a pyruvate carboxylase, a glucoses-phosphate dehydrogenase, a phosphoenolpyruvate carboxylase, a glyceraldedyde-3-phosphate dehydrogenase, an RPF protein precursor, a transketolase, a transaldolase, a menaquinine oxidoreductase, a triosephosphate isomerase, a 3-phosphoglycerate kinase, and an RNA-polymerase sigma factor sigC. In a particular embodiment, the protein may have an increased or a decreased activity.

In accordance with the methods of the present invention, the one or more additional deregulated genes can also include, but is not limited to, a pepCK gene, a mal E gene, a glgA gene, a pgi gene, a dead gene, a menE gene, a citE gene, a mikE17 gene, a poxB gene, a zwa2 gene, and a sucC gene. In a particular embodiment the expression of the at least one gene is upregulated, attenuated, decreased, downregulated or repressed. Moreover, the deregulated gene can encode a protein selected from the group consisting of a phosphoenolpyruvate carboxykinase, a malic enzyme, a glycogen synthase, a glucose-6-phosphate isomerase, an ATP dependent RNA helicase, an o-succinylbenzoic acid-CoA ligase, a citrate lyase beta chain, a transcriptional regulator, a pyruvate dehydrogenase, an RPF protein precursor, and a Succinyl-CoA-Synthetase. In a particular embodiment, the protein has a decreased or an increased activity.

In one embodiment, the microorganisms used in the methods of the invention belong to the genus *Corynebacterium*, e.g., *Corynebacterium glutamicum*.

In another aspect, the invention provides methods for producing a fine chemical comprising fermenting a microorganism in which fructose-1,6-bisphosphatase is deregulated and accumulating the fine chemical, e.g., lysine, in the medium or in the cells of the microorganisms, thereby producing a fine chemical. In one embodiment, the methods include recovering the fine chemical. In another embodiment, the fructose-1,6-bisphosphatase gene is overexpressed. In yet another embodiment, fructose or sucrose is used as a carbon source.

In one aspect, fructose-1,6-bisphosphatase is derived from *Corynebacterium glutamicum* and comprises the nucleotide sequence of SEQ ID NO:1 and the amino acid sequence of SEQ ID NO:2.

Other features and advantages of the invention will be apparent from the following detailed description and claims.

DETAILED DESCRIPTION OF THE INVENTION

Figure 1:
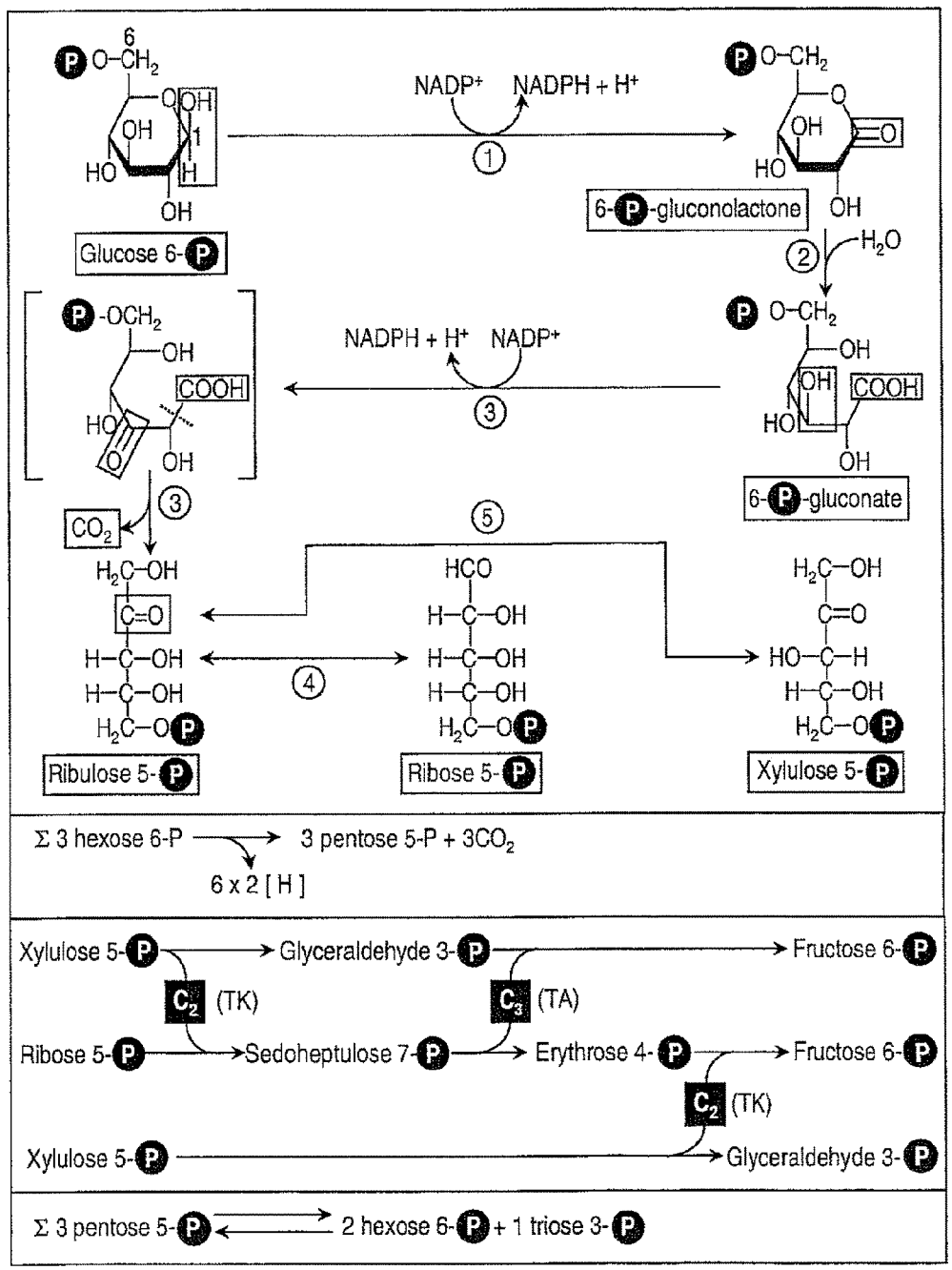
FIG. 1: is a schematic representation of the pentose biosynthetic pathway.

The present invention is based at least in part, on the identification of genes, e.g., *Corynebacterium glutamicum* genes, which encode essential enzymes of the pentose phosphate pathway. The present invention features methods comprising manipulating the pentose phosphate biosynthetic pathway in a microorganism, e.g., *Corynebacterium glutamicum* such that the carbon yield is increased and certain desirable fine chemicals, e.g., lysine, are produced, e.g., produced at increased yields. In particular, the invention includes methods for producing fine chemicals, e.g., lysine, by fermentation of a microorganism, e.g., *Corynebacterium glutamicum*, having deregulated, e.g., increased, fructose-1,6-bisphosphatase expression or activity. In one embodiment, fructose or saccharose is used as a carbon source in the fermentation of the microorganism. Fructose has been established to be a less efficient substrate for the production of fine chemicals, e.g., lysine, from microorganisms. However, the present invention provides methods for optimizing production of lysine by microorganisms, e.g., *C. glutamicum* where fructose or sucrose is the substrate. Deregulation, e.g., amplification, of fructose-1,6-bisphosphatase expression or activity leads to a higher flux through the pentose phosphate pathway, resulting in increased NADPH generation and increased lysine yield.

The term "pentose phosphate pathway" includes the pathway involving pentose phosphate enzymes (e.g., polypeptides encoded by biosynthetic enzyme-encoding genes), compounds (e.g., precursors, substrates, intermediates or products), cofactors and the like utilized in the formation or synthesis of fine chemicals, e.g., lysine. The pentose phosphate pathway converts glucose molecules into biochemically useful smaller molecule.

In order that the present invention may be more readily understood, certain terms are first defined herein.

The term "pentose phosphphate biosynthetic pathway" includes the biosynthetic pathway involving pentose phosphate biosynthetic genes, enzymes (e.g., polypeptides encoded by biosynthetic enzyme-encoding genes), compounds (e.g., precursors, substrates, intermediates or products), cofactors and the like utilized in the formation or synthesis of fine chemicals, e.g., lysine. The term "pentose phosphate biosynthetic pathway" includes the biosynthetic pathway leading to the synthesis of fine chemicals, e.g., lysine, in a microorganisms (e.g., in vivo) as well as the biosynthetic pathway leading to the synthesis of fine chemicals, e.g., lysine, in vitro. The term "pentose phosphate biosynthetic pathway protein" or "pentose phosphate biosynthetic pathway enzyme" includes a those peptides, polypeptides, proteins, enzymes, and fragments thereof which are directly or indirectly involved in the pentose phosphate biosynthetic pathway, e.g., the fructose-1,6-bisphosphatase enzyme.

The term "pentose phosphate biosynthetic pathway gene" includes a those genes and gene fragments encoding peptides, polypeptides, proteins, and enzymes which are directly or indirectly involved in the pentose phosphate biosynthetic pathway, e.g., the fructose-1,6-bisphosphatase gene.

The term "amino acid biosynthetic pathway gene" is meant to include those genes and gene fragments encoding peptides, polypeptides, proteins, and enzymes, which are directly involved in the synthesis of amino acids, e.g., fructose-1,6-bisphosphatase. These genes may be identical to those which naturally occur within a host cell and are involved in the synthesis of any amino acid, and particularly lysine, within that host cell.

The term "lysine biosynthetic pathway gene" includes those genes and genes fragments encoding peptides, polypeptides, proteins, and enzymes, which are directly involved in the synthesis of lysine, e.g., fructose-1,6-bisphosphatase. These genes can be identical to those which naturally occur within a host cell and are involved in the synthesis of lysine within that host cell. Alternatively, there can be modifications or mutations of such genes, for example, the genes can contain modifications or mutations which do not significantly affect the biological activity of the encoded protein. For example, the natural gene can be modified by mutagenesis or by introducing or substituting one or more nucleotides or by removing nonessential regions of the gene. Such modifications are readily performed by standard techniques.

The term "lysine biosynthetic pathway protein" is meant to include those peptides, polypeptides, proteins, enzymes, and fragments thereof which are directly involved in the synthesis of lysine. These proteins can be identical to those which naturally occur within a host cell and are involved in the synthesis of lysine within that host cell. Alternatively, there can be modifications or mutations of such proteins, for example, the proteins can contain modifications or mutations which do not significantly affect the biological activity of the protein. For example, the natural protein can be modified by mutagenesis or by introducing or substituting one or more amino acids, preferably by conservative amino acid substitution, or by removing nonessential regions of the protein. Such modifications are readily performed by standard techniques. Alternatively, lysine biosynthetic proteins can be heterologous to the particular host cell. Such proteins can be from any organism having genes encoding proteins having the same, or similar, biosynthetic roles.

The term, "carbon flux" refers to the number of glucose molecules which proceed down a particular metabolic path relative to competing paths. In particular, increased NADPH within a microorganism is achieved by altering the carbon flux distribution between the glycolytic and pentose phosphate pathways of that organism.

"Fructose-1,6-bisphosphatase activity" includes any activity exerted by a fructose-1,6-bisphosphatase protein, polypeptide or nucleic acid molecule as determined in vivo, or in vitro, according to standard techniques. Fructose-1,6-bisphosphatase is involved in many different metabolic pathways and found in most organisms. Preferably, a fructose-1,6-bisphosphatase activity includes the catalysis of the hydrolysis of fructose 1,6-bisphosphate to fructose 6-phosphate.

The term 'fine chemical' is art-recognized and includes molecules produced by an organism which have applications in various industries, such as, but not limited to, the pharmaceutical, agriculture, and cosmetics industries. Such compounds include organic acids, such as tartaric acid, itaconic acid, and diaminopimelic acid, both proteinogenic and nonproteinogenic amino acids, purine and pyrimidine bases, nucleosides, and nucleotides (as described e.g. in Kuninaka, A. (1996) Nucleotides and related compounds, p. 561-612, in Biotechnology vol. 6, Rehm et al, eds. VCH: Weinheim, and references contained therein), lipids, both saturated and unsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, "Vitamins", p. 443-613 (1996) VCH: Weinheim and references therein; and Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press, (1995)), enzymes, polyketides (Cane et al. (1998) *Science* 282: 63-68), and all other chemicals described in Gutcho (1983) Chemicals by Fermentation, Noyes Data Corporation, ISBN: 0818805086 and references therein. The metabolism and uses of certain of these fine chemicals are further explicated below.

Amino Acid Metabolism and Uses

Amino acids comprise the basic structural units of all proteins, and as such are essential for normal cellular functioning in all organisms. The term "amino acid" is art-recognized. The proteinogenic amino acids, of which there are 20 species, serve as structural units for proteins, in which they are linked by peptide bonds, while the nonproteinogenic amino acids (hundreds of which are known) are not normally found in proteins (see Ulmann's Encyclopedia of Industrial Chemistry, vol. A2, p. 57-97 VCH: Weinheim (1985)). Amino acids may be in the D- or L-optical configuration, though L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, $3^{rd}$ edition, pages 578-590 (1988)). The 'essential' amino acids (histidine, isoleucine, leucine, lysine, methionine, phenylalanine, threonine, tryptophan, and valine), so named because they are generally a nutritional requirement due to the complexity of their biosyntheses, are readily converted by simple biosynthetic pathways to the remaining 11 'nonessential' amino acids (alanine, arginine, asparagine, aspartate, cysteine, glutamate, glutamine, glycine, proline, serine, and tyrosine). Higher animals do retain the ability to synthesize some of these amino acids, but the essential amino acids must be supplied from the diet in order for normal protein synthesis to occur.

Aside from their function in protein biosynthesis, these amino acids are interesting chemicals in their own right, and many have been found to have various applications in the food, feed, chemical, cosmetics, agriculture, and pharmaceutical industries. Lysine is an important amino acid in the nutrition not only of humans, but also of monogastric animals such as poultry and swine. Glutamate is most commonly used as a flavor additive (mono-sodium glutamate, MSG) and is widely used throughout the food industry, as are aspartate, phenylalanine, glycine, and cysteine. Glycine, L-methionine and tryptophan are all utilized in the pharmaceutical industry. Glutamine, valine, leucine, isoleucine, histidine, arginine, proline, serine and alanine are of use in both the pharmaceutical and cosmetics industries. Threonine, tryptophan, and D/L-methionine are common feed additives. (Leuchtenberger, W. (1996) Amino aids—technical production and use, p. 466-502 in Rehm et al. (eds.) Biotechnology vol. 6, chapter 14a, VCH: Weinheim). Additionally, these amino acids have been found to be useful as precursors for the synthesis of synthetic amino acids and proteins, such as N-acetylcysteine, S-carboxymethyl-L-cysteine, (S)-5-hydroxytryptophan, and others described in Ulmann's Encyclopedia of Industrial Chemistry, vol. A2, p. 57-97, VCH: Weinheim, 1985.

The biosynthesis of these natural amino acids in organisms capable of producing them, such as bacteria, has been well characterized (for review of bacterial amino acid biosynthesis and regulation thereof, see Umbarger, H. E. (1978) *Ann. Rev. Biochem.* 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain β-carbon atom to tetrahydrofolate, in a reaction catalyzed by serine transhydroxymethylase. Phenylalanine, and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine. A complex 9-step pathway results in the production of histidine from 5-phosphoribosyl-1-pyrophosphate, an activated sugar.

Amino acids in excess of the protein synthesis needs of the cell cannot be stored, and are instead degraded to provide intermediates for the major metabolic pathways of the cell (for review see Stryer, L. Biochemistry $3^{rd}$ ed. Ch. 21 "Amino Acid Degradation and the Urea Cycle" p. 495-516 (1988)). Although the cell is able to convert unwanted amino acids into useful metabolic intermediates, amino acid production is costly in terms of energy, precursor molecules, and the enzymes necessary to synthesize them. Thus it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L. Biochemistry, $3^{rd}$ ed. Ch. 24: "Biosynthesis of Amino Acids and Heme" p. 575-600 (1988)). Thus, the output of any particular amino acid is limited by the amount of that amino acid present in the cell.

Vitamin, Cofactor, and Nutraceutical Metabolism and Uses

Vitamins, cofactors, and nutraceuticals comprise another group of molecules which the higher animals have lost the ability to synthesize and so must ingest, although they are readily synthesized by other organisms such as bacteria. These molecules are either bioactive substances themselves, or are precursors of biologically active substances which may serve as electron carriers or intermediates in a variety of metabolic pathways. Aside from their nutritive value, these compounds also have significant industrial value as coloring agents, antioxidants, and catalysts or other processing aids. (For an overview of the structure, activity, and industrial applications of these compounds, see, for example, Ullman's Encyclopedia of Industrial Chemistry, "Vitamins" vol. A27, p. 443-613, VCH: Weinheim, 1996.) The term "Vitamin" is art-recognized, and includes nutrients which are required by an organism for normal functioning, but which that organism cannot synthesize by itself. The group of vitamins may encompass cofactors and nutraceutical compounds. The language "cofactor" includes nonproteinaceous compounds required for a normal enzymatic activity to occur. Such compounds may be organic or inorganic; the cofactor molecules of the invention are preferably organic. The term "nutraceutical" includes dietary supplements having health benefits in plants and animals, particularly humans. Examples of such molecules are vitamins, antioxidants, and also certain lipids (e.g., polyunsaturated fatty acids).

The biosynthesis of these molecules in organisms capable of producing them, such as bacteria, has been largely characterized (Ullman's Encyclopedia of Industrial Chemistry, "Vitamins" vol. A27, p. 443-613, VCH: Weinheim, 1996; Michal, G. (1999) Biochemical Pathways: An Atlas of Biochemistry and Molecular Biology, John Wiley & Sons; Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press: Champaign, Ill. X, 374 S).

Thiamin (vitamin $B_1$) is produced by the chemical coupling of pyrimidine and thiazole moieties. Riboflavin (vitamin $B_2$) is synthesized from guanosine-5'-triphosphate (GTP) and ribose-5'-phosphate. Riboflavin, in turn, is utilized for the synthesis of flavin mononucleotide (FMN) and flavin adenine dinucleotide (FAD). The family of compounds collectively termed 'vitamin $B_6$' (e.g., pyridoxine, pyridoxamine, pyridoxa-5'-phosphate, and the commercially used pyridoxin hydrochloride) are all derivatives of the common structural unit, 5-hydroxy-6-methylpyridine. Pantothenate (pantothenic acid, (R)-(+)-N-(2,4-dihydroxy-3,3-dimethyl-1-oxobutyl)-β-alanine) can be produced either by chemical synthesis or by fermentation. The final steps in pantothenate biosynthesis consist of the ATP-driven condensation of β-alanine and pantoic acid. The enzymes responsible for the biosynthesis steps for the conversion to pantoic acid, to β-alanine and for the condensation to panthotenic acid are known. The metabolically active form of pantothenate is Coenzyme A, for which the biosynthesis proceeds in 5 enzymatic steps. Pantothenate, pyridoxal-5'-phosphate, cysteine and ATP are the precursors of Coenzyme A. These enzymes not only catalyze the formation of panthothante, but also the production of (R)-pantoic acid, (R)-pantolacton, (R)-panthenol (provitamin $B_5$), pantetheine (and its derivatives) and coenzyme A.

Biotin biosynthesis from the precursor molecule pimeloyl-CoA in microorganisms has been studied in detail and several of the genes involved have been identified. Many of the corresponding proteins have been found to also be involved in Fe-cluster synthesis and are members of the nifS class of proteins. Lipoic acid is derived from octanoic acid, and serves as a coenzyme in energy metabolism, where it becomes part of the pyruvate dehydrogenase complex and the α-ketoglutarate dehydrogenase complex. The folates are a group of substances which are all derivatives of folic acid, which is turn is derived from L-glutamic acid, p-amino-benzoic acid and 6-methylpterin. The biosynthesis of folic acid and its derivatives, starting from the metabolism intermediates guanosine-5'-triphosphate (GTP), L-glutamic acid and p-aminobenzoic acid has been studied in detail in certain microorganisms.

Corrinoids (such as the cobalamines and particularly vitamin $B_{12}$) and porphyrines belong to a group of chemicals characterized by a tetrapyrole ring system. The biosynthesis of vitamin $B_{12}$ is sufficiently complex that it has not yet been completely characterized, but many of the enzymes and substrates involved are now known.

Nicotinic acid (nicotinate), and nicotinamide are pyridine derivatives which are also termed 'niacin'. Niacin is the precursor of the important coenzymes NAD (nicotinamide adenine dinucleotide) and NADP (nicotinamide adenine dinucleotide phosphate) and their reduced forms.

The large-scale production of these compounds has largely relied on cell-free chemical syntheses, though some of these chemicals have also been produced by large-scale culture of microorganisms, such as riboflavin, Vitamin $B_6$, pantothenate, and biotin. Only Vitamin $B_{12}$ is produced solely by fermentation, due to the complexity of its synthesis. In vitro methodologies require significant inputs of materials and time, often at great cost.

Purine, Pyrimidine, Nucleoside and Nucleotide Metabolism and Uses

Purine and pyrimidine metabolism genes and their corresponding proteins are important targets for the therapy of tumor diseases and viral infections. The language "purine" or "pyrimidine" includes the nitrogenous bases which are constituents of nucleic acids, co-enzymes, and nucleotides. The term "nucleotide" includes the basic structural units of nucleic acid molecules, which are comprised of a nitrogenous base, a pentose sugar (in the case of RNA, the sugar is ribose; in the case of DNA, the sugar is D-deoxyribose), and phosphoric acid. The language "nucleoside" includes molecules which serve as precursors to nucleotides, but which are lacking the phosphoric acid moiety that nucleotides possess. By inhibiting the biosynthesis of these molecules, or their mobilization to form nucleic acid molecules, it is possible to inhibit RNA and DNA synthesis; by inhibiting this activity in a fashion targeted to cancerous cells, the ability of tumor cells to divide and replicate may be inhibited. Additionally, there are nucleotides which do not form nucleic acid molecules, but rather serve as energy stores (i.e., AMP) or as coenzymes (i.e., FAD and NAD).

Several publications have described the use of these chemicals for these medical indications, by influencing purine and/or pyrimidine metabolism (e.g. Christopherson, R. I. and Lyons, S. D. (1990) "Potent inhibitors of de novo pyrimidine and purine biosynthesis as chemotherapeutic agents." *Med. Res. Reviews* 10:505-548). Studies of enzymes involved in purine and pyrimidine metabolism have been focused on the development of new drugs which can be used, for example, as immunosuppressants or anti-proliferants (Smith, J. L., (1995) "Enzymes in nucleotide synthesis." *Curr. Opin. Struct. Biol.* 5:752-757; (1995) *Biochem Soc. Transact.* 23:877-902). However, purine and pyrimidine bases, nucleosides and nucleotides have other utilities: as intermediates in the biosynthesis of several fine chemicals (e.g., thiamine, S-adenosyl-methionine, folates, or riboflavin), as energy carriers for the cell (e.g., ATP or GTP), and for chemicals themselves, commonly used as flavor enhancers (e.g., IMP or GMP) or for several medicinal applications (see, for example, Kuninaka, A. (1996) Nucleotides and Related Compounds in Biotechnology vol. 6, Rehm et al., eds. VCH: Weinheim, p. 561-612). Also, enzymes involved in purine, pyrimidine, nucleoside, or nucleotide metabolism are increasingly serving as targets against which chemicals for crop protection, including fungicides, herbicides and insecticides, are developed.

The metabolism of these compounds in bacteria has been characterized (for reviews see, for example, Zalkin, H. and Dixon, J. E. (1992) "de novo purine nucleotide biosynthesis", in: Progress in Nucleic Acid Research and Molecular Biology, vol. 42, Academic Press: p. 259-287; and Michal, G. (1999) "Nucleotides and Nucleosides", Chapter 8 in: Biochemical Pathways: An Atlas of Biochemistry and Molecular Biology, Wiley: New York). Purine metabolism has been the subject of intensive research, and is essential to the normal functioning of the cell. Impaired purine metabolism in higher animals can cause severe disease, such as gout. Purine nucleotides are synthesized from ribose-5-phosphate, in a series of steps through the intermediate compound inosine-5'-phosphate (IMP), resulting in the production of guanosine-5'-monophosphate (GMP) or adenosine-5'-monophosphate (AMP), from which the triphosphate forms utilized as nucleotides are readily formed. These compounds are also utilized as energy stores, so their degradation provides energy for many different biochemical processes in the cell. Pyrimidine biosynthesis proceeds by the formation of uridine-5'-monophosphate (UMP) from ribose-5-phosphate. UMP, in turn, is converted to cytidine-5'-triphosphate (CTP). The deoxy-forms of all of these nucleotides are produced in a one step reduction reaction from the diphosphate ribose form of the nucleotide to the diphosphate deoxyribose form of the nucleotide. Upon phosphorylation, these molecules are able to participate in DNA synthesis.

Trehalose Metabolism and Uses

Trehalose consists of two glucose molecules, bound in α,α-1,1 linkage. It is commonly used in the food industry as a sweetener, an additive for dried or frozen foods, and in beverages. However, it also has applications in the pharmaceutical, cosmetics and biotechnology industries (see, for example, Nishimoto et al., (1998) U.S. Pat. No. 5,759,610; Singer, M. A. and Lindquist, S. (1998) *Trends Biotech.* 16: 460-467; Paiva, C. L. A. and Panek, A. D. (1996) *Biotech. Ann. Rev,* 2: 293-314; and Shiosaka, M. (1997) J. Japan 172: 97-102). Trehalose is produced by enzymes from many microorganisms and is naturally released into the surrounding medium, from which it can be collected using methods known in the art.

I. Recombinant Microorganisms and Methods for Culturing Microorganisms Such that a Fine Chemical is Produced The methodologies of the present invention feature microorganisms, e.g., recombinant microorganisms, preferably including vectors or genes (e.g., wild-type and/or mutated genes) as described herein and/or cultured in a manner which results in the production of a desired fine chemical, e.g. lysine. The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived. Preferably, a "recombinant" microorganism of the present invention has been genetically engineered such that it overexpresses at least one bacterial gene or gene product as described herein, preferably a biosynthetic enzyme encoding-gene, e.g., fructose-1,6-bisphosphatase, included within a recombinant vector as described herein and/or a biosynthetic enzyme, e.g., fructose-1,6-bisphosphatase expressed from a recombinant vector. The ordinary skilled will appreciate that a microorganism expressing or overexpressing a gene product produces or overproduces the gene product as a result of expression or overexpression of nucleic acid sequences and/or genes encoding the gene product. In one embodiment, the recombinant microorganism has increased biosynthetic enzyme, e.g., fructose-1,6-bisphosphatase, activity.

In certain embodiments of the present invention, at least one gene or protein may be deregulated, in addition to the fructose-1,6,-bisphosphatase gene or enzyme, so as to enhance the production of L-amino acids. For example, a gene or an enzyme of the biosynthesis pathways, for example, of glycolysis, of anaplerosis, of the citric acid cycle, of the pentose phosphate cycle, or of amino acids export may be deregulated. Additionally, a regulatory gene or protein may be deregulated.

In various embodiments, expression of a gene may be increased so as to increase the intracellular activity or concentration of the protein encoded by the gene, thereby ultimately improving the production of the desired amino acid. One skilled in the art may use various techniques to achieve the desired result. For example, a skilled practitioner may increase the number of copies of the gene or genes, use a potent promoter, and/or use a gene or allele which codes for the corresponding enzyme having high activity. Using the methods of the present invention, for example, overexpressing a particular gene, the activity or concentration of the corresponding protein can be increased by at least about 10%, 25%, 50%, 75%, 100%, 150%, 200%, 300%, 400%, 500%, 1000% or 2000%, based on the starting activity or concentration.

In various embodiments, the deregulated gene may include, but is not limited to, at least one of the following genes or proteins:

the ask gene which encodes a feed-back resistant aspartokinase (as disclosed in International Publication No. WO2004069996);

the dapA gene which encodes dihydrodipicolinate synthase (as disclosed in SEQ ID NOs:55 and 56, respectively, in International Publication No. WO200100843);

the asd gene which encodes an aspartate semialdehyde dehydrogenase (as disclosed in SEQ ID NOs:3435 and 6935, respectively, in European Publication No. 1108790);

the dapB gene which encodes a dihydrodipicolinate reductase (as disclosed in SEQ ID NOs:35 and 36, respectively, in International Publication No. WO200100843);

the ddh gene which encodes a diaminopimelate dehydrogenase (as disclosed in SEQ ID NOs:3444 and 6944, respectively, in European Publication No. 1108790);

the lysA gene which encodes a diaminopimelate epimerase (as disclosed in SEQ ID NOs:3451 and 6951, respectively, in European Publication No. 1108790);

the lysE gene which encodes a lysine exporter (as disclosed in SEQ ID NOs:3455 and 6955, respectively, in European Publication No. 1108790);

the pycA gene which encodes a pyruvate carboxylase (as disclosed in SEQ ID NOs:765 and 4265, respectively, in European Publication No. 1108790);

the zwf gene which encodes a glucose-6-phosphate dehydrogenase (as disclosed in SEQ ID NOs: 243 and 244, respectively, in International Publication No. WO200100844);

the pepCL gene which encodes a phosphoenolpyruvate carboxylase (as disclosed in SEQ ID NOs:3470 and 6970, respectively, in European Publication No. 1108790);

the gap gene which encodes a glyceraldedyde-3-phosphate dehydrogenase (as disclosed in SEQ ID NOs: 67 and 68, respectively, in International Publication No. WO200100844);

the zwa1 gene which encodes an RPF protein precursor (as disclosed in SEQ ID NOs:917 and 4417, respectively, in European Publication No. 1108790);

the tkt gene which encodes a transketolase (as disclosed in SEQ ID NOs: 247 and 248, respectively, in International Publication No. WO200100844);

the tad gene which encodes a transaldolase (as disclosed in SEQ ID NOs: 245 and 246, respectively, in International Publication No. WO200100844);

the mqo gene which codes for a menaquinine oxidoreductase (as disclosed in SEQ ID NOs: 569 and 570, respectively, in International Publication No. WO200100844);

the tpi gene which codes for a triosephosphate isomerase (as disclosed in SEQ ID NOs: 61 and 62, respectively, in International Publication No. WO200100844);

the pgk gene which codes for a 3-phosphoglycerate kinase (as disclosed in SEQ ID NOs:69 and 70, respectively, in International Publication No. WO200100844); and the sigC gene which codes for an RNA-polymerase sigma factor sigC (as disclosed in SEQ ID NOs:284 and 3784, respectively, in European Publication No. 1108790).

In particular embodiments, the gene may be overexpressed and/or the activity of the protein may be increased.

Alternatively, in other embodiments, expression of a gene may be attenuated, decreased or repressed so as to decrease, for example, eliminate, the intracellular activity or concentration of the protein encoded by the gene, thereby ultimately improving the production of the desired amino acid. For example, one skilled in the art may use a weak promoter. Alternatively or in combination, a skilled practitioner may use a gene or allele that either codes for the corresponding enzyme having low activity or inactivates the corresponding gene or enzyme. Using the methods of the present invention, the activity or concentration of the corresponding protein can be reduced to about 0 to 50%, 0 to 25%, 0 to 10%, 0 to 9%, 0 to 8%, 0 to 7%, 0 to 6%, 0 to 5%, 0 to 4%, 0 to 3%, 0 to 2% or 0 to 1% of the activity or concentration of the wild-type protein.

In certain embodiments, the deregulated gene may include, but is not limited to, at least one of the following genes or proteins:

the pepCK gene which codes for the phosphoenolpyruvate carboxykinase (as disclosed in SEQ ID NOs: 179 and 180, respectively, in International Publication No. WO200100844);

the mal E gene which codes for the malic enzyme (as disclosed in SEQ ID NOs:3328 and 6828, respectively, in European Publication No. 1108790);

the glgA gene which codes for the glycogen synthase (as disclosed in SEQ ID NOs:1239 and 4739, respectively, in European Publication No. 1108790);

the pgi gene which codes for the glucose-6-phosphate isomerase (as disclosed in SEQ ID NOs: 41 and 42, respectively, in International Publication No. WO200100844);

the dead gene which codes for the ATP dependent RNA helicase (as disclosed in SEQ ID NOs:1278 and 4778, respectively, in European Publication No. 1108790);

the menE gene which codes for the o-succinylbenzoic acid-CoA ligase (as disclosed in SEQ ID NOs:505 and 4005, respectively, in European Publication No. 1108790);

the citE gene which codes for the citrate lyase beta chain (as disclosed in SEQ ID NOs: 547 and 548, respectively, in International Publication No. WO200100844);

the mikE17 gene which codes for a transcriptional regulator (as disclosed in SEQ ID NOs:411 and 3911, respectively, in European Publication No. 1108790);

the poxB gene which codes for the pyruvate dehydrogenase (as disclosed in SEQ ID NOs: 85 and 86, respectively, in International Publication No. WO200100844);

the zwa2 gene which codes for an RPF protein precursor (as disclosed in European Publication No. 1106693); and the sucC gene which codes for the Succinyl-CoA-Synthetase (as disclosed in European Publication No. 1103611).

In particular embodiments, the expression of the gene may be attenuated, decreased or repressed and/or the activity of the protein may be decreased.

The term "manipulated microorganism" includes a microorganism that has been engineered (e.g., genetically engineered) or modified such that results in the disruption or alteration of a metabolic pathway so as to cause a change in the metabolism of carbon. An enzyme is "overexpressed" in a metabolically engineered cell when the enzyme is expressed in the metabolically engineered cell at a level higher than the level at which it is expressed in a comparable wild-type cell. In cells that do not endogenously express a particular enzyme, any level of expression of that enzyme in the cell is deemed an "overexpression" of that enzyme for purposes of the present invention. Overexpression may lead to increased activity of the protein encoded by the gene, e.g., fructose-1,6-bisphosphatase.

Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, e.g., has increased activity, for example, as compared to a corresponding wild-type or naturally occurring enzyme.

The term "overexpressed" or "overexpression" includes expression of a gene product (e.g., a pentose phosphate biosynthetic enzyme) at a level greater than that expressed prior to manipulation of the microorganism or in a comparable microorganism which has not been manipulated. In one embodiment, the microorganism can be genetically manipulated (e.g., genetically engineered) to overexpress a level of gene product greater than that expressed prior to manipulation of the microorganism or in a comparable microorganism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

The term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased, thereby enhancing or increasing the activity of the gene product. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a microorganism arises from the particular phenomenon of microorganisms in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" microorganism of the present invention has been genetically engineered to overexpress a bacterially-derived gene or gene product. The term "bacterially-derived" or "derived-from", for example bacteria, includes a gene which is naturally found in bacteria or a gene product which is encoded by a bacterial gene (e.g., encoded by fructose-1,6-bisphosphatase).

The methodologies of the present invention feature recombinant microorganisms which overexpress one or more genes, e.g., the fructose-1,6-bisphosphatase gene or have increased or enhanced the fructose-1,6-bisphosphatase activity. A particularly preferred recombinant microorganism of the present invention (e.g., *Corynebacterium glutamicium*, *Corynebacterium acetoglutamicum*, *Corynebacterium acetoacidophilum*, and *Corynebacterium thermoaminogenes*, etc.) has been genetically engineered to overexpress a biosynthetic enzyme (e.g., fructose-1,6-bisphosphatase, the amino acid sequence of SEQ ID NO:2 or encoded by the nucleic acid sequence of SEQ ID NO:1).

Other preferred "recombinant" microorganisms of the present invention have an enzyme deregulated in the pentose phosphate pathway. The phrase "microorganism having a deregulated pentose phosphate pathway" includes a microorganism having an alteration or modification in at least one gene encoding an enzyme of the pentose phosphate pathway or having an alteration or modification in an operon including more than one gene encoding an enzyme of the pentose phosphate pathway. A preferred "microorganism having a deregulated pentose phosphate pathway" has been genetically engineered to overexpress a *Corynebacterium* (e.g., *C. glutamicium*) biosynthetic enzyme (e.g., has been engineered to overexpress fructose-1,6-bisphosphatase).

In another preferred embodiment, a recombinant microorganism is designed or engineered such that one or more pentose phosphate biosynthetic enzyme is overexpressed or deregulated.

In another preferred embodiment, a microorganism of the present invention overexpresses or is mutated for a gene or biosynthetic enzyme (e.g., a pentose phosphate biosynthetic enzyme) which is bacterially-derived. The term "bacterially-derived" or "derived-from", for example bacteria, includes a gene product (e.g., fructose-1,6-bisphosphatase) which is encoded by a bacterial gene.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Bacillus, Brevibacterium, Cornyebacterium, Lactobacillus, Lactococci* and *Streptomyces*. In a more preferred embodiment, the recombinant microorganism is of the genus *Cornyebacterium*. In another preferred embodiment, the recombinant microorganism is selected from the group consisting of *Cornynebacterium glutamicium, Corynebacterium acetoglutamicum, Corynebacterium acetoacidophilum* or *Corynebacterium thermoaminogenes*. In a particularly preferred embodiment, the recombinant microorganism is *Corynebacterium glutamicium*.

An important aspect of the present invention involves culturing the recombinant microorganisms described herein, such that a desired compound (e.g., a desired fine chemical) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism. Carbon sources which may be used include sugars and carbohydrates, such as for example glucose, sucrose, lactose, fructose, maltose, molasses, starch and cellulose, oils and fats, such as for example soy oil, sunflower oil, peanut oil and coconut oil, fatty acids, such as for example palmitic acid, stearic acid and linoleic acid, alcohols, such as for example glycerol and ethanol, and organic acids, such as for example acetic acid. In a preferred embodiment, fructose or saccharose. These substances may be used individually or as a mixture.

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Preferably, microorganisms of the present invention are cultured under controlled pH. The term "controlled pH" includes any pH which results in production of the desired fine chemical, e.g., lysine. In one embodiment, microorganisms are cultured at a pH of about 7. In another embodiment, microorganisms are cultured at a pH of between 6.0 and 8.5. The desired pH may be maintained by any number of methods known to those skilled in the art. For example, basic compounds such as sodium hydroxide, potassium hydroxide, ammonia, or ammonia water, or acidic compounds, such as phosphoric acid or sulfuric acid, are used to appropriately control the pH of the culture.

Also preferably, microorganisms of the present invention are cultured under controlled aeration. The term "controlled aeration" includes sufficient aeration (e.g., oxygen) to result in production of the desired fine chemical, e.g., lysine. In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents such as fatty acid poly glycol esters).

Moreover, microorganisms of the present invention can be cultured under controlled temperatures. The term "controlled temperature" includes any temperature which results in production of the desired fine chemical, e.g., lysine. In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired fine chemical, e.g., lysine. A variety of such processes have been developed and are well-known in the art.

The phrase "culturing under conditions such that a desired fine chemical, e.g., lysine is produced" includes maintaining and/or growing microorganisms under conditions (e.g., temperature, pressure, pH, duration, etc.) appropriate or sufficient to obtain production of the desired fine chemical or to obtain desired yields of the particular fine chemical, e.g., lysine, being produced. For example, culturing is continued for a time sufficient to produce the desired amount of a fine chemical (e.g., lysine). Preferably, culturing is continued for a time sufficient to substantially reach maximal production of the fine chemical. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of a fine chemical, for example, cells are cultured such that at least about 15 to 20 g/L of a fine chemical are produced, at least about 20 to 25 g/L of a fine chemical are produced, at least about 25 to 30 g/L of a fine chemical are produced, at least about 30 to 35 g/L of a fine chemical are produced, at least about 35 to 40 g/L of a fine chemical are produced, at least about 40 to 50 g/L of a fine chemical are produced, at least about 50 to 60 g/L of a fine chemical are produced, at least about 60 to 70 g/L of a fine chemical are produced, at least about 70 to 80 g/L of a fine chemical are produced, at least about 80 to 90 g/L of a fine chemical are produced, at least about 90 to 100 g/L of a fine chemical are produced, at least about 100 to 110 g/L of a fine chemical are produced, at least about 110 to 120 g/L of a fine chemical are produced, at least about 120 to 130 g/L of a fine chemical are produced, at least about 130 to 140 g/L of a fine chemical are produced, or at least about 140 to 160 g/L of a fine chemical are produced In yet another embodiment, microorganisms are cultured under conditions such that a preferred yield of a fine chemical, for example, a yield within a range set forth above, is produced in about 24 hours, in about 36 hours, in about 40 hours, in about 48 hours, in about 72 hours, in about 96 hours, in about 108 hours, in about 122 hours, or in about 144 hours.

The methodology of the present invention can further include a step of recovering a desired fine chemical, e.g., lysine. The term "recovering" a desired fine chemical, e.g., lysine includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a fine chemical, e.g., lysine, can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the fine chemical of interest (e.g., lysine).

Preferably, a desired fine chemical of the present invention is "extracted", "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts).

In an alternative embodiment, the desired fine chemical, e.g., lysine, is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) supernatant is used without modification. In another embodiment, the culture (or culture supernatant) is concentrated. In yet another embodiment, the culture (or culture supernatant) is dried or lyophilized.

II. Methods of Producing a Fine Chemical Independent of Precursor Feed Requirements Depending on the biosynthetic enzyme or combination of biosynthetic enzymes manipulated, it may be desirable or necessary to provide (e.g., feed) microorganisms of the present invention at least one pentose phosphase pathway biosynthetic precursor such that fine chemicals, e.g., lysine, are produced. The term "pentose phosphase pathway biosynthetic precursor" or "precursor" includes an agent or compound which, when provided to, brought into contact with, or included in the culture medium of a microorganism, serves to enhance or increase pentose phosphate biosynthesis. In one embodiment, the pentose phosphate biosynthetic precursor or precursor is glucose. In another embodiment, the pentose phosphate biosynthetic precursor is fructose. The amount of glucose or fructose added is preferably an amount that results in a concentration in the culture medium sufficient to enhance productivity of the microorganism (e.g., a concentration sufficient to enhance production of a fine chemical e.g., lysine). Pentose phosphate biosynthetic precursors of the present invention can be added in the form of a concentrated solution or suspension (e.g., in a suitable solvent such as water or buffer) or in the form of a solid (e.g., in the form of a powder). Moreover, pentose phosphate biosynthetic precursors of the present invention can be added as a single aliquot, continuously or intermittently over a given period of time.

Providing pentose phosphate biosynthetic precursors in the pentose phosphate biosynthetic methodologies of the present invention, can be associated with high costs, for example, when the methodologies are used to produce high yields of a fine chemical. Accordingly, preferred methodologies of the present invention feature microorganisms having at least one biosynthetic enzyme or combination of biosynthetic enzymes (e.g., at least one pentose phosphate biosynthetic enzyme) manipulated such that lysine or other desired fine chemicals are produced in a manner independent of precursor feed. The phrase "a manner independent of precursor feed", for example, when referring to a method for producing a desired compound includes an approach to or a mode of producing the desired compound that does not depend or rely on precursors being provided (e.g., fed) to the microorganism being utilized to produce the desired compound. For example, microorganisms featured in the methodologies of the present invention can be used to produce fine chemicals in a manner requiring no feeding of the precursors glucose or fructose.

Alternative preferred methodologies of the present invention feature microorganisms having at least one biosynthetic enzyme or combination of biosynthetic enzymes manipulated such that L-Lysine or other fine chemicals are produced in a manner substantially independent of precursor feed. The phrase "a manner substantially independent of precursor feed" includes an approach to or a method of producing the desired compound that depends or relies to a lesser extent on precursors being provided (e.g., fed) to the microorganism being utilized. For example, microorganisms featured in the methodologies of the present invention can be used to produce fine chemicals in a manner requiring feeding of substantially reduced amounts of the precursors glucose or fructose.

Preferred methods of producing desired fine chemicals in a manner independent of precursor feed or alternatively, in a manner substantially independent of precursor feed, involve culturing microorganisms which have been manipulated (e.g., designed or engineered, for example, genetically engineered) such that expression of at least one pentose phosphate biosynthetic enzyme is modified. For example, in one embodiment, a microorganism is manipulated (e.g., designed or engineered) such that the production of at least one pentose phosphate biosynthetic enzyme is deregulated. In a preferred embodiment, a microorganism is manipulated (e.g., designed or engineered) such that it has a deregulated biosynthetic pathway, for example, a deregulated pentose phosphate biosynthesis pathway, as defined herein. In another preferred embodiment, a microorganism is manipulated (e.g., designed or engineered) such that at least one pentose phosphate biosynthetic enzyme, e.g., fructose-1,6-bisphosphatase is overexpressed.

III. High Yield Production Methodologies

A particularly preferred embodiment of the present invention is a high yield production method for producing a fine chemical, e.g., lysine, comprising culturing a manipulated microorganism under conditions such that lysine is produced at a significantly high yield. The phrase "high yield production method", for example, a high yield production method for producing a desired fine chemical, e.g., lysine, includes a method that results in production of the desired fine chemical at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing lysine that includes culturing a manipulated microorganism under conditions such that lysine is produced at a level greater than 2 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 110 g/L, 120 g/L, 130 g/L, 140 g/L, 150 g/L, 160 g/L, 170 g/L, 180 g/L, 190 g/L, or 200 g/L.

The invention further features a high yield production method for producing a desired fine chemical, e.g., lysine, that involves culturing a manipulated microorganism under conditions such that a sufficiently elevated level of compound is produced within a commercially desirable period of time. In an exemplary embodiment, the invention features a high yield production method of producing lysine that includes culturing a manipulated microorganism under conditions such that lysine is produced at a level greater than 15-20 g/L in 5 hours. In another embodiment, the invention features a high yield production method of producing lysine that includes culturing a manipulated microorganism under conditions such that lysine is produced at a level greater than 25-40 g/L in 10 hours. In another embodiment, the invention features a high yield production method of producing lysine that includes culturing a manipulated microorganism under conditions such that lysine is produced at a level greater than 50-100 g/L in 20 hours. In another embodiment, the invention features a high yield production method of producing lysine that includes culturing a manipulated microorganism under conditions such that lysine is produced at a level greater than 140-160 g/L in 40 hours, for example, greater than 150 g/L in 40 hours. In another embodiment, the invention features a high yield production method of producing lysine that includes culturing a manipulated microorganism under conditions such that lysine is produced at a level greater than 130-160 g/L in 40 hours, for example, greater than 135, 145 or 150 g/L in 40 hours. Values and ranges included and/or intermediate within the ranges set forth herein are also intended to be within the scope of the present invention. For example, lysine production at levels of at least 140, 141, 142, 143, 144, 145, 146, 147, 148, 149, and 150 g/L in 40 hours are intended to be included within the range of 140-150 g/L in 40 hours. In another example, ranges of 140-145 g/L or 145-150 g/L are intended to be included within the range of 140-150 g/L in 40 hours. Moreover, the skilled artisan will appreciate that culturing a manipulated microorganism to achieve a production level of, for example, "140-150 g/L in 40 hours" includes culturing the microorganism for additional time periods (e.g., time periods longer than 40 hours), optionally resulting in even higher yields of lysine being produced.

IV. Isolated Nucleic Acid Molecules and Genes

Another aspect of the present invention features isolated nucleic acid molecules that encode proteins (e.g., *C. glutamicium* proteins), for example, *Corynebacterium* pentose phosphate biosynthetic enzymes (e.g., *C. glutamicum* pentose phosphate enzymes) for use in the methods of the invention. In one embodiment, the isolated nucleic acid molecules used in the methods of the invention are fructose-1,6-bisphosphatase nucleic acid molecules.

The term "nucleic acid molecule" includes DNA molecules (e.g., linear, circular, cDNA or chromosomal DNA) and RNA molecules (e.g., tRNA, rRNA, mRNA) and analogs of the DNA or RNA generated using nucleotide analogs. The nucleic acid molecule can be single-stranded or double-stranded, but preferably is double-stranded DNA. The term "isolated" nucleic acid molecule includes a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

The term "gene," as used herein, includes a nucleic acid molecule (e.g., a DNA molecule or segment thereof), for example, a protein or RNA-encoding nucleic acid molecule, that in an organism, is separated from another gene or other genes, by intergenic DNA (i.e., intervening or spacer DNA which naturally flanks the gene and/or separates genes in the chromosomal DNA of the organism). A gene may direct synthesis of an enzyme or other protein molecule (e.g., may comprise coding sequences, for example, a contiguous open reading frame (ORF) which encodes a protein) or may itself be functional in the organism. A gene in an organism, may be clustered in an operon, as defined herein, said operon being separated from other genes and/or operons by the intergenic DNA. Individual genes contained within an operon may overlap without intergenic DNA between said individual genes. An "isolated gene", as used herein, includes a gene which is essentially free of sequences which naturally flank the gene in the chromosomal DNA of the organism from which the gene is derived (i.e., is free of adjacent coding sequences which encode a second or distinct protein or RNA molecule, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode *Corynebacterium* proteins). In another embodiment, an isolated gene includes coding sequences for a protein (e.g., for a *Corynebacterium* protein) and adjacent 5' and/or 3' regulatory sequences from the chromosomal DNA of the organism from which the gene is derived (e.g., adjacent 5' and/or 3' *Corynebacterium* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

In one aspect, the methods of the present invention features use of isolated fructose-1,6-bisphosphatate nucleic acid sequences or genes.

In a preferred embodiment, the nucleic acid or gene is derived from *Bacillus* (e.g., is *Corynebacterium*-derived). The term "derived from *Corynebacterium*" or "*Corynebacterium*-derived" includes a nucleic acid or gene which is naturally found in microorganisms of the genus *Corynebacterium*. Preferably, the nucleic acid or gene is derived from a microorganism selected from the group consisting of *Cornynebacterium glutamicium, Corynebacterium acetoglutamicum, Corynebacterium acetoacidophilum* or *Corynebacterium thermoaminogenes*. In a particularly preferred embodiment, the nucleic acid or gene is derived from *Cornynebacterium glutamicium* (e.g., is *Cornynebacterium glutamicium*-derived). In yet another preferred embodiment, the nucleic acid or gene is a *Cornynebacterium* gene homologue (e.g., is derived from a species distinct from *Cornynebacterium* but having significant homology to a *Cornynebacterium* gene of the present invention, for example, a *Cornynebacterium* fructose-1,6-bisphosphatase gene).

Included within the scope of the present invention are bacterial-derived nucleic acid molecules or genes and/or *Cornynebacterium*-derived nucleic acid molecules or genes (e.g., *Cornynebacterium*-derived nucleic acid molecules or genes), for example, the genes identified by the present inventors, for example, *Cornynebacterium* or *C. glutamicium* fructose-1,6-bisphosphatase genes. Further included within the scope of the present invention are bacterial-derived nucleic acid molecules or genes and/or *Cornynebacterium*-derived nucleic acid molecules or genes (e.g., *C. glutamicium*-derived nucleic acid molecules or genes) (e.g., *C. glutamicium* nucleic acid molecules or genes) which differ from naturally-occurring bacterial and/or *Cornynebacterium* nucleic acid molecules or genes (e.g., *C. glutamicium* nucleic acid molecules or genes), for example, nucleic acid molecules or genes which have nucleic acids that are substituted, inserted or deleted, but which encode proteins substantially similar to the naturally-occurring gene products of the present invention. In one embodiment, an isolated nucleic acid molecule comprises the nucleotide sequences set forth as SEQ ID NO:1, or encodes the amino acid sequence set forth in SEQ ID NO:2.

In another embodiment, an isolated nucleic acid molecule of the present invention comprises a nucleotide sequence which is at least about 60-65%, preferably at least about 70-75%, more preferable at least about 80-85%, and even more preferably at least about 90-95% or more identical to a nucleotide sequence set forth as SEQ ID NO:1. In another embodiment, an isolated nucleic acid molecule hybridizes under stringent conditions to a nucleic acid molecule having a nucleotide sequence set forth as SEQ ID NO:1. Such stringent conditions are known to those skilled in the art and can be found in *Current Protocols in Molecular Biology*, John Wiley & Sons, N.Y. (1989), 6.3.1-6.3.6. A preferred, non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature.

A nucleic acid molecule of the present invention (e.g., a nucleic acid molecule having the nucleotide sequence of SEQ ID NO: lean be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the sequence of SEQ ID NO:1. A nucleic acid of the invention can be amplified using cDNA, mRNA or alternatively, genomic DNA, as a template and appropriate oligonucleotide primers according to standard PCR amplification techniques. In another preferred embodiment, an isolated nucleic acid molecule of the invention comprises a nucleic acid molecule which is a complement of the nucleotide sequence shown in SEQ ID NO:1.

In another embodiment, an isolated nucleic acid molecule is or includes a fructose-1,6-bisphosphatase gene, or portion or fragment thereof. In one embodiment, an isolated fructose-1,6-bisphosphatase nucleic acid molecule or gene comprises the nucleotide sequence as set forth in SEQ ID NO:1 (e.g., comprises the *C. glutamicum* fructose-1,6-bisphosphatase nucleotide sequence). In another embodiment, an isolated fructose-1,6-bisphosphatase nucleic acid molecule or gene comprises a nucleotide sequence that encodes the amino acid sequence as set forth in SEQ ID NO:2 (e.g., encodes the *C. glutamicum* fructose-1,6-bisphosphatase amino acid sequence). In yet another embodiment, an isolated fructose-1,6-bisphosphatase nucleic acid molecule or gene encodes a homologue of the fructose-1,6-bisphosphatase protein having the amino acid sequence of SEQ ID NO:2. As used herein, the term "homologue" includes a protein or polypeptide sharing at least about 30-35%, preferably at least about 35-40%, more preferably at least about 40-50%, and even more preferably at least about 60%, 70%, 80%, 90% or more identity with the amino acid sequence of a wild-type protein or polypeptide described herein and having a substantially equivalent functional or biological activity as said wild-type protein or polypeptide. For example, a fructose-1,6-bisphosphatase homologue shares at least about 30-35%, preferably at least about 35-40%, more preferably at least about 40-50%, and even more preferably at least about 60%, 70%, 80%, 90% or more identity with the protein having the amino acid sequence set forth as SEQ ID NO:2 and has a substantially equivalent functional or biological activity (i.e., is a functional equivalent) of the protein having the amino acid sequence set forth as SEQ ID NO:2 (e.g., has a substantially equivalent pantothenate kinase activity). In a preferred embodiment, an isolated fructose-1,6-bisphosphatase nucleic acid molecule or gene comprises a nucleotide sequence that encodes a polypeptide as set forth in SEQ ID NO:2. In another embodiment, an isolated fructose-1,6-bisphosphatase nucleic acid molecule hybridizes to all or a portion of a nucleic acid molecule having the nucleotide sequence set forth in SEQ ID NO:1 or hybridizes to all or a portion of a nucleic acid molecule having a nucleotide sequence that encodes a polypeptide having the amino acid sequence of SEQ ID NOs:2. Such hybridization conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50%) formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or, alternatively, 0.2×SSC, 1% SDS). In another preferred embodiment, an isolated nucleic acid molecule comprises a nucleotide sequence that is complementary to a fructose-1,6-bisphosphatase nucleotide sequence as set forth herein (e.g., is the full complement of the nucleotide sequence set forth as SEQ ID NO:1).

A nucleic acid molecule of the present invention (e.g., a fructose-1,6-bisphosphatase nucleic acid molecule or gene), can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the fructose-1,6-bisphosphatase nucleotide sequences set forth herein, or flanking sequences thereof. A nucleic acid of the invention (e.g., a fructose-1,6-bisphosphatase nucleic acid molecule or gene), can be amplified using cDNA, mRNA or alternatively, chromosomal DNA, as a template and appropriate oligonucleotide primers according to standard PCR amplification techniques.

Yet another embodiment of the present invention features mutant fructose-1,6-bisphosphatase nucleic acid molecules or genes. The phrase "mutant nucleic acid molecule" or "mutant gene" as used herein, includes a nucleic acid molecule or gene having a nucleotide sequence which includes at least one alteration (e.g., substitution, insertion, deletion) such that the polypeptide or protein that may be encoded by said mutant exhibits an activity that differs from the polypeptide or protein encoded by the wild-type nucleic acid molecule or gene. Preferably, a mutant nucleic acid molecule or mutant gene (e.g., a mutant fructose-1,6-bisphosphatase gene) encodes a polypeptide or protein having an increased activity (e.g., having an increased fructose-1,6-bisphosphatase activity) as compared to the polypeptide or protein encoded by the wild-type nucleic acid molecule or gene, for example, when assayed under similar conditions (e.g., assayed in microorganisms cultured at the same temperature). A mutant gene also can have an increased level of production of the wild-type polypeptide.

As used herein, an "increased or enhanced activity" or "increased or enhanced enzymatic activity" is one that is at least 5% greater than that of the polypeptide or protein encoded by the wild-type nucleic acid molecule or gene, preferably at least 5-10% more, more preferably at least 10-25% more and even more preferably at least 25-50%, 50-75% or 75-100% more than that of the polypeptide or protein encoded by the wild-type nucleic acid molecule or gene. Ranges intermediate to the above-recited values, e.g., 75-85%, 85-90%, 90-95%, are also intended to be encompassed by the present invention. Activity can be determined according to any well accepted assay for measuring activity of a particular protein of interest. Activity can be measured or assayed directly, for example, measuring an activity of a protein isolated or purified from a cell. Alternatively, an activity can be measured or assayed within a cell or in an extracellular medium.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant nucleic acid or mutant gene (e.g., encoding a mutant polypeptide or protein), as defined herein, is readily distinguishable from a nucleic acid or gene encoding a protein homologue, as described above, in that a mutant nucleic acid or mutant gene encodes a protein or polypeptide having an altered activity, optionally observable as a different or distinct phenotype in a microorganism expressing said mutant gene or nucleic acid or producing said mutant protein or polypeptide (i.e., a mutant microorganism) as compared to a corresponding microorganism expressing the wild-type gene or nucleic acid or producing said mutant protein or polypeptide. By contrast, a protein homologue has an identical or substantially similar activity, optionally phenotypically indiscernable when produced in a microorganism, as compared to a corresponding microorganism expressing the wild-type gene or nucleic acid. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30-50% sequence identity) sequence identity yet having substantially equivalent functional activities, and mutants, for example sharing 99% sequence identity yet having dramatically different or altered functional activities.

V. Recombinant Nucleic Acid Molecules and Vectors

The present invention further features recombinant nucleic acid molecules (e.g., recombinant DNA molecules) that include nucleic acid molecules and/or genes described herein (e.g., isolated nucleic acid molecules and/or genes), preferably *Corynebacterium* genes, more preferably *Corynebacterium glutamicum* genes, even more preferably *Corynebacterium glutamicum* fructose-1,6-bisphosphatase genes.

The present invention further features vectors (e.g., recombinant vectors) that include nucleic acid molecules (e.g., isolated or recombinant nucleic acid molecules and/or genes) described herein. In particular, recombinant vectors are featured that include nucleic acid sequences that encode bacterial gene products as described herein, preferably *Corynebacterium* gene products, more preferably *Corynebacterium glutamicum* gene products (e.g., pentose phosphate enzymes, for example, fructose-1,6-bisphosphatase).

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated nucleic acid molecule or gene of the present invention (e.g., an isolated fructose-1,6-bisphosphatase gene) operably linked to regulatory sequences.

The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a fructose-1,6-bisphosphatase gene or recombinant nucleic acid molecule including such fructose-1,6-bisphosphatase gene, operably linked to regulatory sequences, for example, promoter sequences, terminator sequences and/or artificial ribosome binding sites (RBSs).

The phrase "operably linked to regulatory sequence(s)" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences. In one embodiment, a regulatory sequence is included in a recombinant nucleic acid molecule or recombinant vector in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule or recombinant vector operably linked to a regulatory sequence which accompanies or is adjacent to the gene of interest in the natural organism (e.g., operably linked to "native" regulatory sequences, for example, to the "native" promoter). Alternatively, a gene of interest can be included in a recombinant nucleic acid molecule or recombinant vector operably linked to a regulatory sequence which accompanies or is adjacent to another (e.g., a different) gene in the natural organism. Alternatively, a gene of interest can be included in a recombinant nucleic acid molecule or recombinant vector operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule or recombinant vector of the present invention includes a nucleic acid sequence or gene that encodes at least one bacterial gene product (e.g., a pentose phosphate biosynthetic enzyme, for example fructose-1,6-bisphosphatase) operably linked to a promoter or promoter sequence. Preferred promoters of the present invention include *Corynebacterium* promoters and/or bacteriophage promoters (e.g., bacteriophage which infect *Corynebacterium*). In one embodiment, a promoter is a *Corynebacterium* promoter, preferably a strong *Corynebacterium* promoter (e.g., a promoter associated with a biochemical housekeeping gene in *Corynebacterium* or a promoter associated with a glycolytic pathway gene in *Corynebacterium*). In another embodiment, a promoter is a bacteriophage promoter.

In another embodiment, a recombinant nucleic acid molecule or recombinant vector of the present invention includes a terminator sequence or terminator sequences (e.g., transcription terminator sequences). The term "terminator sequences" includes regulatory sequences which serve to terminate transcription of a gene. Terminator sequences (or tandem transcription terminators) can further serve to stabilize mRNA (e.g., by adding structure to mRNA), for example, against nucleases.

In yet another embodiment, a recombinant nucleic acid molecule or recombinant vector of the present invention includes sequences which allow for detection of the vector containing said sequences (i.e., detectable and/or selectable markers), for example, sequences that overcome auxotrophic mutations, for example, ura3 or ilvE, fluorescent markers, and/or colorimetric markers (e.g., lacZ/β-galactosidase), and/or antibiotic resistance genes (e.g., amp or tet).

In yet another embodiment, a recombinant vector of the present invention includes antibiotic resistance genes. The term "antibiotic resistance genes" includes sequences which promote or confer resistance to antibiotics on the host organism (e.g., *Bacillus*). In one embodiment, the antibiotic resistance genes are selected from the group consisting of cat (chloramphenicol resistance) genes, tet (tetracycline resistance) genes, erm (erythromycin resistance) genes, neo (neomycin resistance) genes and spec (spectinomycin resistance) genes. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

It will further be appreciated by one of skill in the art that the design of a vector can be tailored depending on such factors as the choice of microorganism to be genetically engineered, the level of expression of gene product desired and the like.

VI. Isolated Proteins

Another aspect of the present invention features isolated proteins (e.g., isolated pentose phosphate biosynthetic enzymes, for example isolated fructose-1,6-bisphosphatase). In one embodiment, proteins (e.g., isolated pentose phosphate enzymes, for example isolated fructose-1,6-bisphosphatase) are produced by recombinant DNA techniques and can be isolated from microorganisms of the present invention by an appropriate purification scheme using standard protein purification techniques. In another embodiment, proteins are synthesized chemically using standard peptide synthesis techniques.

An "isolated" or "purified" protein (e.g., an isolated or purified biosynthetic enzyme) is substantially free of cellular material or other contaminating proteins from the microorganism from which the protein is derived, or substantially free from chemical precursors or other chemicals when chemically synthesized. In one embodiment, an isolated or purified protein has less than about 30% (by dry weight) of contaminating protein or chemicals, more preferably less than about 20% of contaminating protein or chemicals, still more preferably less than about 10% of contaminating protein or chemicals, and most preferably less than about 5% contaminating protein or chemicals.

In a preferred embodiment, the protein or gene product is derived from *Cornynebacterium* (e.g., is *Cornynebacterium*-derived). The term "derived from *Cornynebacterium*" or "*Cornynebacterium*-derived" includes a protein or gene product which is encoded by a *Cornynebacterium* gene. Preferably, the gene product is derived from a microorganism selected from the group consisting of *Cornynebacterium glutamicium, Cornynebacterium acetoglutamicum, Cornybacterium acetoacidophilum* or *Cornynebacterium thermoaminogenes*. In a particularly preferred embodiment, the protein or gene product is derived from *Cornynebacterium glutamicium* (e.g., is *Cornynebacterium glutamicium*-derived). The term "derived from *Corynebacterium glutamicium*" or "*Corynebacterium glutamicium*-derived" includes a protein or gene product which is encoded by a *Corynebacterium glutamicium* gene. In yet another preferred embodiment, the protein or gene product is encoded by a *Corynebacterium* gene homologue (e.g., a gene derived from a species distinct from *Corynebacterium* but having significant homology to a *Corynebacterium* gene of the present invention, for example, a *Corynebacterium* fructose-1,6-bisphosphatase gene).

Included within the scope of the present invention are bacterial-derived proteins or gene products and/or *Corynebacterium*-derived proteins or gene products (e.g., *C. glutamicium*-derived gene products) that are encoded by naturally-occurring bacterial and/or *Corynebacterium* genes (e.g., *C. glutamicium* genes), for example, the genes identified by the present inventors, for example, *Corynebacterium* or *C. glutamicium* fructose-1,6-bisphosphatase genes. Further included within the scope of the present invention are bacterial-derived proteins or gene products and/or *Corynebacterium*-derived proteins or gene products (e.g., *C. glutamicium*-derived gene products) that are encoded bacterial and/or *Corynebacterium* genes (e.g., *C. glutamicium* genes) which differ from naturally-occurring bacterial and/or *Corynebacterium* genes (e.g., *C. glutamicium* genes), for example, genes which have nucleic acids that are mutated, inserted or deleted, but which encode proteins substantially similar to the naturally-occurring gene products of the present invention. For example, it is well understood that one of skill in the art can mutate (e.g., substitute) nucleic acids which, due to the degeneracy of the genetic code, encode for an identical amino acid as that encoded by the naturally-occurring gene. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product as compared with a naturally-occurring gene product, each instance of which is intended to be included within the scope of the present invention.

In a preferred embodiment, an isolated protein of the present invention (e.g., an isolated pentose phosphate biosynthetic enzyme, for example isolated fructose-1,6-bisphosphatase) has an amino acid sequence shown in SEQ ID NO:2. In other embodiments, an isolated protein of the present invention is a homologue of the protein set forth as SEQ ID NO:2, (e.g., comprises an amino acid sequence at least about 30-40% identical, preferably about 40-50% identical, more preferably about 50-60% identical, and even more preferably about 60-70%, 70-80%, 80-90%, 90-95% or more identical to the amino acid sequence of SEQ ID NO:2, and has an activity that is substantially similar to that of the protein encoded by the amino acid sequence of SEQ ID NO:2.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), preferably taking into account the number of gaps and size of said gaps necessary to produce an optimal alignment.

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) *Nucleic Acids Research* 25(17):3389-3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE (http://vega.igh.cnrs.fr) or at the ISREC server (http://www.ch.embnet.org). When utilizing the ALIGN program for comparing amino acid sequences, a PAM120 weight residue table, a gap length penalty of 12, and a gap penalty of 4 can be used.

In another preferred embodiment, the percent homology between two amino acid sequences can be determined using the GAP program in the GCG software package (available at http://www.gcg.com), using either a Blossom 62 matrix or a PAM250 matrix, and a gap weight of 12, 10, 8, 6, or 4 and a length weight of 2, 3, or 4. In yet another preferred embodiment, the percent homology between two nucleic acid sequences can be accomplished using the GAP program in the GCG software package (available at http://www.gcg.com), using a gap weight of 50 and a length weight of 3.

This invention is further illustrated by the following examples which should not be construed as limiting. The contents of all references, patents, Sequence Listing, Figures, and published patent applications cited throughout this application are incorporated herein by reference.

EXAMPLES

General Methodology

Strains. *Corynebacterium glutamicum* ATCC 21526 was obtained from the American Type and Culture Collection (Manassas, USA), This homoserine auxotrophic strain excretes lysine during L-threonine limitation due to the bypass of concerted aspartate kinase inhibition. Precultures were grown in complex medium containing 5 g L$^{-1}$ of either fructose or glucose. For agar plates the complex medium was additionally amended with 12 g L$^{-1}$ agar. For the production of cells as inoculum for the tracer experiments and the tracer studies itself a minimal medium amended with 1 mg ml$^{-1}$ calcium panthotenate.HCl was used (Wittmann, C. and E. Heinzle. 2002. Appl. Environ. Microbiol. 68:5843-5859). In this medium concentrations of carbon source glucose or fructose, of the essential amino acids threonine, methionine and leucine and of citrate were varied as specified below.

Cultivation. Precultivation consisted of three steps involving (i) a starter cultivation in complex medium with cells from agar plate as inoculum, (ii) a short cultivation for adaption to minimal medium, and (iii) a prolonged cultivation on minimal medium with elevated concentrations of essential amino acids. Pre-cultures inoculated from agar plates were grown overnight in 100 ml baffled shake flasks on 10 ml complex medium. Afterwards cells were harvested by centrifugation (8800 g, 2 min, 30° C.), inoculated into minimal medium, and grown up to an optical density of 2 to obtain exponentially growing cells adapted to minimal medium. Afterwards cells were harvested by centrifugation (8800 g, 30° C., and 2 min) including a washing step with sterile 0.9% NaCl. They were then inoculated into 6 ml minimal medium in 50 ml baffled shake flasks with initial concentrations of 0.30 g $L^{-1}$ threonine, 0.08 g $L^{-1}$ methionine, 0.20 g $L^{-1}$ leucine, and 0.57 g $L^{-1}$ citrate. As carbon source 70 mM glucose or 80 mM fructose were added, respectively. Cells were grown until depletion of the essential amino acids, which was checked by HPLC analysis. At the end of the growth phase cells were harvested, and washed with sterile NaCl (0.9%). Subsequently they were transferred into 4 ml minimal tracer medium in 25 ml baffled shake flasks for metabolic flux analysis under lysine producing conditions. The tracer medium did not contain any threonine, methionine, leucine and citrate. For each carbon source two parallel flasks were incubated containing (i) 40 mM [1-$^{13}$C] labeled substrate, and (ii) 20 mM [$^{13}C_6$] labeled substrate plus 20 mM of naturally labeled substrate, respectively. All cultivations were carried out on a rotary shaker (Inova 4230, New Brunswick, Edison, N.J., USA) at 30° C. and 150 rpm.

Chemicals. 99% [1-$^{13}$C] glucose, 99% [1-$^{13}$C] fructose, 99% [$^{13}C_6$] glucose and 99% [$^{13}C_6$] fructose were purchased from Campro Scientific (Veenendaal, Netherlands). Yeast extract and tryptone were obtained from Difco Laboratories (Detroit, Mich. USA). All other applied chemicals were from Sigma (St. Louis, Mich. USA), Merck (Darmstadt, Germany) or Fluka (Buchs, Switzerland), respectively, and of analytical grade Substrate and product analysis. Cell concentration was determined by measurement of cell density at 660 nm ($OD_{660nm}$) using a photometer (Marsha Pharmacia biotech, Freiburg, Germany) or by gravimetry. The latter was determined by harvesting 10 ml of cells from cultivation broth at room temperature for 10 min at 3700 g, including a washing step with water. Washed cells were dried at 80° C. until weight constancy. The correlation factor (g biomass/$OD_{660nm}$) between dry cell dry mass and $OD_{660nm}$ was determined as 0.353.

Concentrations of extracellular substrates and products were determined in cultivation supernatants, obtained via 3 min centrifugation at 16000 g. Fructose, glucose, sucrose, and trehalose were quantified by GC after derivatization into oxime trimethylsiiyl derivatives. For this purpose a HP 6890 gas chromatograph (Hewlett Packard, Palo Alto, USA) with an HP 5MS column (5% phenyl-methyl-siloxane-diphenyldimethylpolysiloxane, 30 m×250 μm, Hewlett Packard, Paolo Alto, Calif., USA), and a quadrupole mass selective detector with electron impact ionization at 70 eV (Agilent Technologies, Waldbronn, Germany) was applied. Sample preparation included lyophilization of the culture supernatant, dissolution in pyridine, and subsequent two-step derivatization of the sugars with hydroxylamine and (trimethylsilyl) trifluoroacetamide (BSTFA) (Macherey & Nagel, Duren, Germany) (13, 14). β-D-ribose was used as internal standard for quantification. The injected sample volume was 0.2 μl. The time program for GC analysis was as follows: 150° C. (0-5 min), 8° C. $min^{-1}$ (5-25 min), 310° C. (25-35 min). Helium was used as carrier gas with a flow of 1.5 l $min^{-1}$. The inlet temperature was 310° C. and the detector temperature was 320° C. Acetate, lactate, pyruvate, 2-oxoglutarate, and dihydroxyacetone were determined by HPLC utilizing an Aminex-HPX-87H Biorad Column (300×7.8 mm, Hercules, Calif., USA) with 4 mM sulfuric acid as mobile phase at a flow rate of 0.8 ml $min^{-1}$, and UV-detection at 210 nm. Glycerol was quantified by enzymatic measurement (Boehringer, Mannheim, Germany). Amino acids were analyzed by HPLC (Agilent Technologies, Waldbronn, Germany) utilizing a Zorbax Eclypse-AAA column (150×4.6 mm, 5 μm, Agilent Technologies, Waldbronn Germany), with automated online derivatization (o-phtaldialdehyde+3-mercaptopropionic acid) at a flow rate of 2 ml $min^{-1}$, and fluorescence detection. Details are given in the instruction manual, α-amino butyrate was used as internal standard for quantification.

$^{13}$C labeling analysis. The labeling patterns of lysine and trehalose in cultivation supernatants were quantified by GC-MS. Hereby single mass isotopomer fractions were determined. In the current work they are defined as $M_0$ (relative amount of non-labelled mass isotopomer fraction), $M_1$ (relative amount of single labelled mass isotopomer fraction) and corresponding terms for higher labelling. GC-MS analysis of lysine was performed after conversion into the t-butyl-dimethylsilyl (TBDMS) derivate as described previously (Rubino, F. M. 1989. J. Chromatogr. 473:125-133). Quantification of mass isotopomer distributions was performed in selective ion monitoring (SIM) mode for the ion cluster m/z 431-437. This ion cluster corresponds to a fragment ion, which is formed by loss of a t-butyl group from the derivatization residue, and thus includes the complete carbon skeleton of lysine (Wittmann, C, M. Hans and E. Heinzle. 2002. Analytical Biochem. 307:379-382). The labeling pattern of trehalose was determined from its trimethylsilyl (TMS) derivate as described previously (Wittmann, C, H. M. Kim and E. Heinzle. 2003. Metabolic flux analysis at miniaturized scale, submitted). The labeling pattern of trehalose was estimated via the ion cluster at m/z 361-367 corresponding to a fragment ion that contained an entire monomer unit of trehalose and thus a carbon skeleton equal to that of glucose 6-phosphate. All samples were measured first in scan mode therewith excluding isobaric interference between analyzed products and other sample components. All measurements by SIM were performed in duplicate. The experimental errors of single mass isotopomer fractions in the tracer experiments on fructose were 0.85% ($M_0$), 0.16% ($M_1$), 0.27% ($M_2$), 0.35% ($M_3$), 0.45% ($M_4$) for lysine on [1-$^{13}$C] fructose, 0.87% ($M_0$), 0.19% ($M_0$, 0.44% ($M_2$), 0.45% ($M_3$), 0.88% ($M_0$ for trehalose on [1-$^{13}$C] fructose, and 0.44% ($M_0$), 0.54% ($M_0$, 0.34% ($M_2$), 0.34% ($M_3$) 0.19% ($M_1$), 0.14% ($M_5$) and 0.52% ($M_6$) for trehalose on 50% [$^{13}C_6$] fructose, respectively. The experimental errors of MS measurements in glucose tracer experiments were 0.47% ($M_0$), 0.44% ($M_0$, 0.21% ($M_2$), 0.26% ($M_3$), 0.77% ($M_4$) for lysine on [1-$^{13}$C] glucose, 0.71% ($M_0$), 0.85% ($M_0$, 0.17% ($M_2$), 0.32% ($M_3$), 0.46% ($M_4$) for trehalose on [1-$^{13}$C] glucose, and 1.29% ($M_0$), 0.50% ($M_0$, 0.83% ($M_2$), 0.84% ($M_3$), 1.71% ($M_4$), 1.84% ($M_5$) and 0.58% ($M_6$) for trehalose on 50% [$^{13}C_6$] glucose, respectively.

Metabolic modelling and parameter estimation. All metabolic simulations were carried out on a personal computer. Metabolic network of lysine-producing C. glutamicum was implemented in Matlab 6.1 and Simulink 3.0 (Mathworks, Inc., Natick, Mass. USA). The software implementation included an isotopomer model in Simulink to calculate the $^{13}$C labeling distribution in the network. For parameter estimation the isotopomer model was coupled with an iterative optimization algorithm in Matlab. Details on the applied computational tools are given by Wittmann and Heinzle (Wittmann, C. and E. Heinzle. 2002. Appl. Environ. Microbiol. 68:5843-5859).

The metabolic network was based on previous work and comprised glycolysis, pentose phosphate pathway (PPP), tricarboxylic acid (TCA) cycle, anaplerotic carboxylation of pyruvate, biosynthesis of lysine and other secreted products (Tab. 1), and anabolic fluxes from intermediary precursors into biomass. In addition uptake systems for glucose and fructose were alternatively implemented. Uptake of glucose involved phosphorylation to glucose 6-phosphate via a PTS (Ohnishi, J., S. Mitsuhashi, M. Hayashi, S. Ando, H. Yokoi, K. Ochiai and M. A. Ikeda. 2002. Appl. Microbiol. Biotechnol. 58:217-223). For fructose two uptake systems were considered: (i) uptake by $PTS_{Fructose}$ and conversion of fructose into fructose 1,6-bisphosphatase via fructose 1-phosphate and (ii) uptake by $PTS_{Mannose}$ leading to fructose 6-phosphate, respectively (Dominguez, H., C. Rollin, A. Guyonvarch, J. L. Guerquin-Kern, M. Cocaign-Bousquet and N. D. Lindley. 1998. Eur. J. Biochem. 254:96-102). In addition fructose-1,6-bisphosphatase was implemented into the model to allow carbon flux in both directions in the upper glycolysis. Reactions regarded reversible were transaldolase and transketolases in the PPP. Additionally glucose 6-phosphate isomerase was considered reversible for the experiments on glucose, whereby the trehalose labeling sensitively reflected the reversibility of this enzyme. In contrast the reversibility of glucose 6-phosphate isomerase could not be determined on fructose. In fructose-grown cells, glucose 6-phosphate is exclusively formed from fructose 6-phosphate leading to identical labeling patterns for the two pools. Therefore interconversion between glucose 6-phosphate and fructose 6-phosphate by a reversible glucose 6-phosphate isomerase does not result in labeling differences that could be used for the estimation of glucose 6-phosphate isomerase reversibility. The measured labeling of lysine and trehalose was not sensitive towards (i) the reversibility of the flux between the lumped pools of phosphoenolpyruvate/pyruvate and malate/oxaloacetate and (ii) the reversibility of malate dehydrogenase and fumarate hydratase in the TCA cycle. Accordingly these reactions were regarded irreversible. The labeling of alanine from a mixture of naturally labeled and [$^{13}C_6$] labeled substrate, which is sensitive for these flux parameters, was not available in this study. Based on previous results the glyoxylate pathway was assumed to be inactive (Wittmann, C. and E. Heinzle. 2002. Appl. Environ. Microbiol. 68:5843-5859).

Stoichiometric data on growth, product formation, and biomass composition of C. glutamicum together with mass spectrometric labeling data of secreted lysine and trehalose were used to calculate metabolic flux distributions. The set of fluxes that gave minimum deviation between experimental ($M_{i,exp}$) and simulated ($M_{i,calc}$) mass isotopomer fractions of lysine and trehalose of the two parallel experiments was taken as best estimate for the intracellular flux distribution. As described in the appendix the two networks of glucose-grown and fructose-grown cells were over determined. A least square approach was therefore possible. As error criterion a weighted sum of least squares (SLS) was used, where $S_{i,exp}$ is the standard deviation of the measurements (Eq. 1).

$$SLS = \sum_i \frac{(M_{i,exp} - M_{i,calc})^2}{S_{i,exp}^2} \quad \text{(Equation 1)}$$

Multiple parameter initializations were applied to investigate whether an obtained flux distribution represented a global optimum. For all strains the glucose uptake flux during lysine production was set to 100% and the other fluxes in the network are given as relative molar fluxes normalized to the glucose uptake flux.

Statistical evaluation. Statistical analysis of the obtained metabolic fluxes was carried out by a Monte-Carlo approach as described previously (Wittmann, C. and E. Heinzle. 2002. Appl. Environ. Microbiol. 68:5843-5859). For each strain, the statistical analysis was carried out by 100 parameter estimation runs, whereby the experimental data, comprising measured mass isotopomer ratios and measured fluxes, were varied statistically. From the obtained data 90% confidence limits for the single parameters were calculated.

Example I

Lysine Production by C. glutamicum on Fructose and Glucose

Metabolic fluxes of lysine producing C. glutamicum were analyzed in comparative batch cultures on glucose and fructose. For this purpose pre-grown cells were transferred into tracer medium and incubated for about 5 hours. The analysis of substrates and products at the beginning and the end of the tracer experiment revealed drastic differences between the two carbon sources. Overall 11.1 mM lysine was produced on glucose, whereas a lower concentration of only 8.6 mM was reached on fructose. During the incubation over 5 hours, the cell concentration increased from 3.9 g L-1 to 6.0 g L-1 (glucose) and from 3.5 g L-1 to 4.4 g L-1 (fructose). Due to the fact that threonine and methionine were not present in the medium, internal sources were probably utilized by the cells for biomass synthesis. The mean specific sugar uptake rate was higher on fructose (1.93 mmol $g^{-1}$ $h^{-1}$) compared to glucose (1.71 mmol $g^{-1}$ $h^{-1}$). As depicted in Table 1, the obtained yields of C. glutamicum ATCC 21526 differed drastically between fructose and glucose. This involved the main product lysine and various byproducts. Concerning lysine, the yield on fructose was 244 mmol mol-1 and thus was lower compared to the yield on glucose (281 mmol mol-1). Additionally the carbon source had a drastic influence on the biomass yield, which was reduced by almost 50% on fructose in comparison to glucose. The most significant influence of the carbon source on byproduct formation was observed for dihydroxyacetone, glycerol, and lactate. On fructose, accumulation of these byproducts was strongly enhanced. The yield for glycerol was 10 fold higher, whereas dihydroxyacetone and lactate secretion were increased by a factor of six. Dihydroxyacetone was the dominating byproduct on fructose. Due to the lower biomass yield a significantly reduced demand for anabolic precursors resulted for fructose-grown cells (Table 2).

TABLE 1

Biomass and metabolites in the stage of lysine production by
Corynebacterium glutamicum ATCC 21526 from glucose (left) and
fructose (right). Experimental yields are mean values of two parallel
incubations on (i) 40 mM [1-$^{13}$C] labeled substrate and (ii) 20 mM
[$^{13}$C$_6$] labeled substrate plus 20 mM naturally labeled substrate with
corresponding deviations between the two incubations. All yields
are given in (mmol product) (mol)$^{-1}$ except the yield for biomass,
which is given in (mg of dry biomass) (mmol)$^{-1}$.

| Yield | Lysine production on glucose | Lysine production on fructose |
|---|---|---|
| Biomass | 54.1 ± 0.8 | 28.5 ± 0.0 |
| Lysine | 281.0 ± 2.0 | 244.4 ± 23.3 |
| Valine | 0.1 ± 0.0 | 0.0 ± 0.0 |
| Alanine | 0.1 ± 0.0 | 0.4 ± 0.1 |
| Glycine | 6.6 ± 0.0 | 7.1 ± 0.4 |
| Dihydroxyacetone | 26.3 ± 15.3 | 156.6 ± 25.8 |
| Glycerol | 3.8 ± 2.4 | 38.4 ± 3.9 |
| Trehalose | 3.3 ± 0.5 | 0.9 ± 0.1 |
| α-Ketoglutarate | 1.6 ± 0.4 | 6.5 ± 0.3 |
| Acetate | 45.1 ± 0.3 | 36.2 ± 5.7 |
| Pyruvate | 1.2 ± 0.4 | 2.1 ± 0.5 |
| Lactate | 7.1 ± 1.7 | 38.3 ± 3.5 |

TABLE 2

Anabolic demand of Corynebacterium glutamicum ATCC 21526 for
intracellular metabolites in the stage of lysine production from
glucose (left) and fructose (right). Experimental data are mean values
of two parallel incubations on (i) [1-$^{13}$C] labeled substrate and (ii) a 1:1
mixture of naturally labeled and [$^{13}$C$_6$] substrate with deviation
between the two incubations.

| Precursor Demand* mmol (mol glucose)$^{-1}$ | Lysine production on glucose | Lysine production on fructose |
|---|---|---|
| Glucose 6-phosphate | 11.09 ± 0.16 | 5.84 ± 0.05 |
| Fructose 6-phosphate | 3.84 ± 0.06 | 2.02 ± 0.02 |
| Pentose 5-phosphate | 47.50 ± 0.70 | 25.05 ± 0.21 |
| Erythrose 4-phosphate | 14.50 ± 0.22 | 7.64 ± 0.06 |
| Glyceraldehyde 3-phosphate | 6.98 ± 0.10 | 3.68 ± 0.03 |
| 3-Phosphoglycerate | 59.95 ± 0.89 | 36.85 ± 0.31 |
| Pyruvate/Phosphoenolpyruvate | 107.80 ± 1.60 | 56.80 ± 0.48 |
| α-Ketoglutarate | 92.51 ± 1.37 | 48.73 ± 0.41 |
| Oxaloacetate | 48.91 ± 0.72 | 45.76 ± 0.38 |
| Acetyl CoA | 135.30 ± 2.00 | 71.25 ± 0.60 |
| Diaminopimelate + Lysine** | 18.83 ± 0.28 | 9.92 ± 0.08 |

*The estimation of precursor demands was based on the experimental biomass yield obtained for each strain (Tab. 1) and the biomass composition previously measured for C. glutamicum (Marx, A., A. A. de Graaf, W. Wiechert, L. Eggeling and H. Sahm. 1996. Biotechnol. Bioeng. 49: 111-129).
**Diaminopimelate and lysine are regarded as separate anabolic precursors. This is due to the fact that anabolic fluxes from pyruvate and oxaloacetate into diaminopimelate (cell wall) and lysine (protein) contribute in addition to the flux of lysine secretion to the overall flux through the lysine biosynthetic pathway.

Example II

Manual Inspection of $^{13}$C-Labeling Patterns in Tracer Experiments

Figure 2:
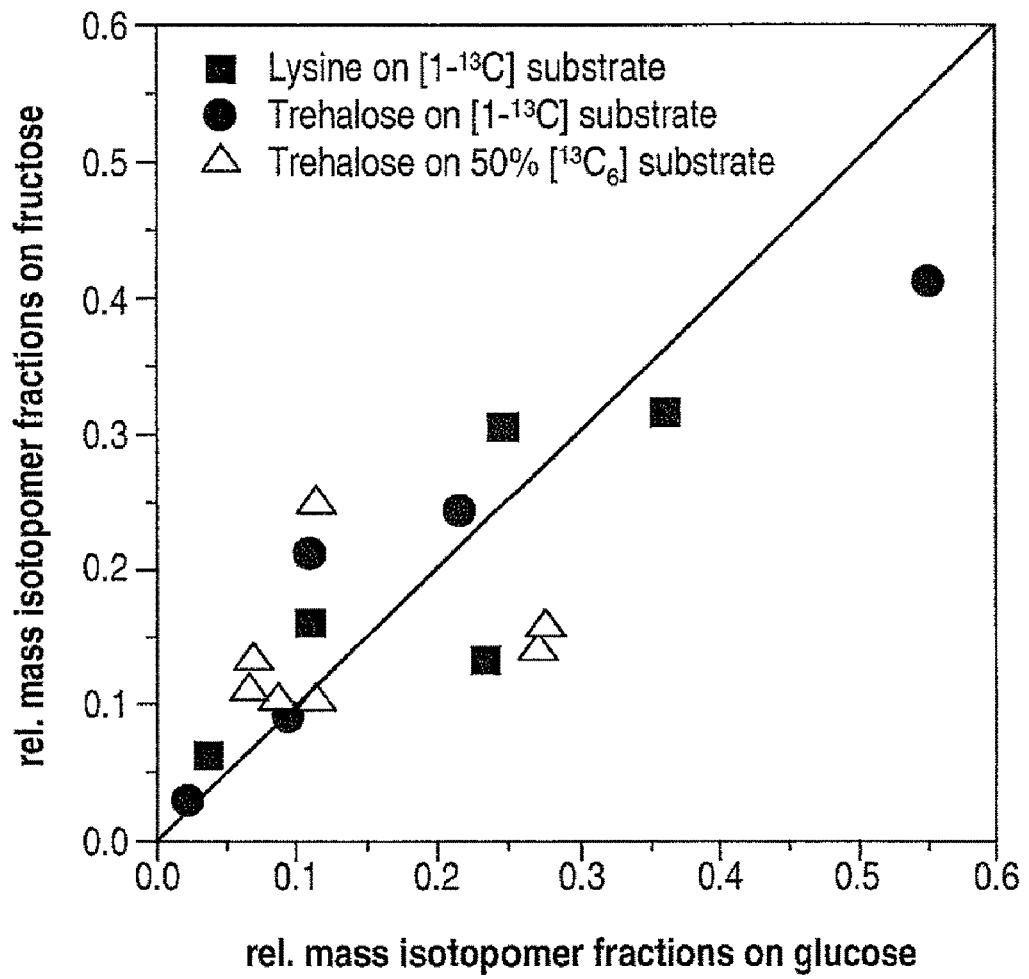
FIG. 2: Comparison of relative mass isotopomer fractions of secreted lysine and trehalose measured by GC/MS in tracer experiments of *Corynebacterium glutamicum* ATCC 21526 during lysine production on glucose and fructose.

Relative mass isotopomer fractions of secreted lysine and trehalose were quantified with GC-MS. These mass isotopomer fractions are sensitive towards intracellular fluxes and therefore display fingerprints for the fluxome of the investigated biological system. As shown in FIG. 2, labeling patterns of secreted lysine and trehalose differed significantly between glucose and fructose-grown cells of C. glutamicum. The differences were found for both applied tracer labelings and for both measured products. This indicates substantial differences in the carbon flux pattern depending on the applied carbon source. As previously shown, mass isotopomer fractions from two parallel cultivations of C. glutamicum on a mixture of [1-$^{13}$C] and [$^{13}$C$_6$] glucose were almost identical (Wittmann, C, H. M. Kim and E. Heinzle. 2003. Metabolic flux analysis at miniaturized scale, submitted). Therefore, the differences observed can be clearly related to substrate specific differences in metabolic fluxes.

Example III

Estimation of Intracellular Fluxes

A central issue of the performed studies was the comparative investigation of intracellular fluxes of C. glutamicum during lysine production on glucose and fructose as carbon source, respectively. For this purpose, the experimental data obtained from the tracer experiments were used to calculate metabolic flux distributions for each substrate applying the flux estimation software as described above. The parameter estimation was carried out by minimizing the deviation between experimental and calculated mass isotopomer fractions. The performed approach utilized metabolite balancing during each step of the optimization. This included (i) stoichiometric data on product secretion (Table 2) and (ii) stoichiometric data on anabolic demand for biomass precursors (Table 3). The set of intracellular fluxes that gave the minimum deviation between experimental and simulated labeling patterns was taken as best estimate for the intracellular flux distribution. For both scenarios, identical flux distributions were obtained with multiple initialization values, suggesting that global minima were identified. Obviously, good agreement between experimentally determined and calculated mass isotopomer ratios was achieved (Table 4).

TABLE 3

Relative mass isotopomer fractions of secreted lysine and trehalose of lysine producing Corynebacterium glutamicum
ATCC 21526 cultivated on glucose and fructose, respectively. For both carbon sources two parallel tracer experiments on
(i) [1-$^{13}$C] labeled and (ii) a 1:1 mixture of naturally $^{13}$C labeled and [$^{13}$C$_6$] labeled tracer substrate were carried out.
Experimental GC/MS data (exp) and values predicted by the solution of the mathematical model corresponding
to the optimized set of fluxes (calc). M$_0$ denotes the relative amount of non-labelled mass isotopomer fraction, M$_1$ the
relative amount of the single labelled mass isotopomer fraction, and corresponding terms stand for higher labelling

| | Lysine (on [1-$^{13}$C] labeled substrate) | | | | | Trehalose (on [1-$^{13}$C] labeled substrate) | | | | | Trehalose (on 50% [$^{13}$C$_6$] labeled substrate) | | | | | | |
|---|---|---|---|---|---|---|---|---|---|---|---|---|---|---|---|---|---|
| | M$_0$ | M$_1$ | M$_2$ | M$_3$ | M$_4$ | M$_0$ | M$_1$ | M$_2$ | M$_3$ | M$_4$ | M$_0$ | M$_1$ | M$_2$ | M$_3$ | M$_4$ | M$_5$ | M$_6$ |
| glucose | | | | | | | | | | | | | | | | | |
| exp | 0.234 | 0.360 | 0.247 | 0.110 | 0.037 | 0.110 | 0.551 | 0.216 | 0.094 | 0.023 | 0.271 | 0.114 | 0.087 | 0.115 | 0.069 | 0.066 | 0.279 |
| calc | 0.242 | 0.355 | 0.245 | 0.110 | 0.037 | 0.114 | 0.549 | 0.212 | 0.094 | 0.023 | 0.268 | 0.113 | 0.085 | 0.113 | 0.068 | 0.064 | 0.289 |

TABLE 3-continued

Relative mass isotopomer fractions of secreted lysine and trehalose of lysine producing Corynebacterium glutamicum ATCC 21526 cultivated on glucose and fructose, respectively. For both carbon sources two parallel tracer experiments on (i) [1-$^{13}$C] labeled and (ii) a 1:1 mixture of naturally $^{13}$C labeled and [$^{13}$C$_6$] labeled tracer substrate were carried out. Experimental GC/MS data (exp) and values predicted by the solution of the mathematical model corresponding to the optimized set of fluxes (calc). $M_0$ denotes the relative amount of non-labelled mass isotopomer fraction, $M_1$ the relative amount of the single labelled mass isotopomer fraction, and corresponding terms stand for higher labelling

| | Lysine (on [1-$^{13}$C] labeled substrate) | | | | | Trehalose (on [1-$^{13}$C] labeled substrate) | | | | | Trehalose (on 50% [$^{13}$C$_6$] labeled substrate) | | | | | | |
|---|---|---|---|---|---|---|---|---|---|---|---|---|---|---|---|---|---|
| | $M_0$ | $M_1$ | $M_2$ | $M_3$ | $M_4$ | $M_0$ | $M_1$ | $M_2$ | $M_3$ | $M_4$ | $M_0$ | $M_1$ | $M_2$ | $M_3$ | $M_4$ | $M_5$ | $M_6$ |
| fructose | | | | | | | | | | | | | | | | | |
| exp | 0.133 | 0.316 | 0.304 | 0.162 | 0.062 | 0.212 | 0.412 | 0.244 | 0.092 | 0.030 | 0.141 | 0.103 | 0.104 | 0.250 | 0.133 | 0.110 | 0.159 |
| calc | 0.139 | 0.321 | 0.298 | 0.159 | 0.061 | 0.195 | 0.419 | 0.254 | 0.094 | 0.030 | 0.144 | 0.103 | 0.102 | 0.245 | 0.131 | 0.111 | 0.164 |

Example IV

Metabolic Fluxes on Fructose and Glucose During Lysine Production

The obtained intracellular flux distributions for lysine-producing *C. glutamicum* on glucose and fructose are shown in FIGS. (4, 5). Obviously, the intracellular fluxes differed tremendously depending on the carbon source applied. On glucose, 62% of the carbon flux was directed towards the PPP, whereas only 36% were channeled through the glycolytic chain (FIG. 4) Due to this a relatively high amount, 124% NADPH was generated by the PPP enzymes glucose 6-phosphate dehydrogenase and 6-phosphogluconate dehydrogenase. The situation on fructose was completely different (FIG. 5). The performed flux analysis revealed the in vivo activity of two PTS for uptake of fructose, whereby 92.3% of fructose were taken up by fructose specific PTS$_{Fructose}$. A comparably small fraction of 7.7% of fructose was taken up by PTS$_{Mannose}$. Thus, the majority of fructose entered the glycolysis at the level of fructose 1,6-bisphosphatase, whereas only a small fraction was channeled upstream at fructose 6-phosphate into the glycolytic chain. In comparison to glucose-grown cells, the PPP exhibited a dramatically reduced activity of only 14.4%. Glucose 6-phosphate isomerase operated in opposite directions on the two carbon sources. In glucose-grown cells 36.2% net flux were directed from glucose 6-phosphate to fructose 6-phosphate, whereas a backward net flux of 15.2% was observed on fructose.

On fructose, the flux through glucose 6-phosphate isomerase and PPP was about twice as high as the flux through the PTS$_{Mannose}$. However this was not due to a gluconeogenetic flux of carbon from fructose-1,6-bisphosphatase to fructose 6-phosphate, which could have supplied extra carbon flux towards the PPP. In fact flux through fructose 1,6-bisphosphatase catalyzing this reaction, was zero. The metabolic reactions responsible for the additional flux towards the PPP are the reversible enzymes transaldolase and transketolase in the PPP. About 3.5% of this additional flux was supplied by transketolase 2, which recycled carbon stemming from the PPP back into this pathway. Moreover 4.2% of flux was directed towards fructose 6-phosphate and the PPP by the action of transaldolase.

Figure 3:
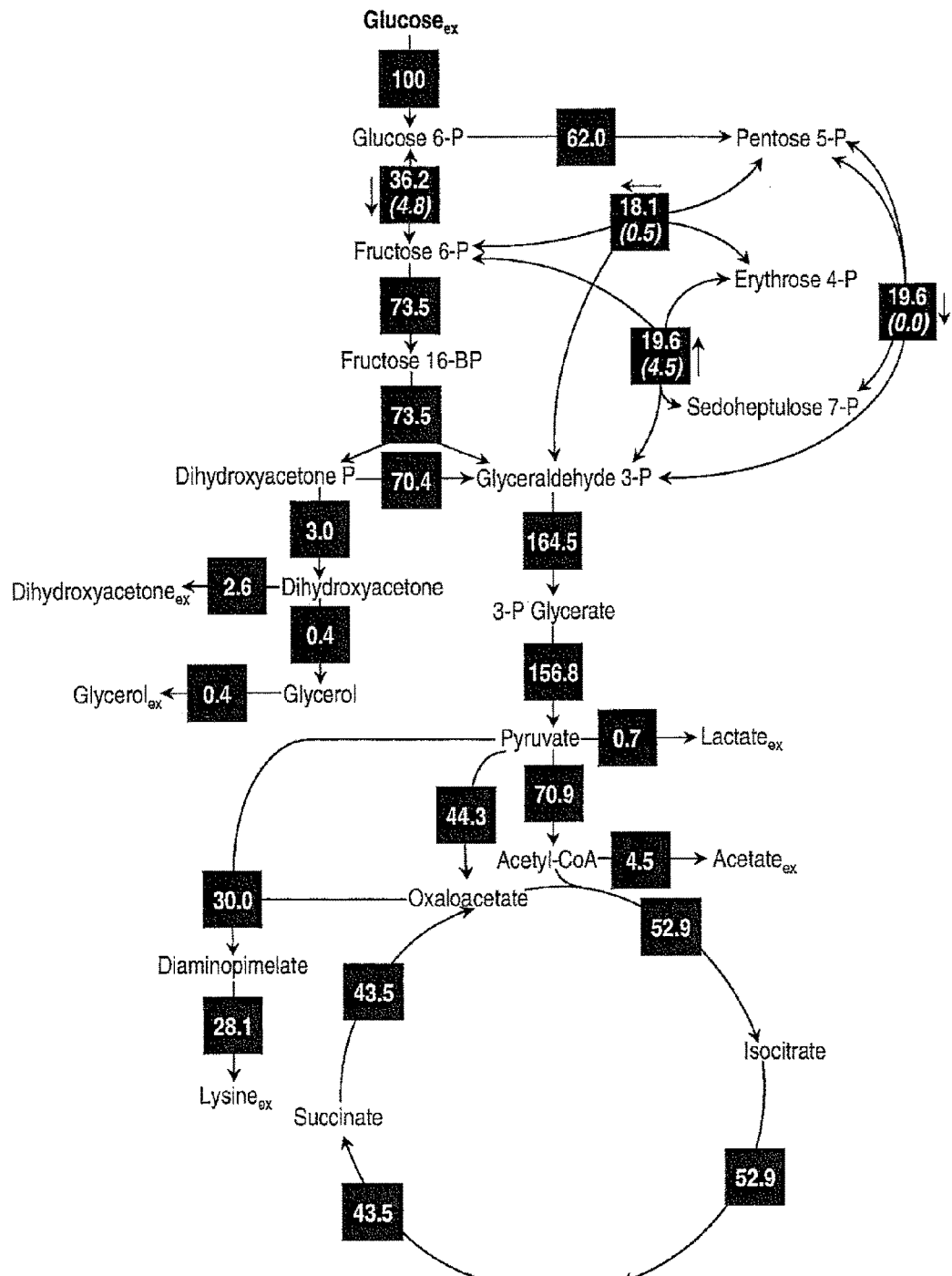
FIG. 3: In vivo carbon flux distribution in the central metabolism of *Corynebacterium glutamicum* ATCC 21526 during lysine production on glucose estimated from the best fit to the experimental results using a comprehensive approach of combined metabolite balancing and isotopomer modeling for $^{13}$C tracer experiments with labeling measurement of secreted lysine and trehalose by GC/MS, respectively. Net fluxes are given in square symbols, whereby for reversible reactions the direction of the net flux is indicated by an arrow aside the corresponding black box. Numbers in brackets below the fluxes of transaldolase, transketolase and glucose 6-phosphate isomerase indicate flux reversibilities. All fluxes are expressed as a molar percentage of the mean specific glucose uptake rate (1.77 mmol g$^{-1}$ h$^{-1}$).
Figure 4:
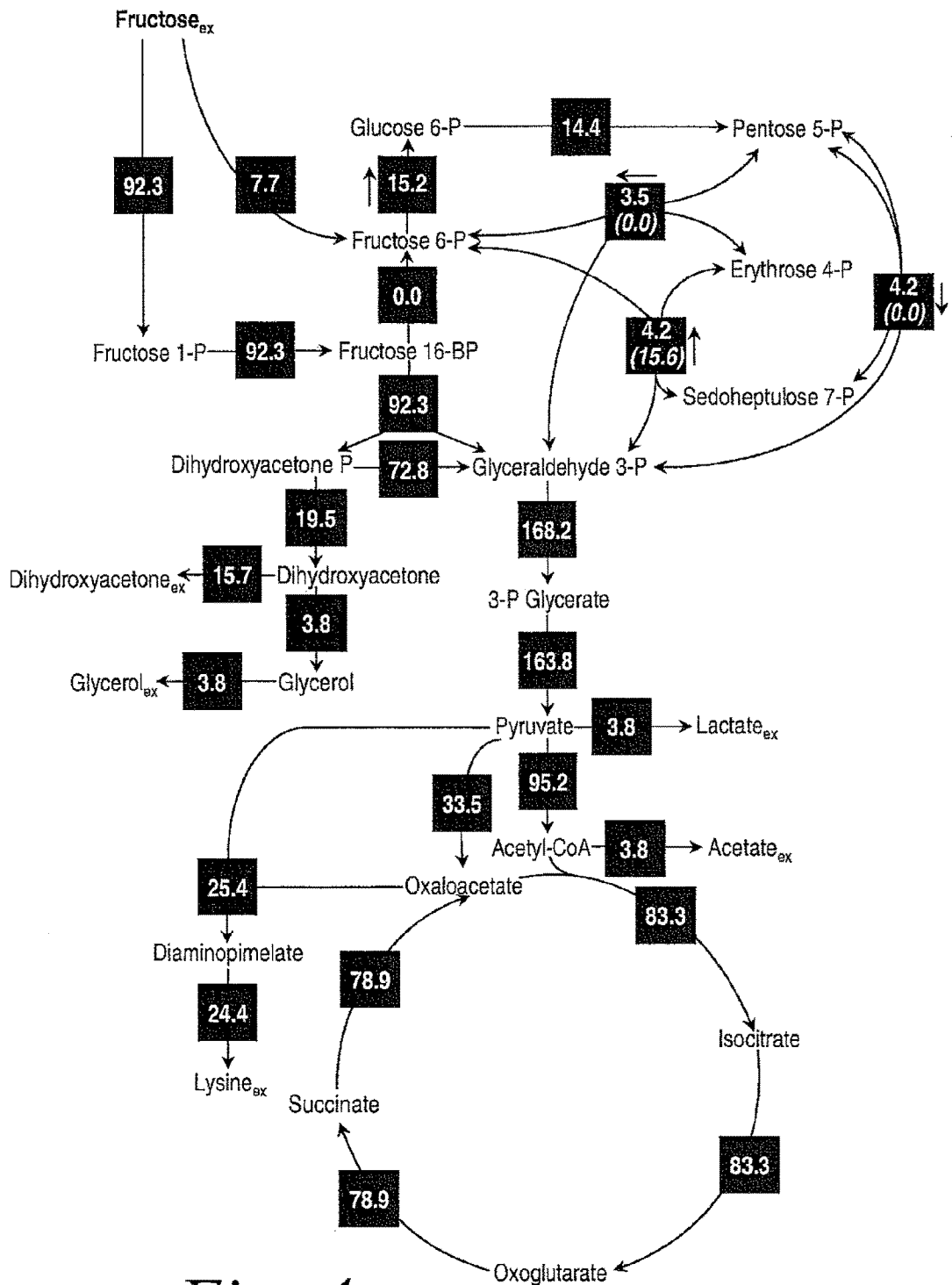
FIG. 4: In vivo carbon flux distribution in the central metabolism of *Corynebacterium glutamicum* ATCC 21526 during lysine production on fructose estimated from the best fit to the experimental results using a comprehensive approach of combined metabolite balancing and isotopomer modeling for $^{13}$C tracer experiments with labeling measurement of secreted lysine and trehalose by GC/MS, respectively. Net fluxes are given in square symbols, whereby for reversible reactions the direction of the net flux is indicated by an arrow aside the corresponding black box. Numbers in brackets below the fluxes of transaldolase, transketolase and glucose 6-phosphate isomerase indicate flux reversibilities. All fluxes are expressed as a molar percentage of the mean specific fructose uptake rate (1.93 mmol g$^{-1}$ h$^{-1}$).
Figure 5A:
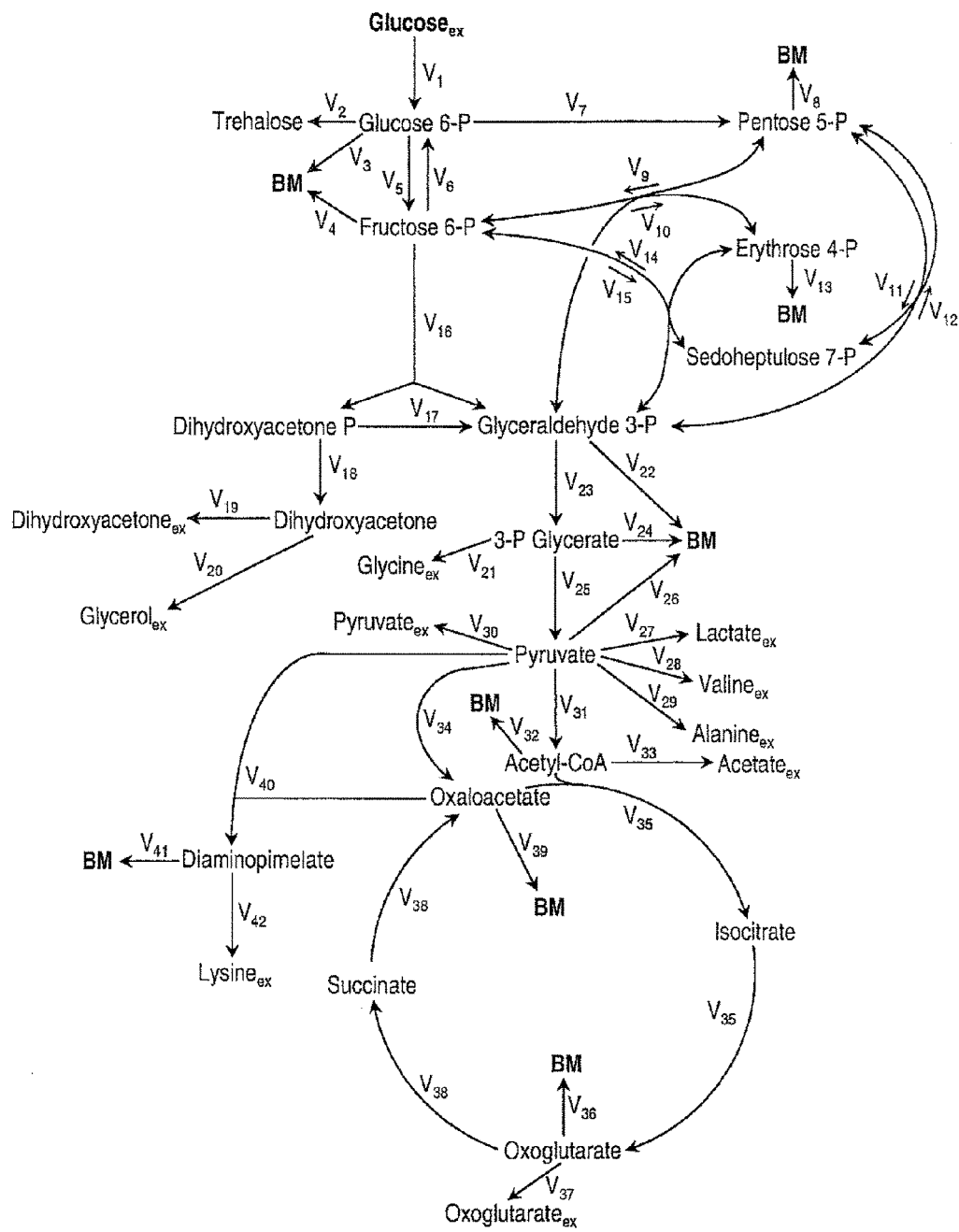
FIG. 5: Metabolic network of the central metabolism for glucose-grown (A) and fructose-grown (B) lysine producing *Corynebacterium glutamicum* including transport fluxes, anabolic fluxes and fluxes between intermediary metabolite pools.
Figure 5B:
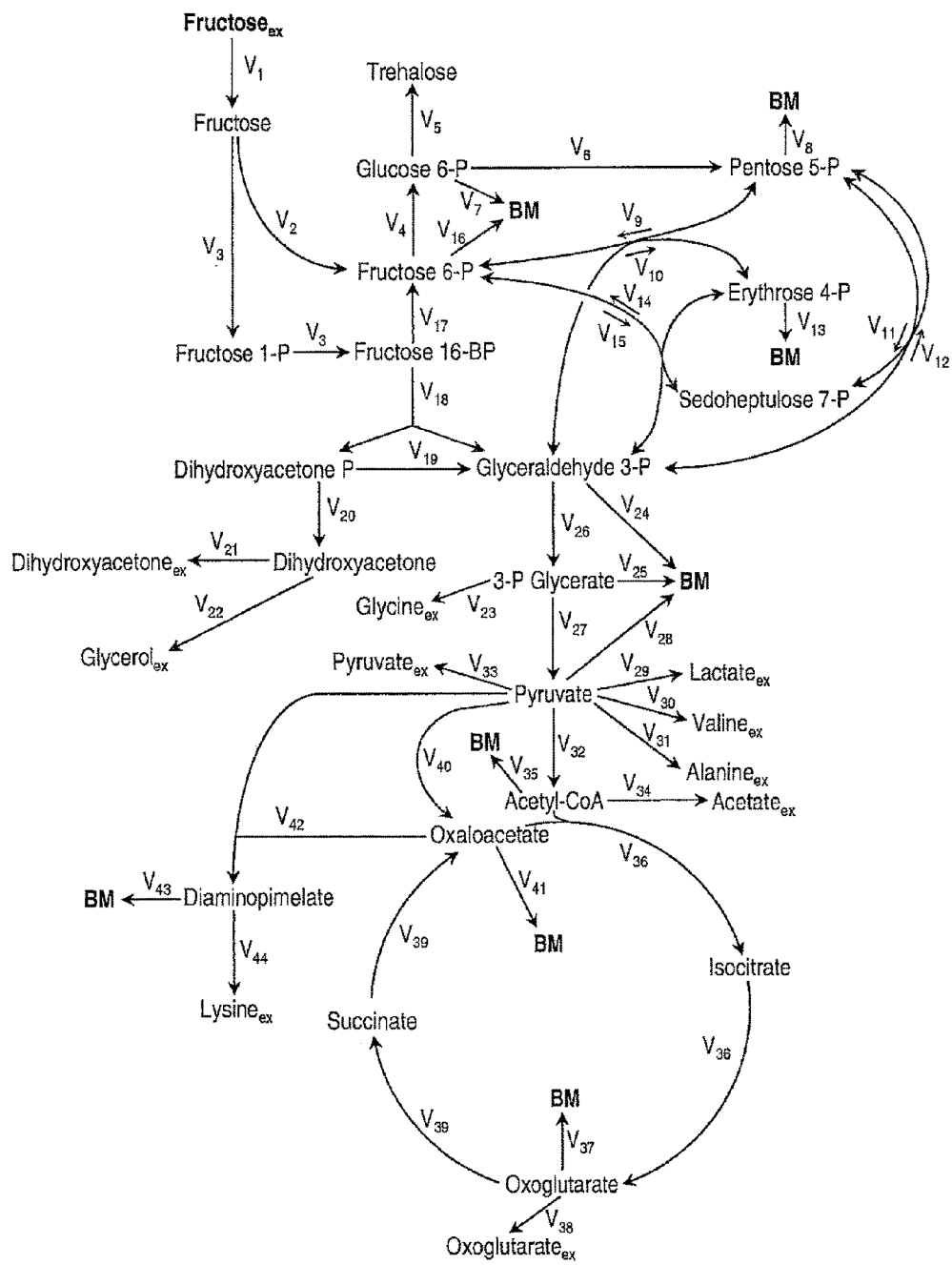

Depending on the carbon source, completely different flux patterns in lysine producing *C. glutamicum* were also observed around the pyruvate node (FIGS. 4, 5). On glucose the flux into the lysine pathway was 30.0%, whereas a reduced flux of 25.4% was found on fructose. The elevated lysine yield on glucose compared to fructose is the major reason for this flux difference, but also the higher biomass yield resulting in a higher demand for diaminopimelate for cell wall synthesis and lysine for protein synthesis contributes to it. The anaplerotic flux on glucose was 44.5% and thus markedly higher compared to the flux on fructose (33.5%). This is mainly due to the higher demand for oxaloacetate for lysine production, but also to the higher anabolic demands for oxaloacetate and 2-oxoglutarate on glucose. On the other hand, flux through pyruvate dehydrogenase was substantially lower on glucose (70.9%) compared to fructose (95.2%). This reduced carbon flux into the TCA cycle resulted in more than 30% reduced fluxes through TCA cycle enzymes on glucose (FIGS. 3, 4).

Statistical evaluation of the obtained fluxes by a Monte-Carlo approach was used to calculate 90% confidence intervals for the determined flux parameters. As shown for various key fluxes in Table 5, the confidence intervals were generally narrow. As example the confidence interval for the flux through glucose 6-phosphate dehydrogenase was only 1.2% for glucose-grown and 3.5% for fructose-grown cells. The chosen approach therefore allowed precise flux estimation. It can be concluded that the flux differences observed on glucose and fructose, respectively, are clearly caused by the applied carbon source.

It has to be noticed that the mean specific substrate uptake of 1.93 mmol g$^{-1}$ h$^{+1}$ on fructose was slightly higher than that of 1.77 mmol g$^{-1}$ h$^{-1}$ found on glucose. Due to this the absolute intracellular fluxes expressed in mmol g$^{-1}$ h$^{-1}$ are slightly increased in relation to glucose compared to the relative fluxes discussed above. The flux distributions of lysine producing *C. glutamicum* on fructose and glucose, respectively, are however so completely different, that all comparisons drawn above also hold for absolute carbon fluxes.

TABLE 4

Statistical evaluation of metabolic fluxes of lysine producing Corynebacterium glutamicum ATCC 21526 grown on fructose (left) and glucose (right) determined by $^{13}$C tracer studies with mass spectrometry and metabolite balancing: 90% confidence intervals of key flux parameters were obtained by a Monte-Carlo approach including 100 independent parameter estimation runs for each substrate with statistically varied experimental data.

| Flux parameter | Glucose | Fructose |
|---|---|---|
| Net Flux | | |
| fructose uptake by PTS$_{Frc}$ | — | [90.0 96.1] |
| fructose uptake by PTS$_{Man}$ | — | [3.9 10.0] |
| glucose 6-phosphate isomerase | [35.7 36.8] | [13.4 16.9] |
| phosphofructokinase | [35.7 36.8] | — |
| fructose 1,6-bisphosphatase* | — | [−2.1 3.4] |

TABLE 4-continued

Statistical evaluation of metabolic fluxes of lysine
producing Corynebacterium glutamicum ATCC 21526 grown
on fructose (left) and glucose (right) determined by $^{13}$C
tracer studies with mass spectrometry and metabolite balancing:
90% confidence intervals of key flux parameters were obtained by
a Monte-Carlo approach including 100 independent parameter estimation
runs for each substrate with statistically varied experimental data.

| Flux parameter | Glucose | Fructose |
|---|---|---|
| fructose 1,6-bisphosphatase aldolase | [73.7 73.8] | [91.7 92.9] |
| glucose 6-phosphate dehydrogenase | [62.5 63.7] | [12.6 16.1] |
| transaldolase | [19.4 19.8] | [3.6 4.1] |
| transketolase 1 | [19.4 19.8] | [3.6 4.1] |
| transketolase 2 | [17.9 18.3] | [2.9 4.0] |
| glyceraldehyde 3-phosphate dehydrogenase | [158.1 164.5] | [163.3 174.6] |
| pyruvate kinase | [156.2 167.4] | [158.9 168.2] |
| pyruvate dehydrogenase | [69.5 72.5] | [87.1 102.3] |
| pyruvate carboxylase | [43.7 44.8] | [29.9 37.3] |
| citrate synthase | [51.2 54.8] | [76.5 91.5] |
| isocitrate dehydrogenase | [51.2 54.8] | [76.5 91.5] |
| oxoglutarate dehydrogenase | [41.6 45.6] | [70.9 86.0] |
| aspartokinase | [29.6 30.3] | [21.8 29.2] |
| Flux Reversibility** | | |
| glucose 6-phosphate isomerase | [4.5 5.1] | — |
| transaldolase | [4.3 4.9] | [14.5 18.2] |
| transketolase 1 | [0.0 0.0] | [0.0 0.1] |
| transketolase 2 | [0.4 0.6] | [0.0 0.1] |

*The negative flux for the lower confidence boundary is equal to a positive flux in the reverse direction (through phosphofructokinase).
**Flux reversibility is defined as ratio of back flux to net flux.

Discussion of Examples I-IV:

A. Substrate Specific Culture Characteristics

Cultivation of lysine producing *C. glutamicum* on fructose and on glucose, respectively, revealed that growth and product formation strongly depend on the carbon source applied. Significantly reduced yields of lysine and biomass on fructose were previously also reported for another strain of *C. glutamicum*, where lysine and biomass yield were 30% and 20% less, respectively, compared to glucose (Kiefer, P., E. Heinzle and C. Wittmann. 2002. J. Ind. Microbiol. Biotechnol. 28:338-43). Cultivation of *C. glutamicum* and *C. melassecola* on fructose is linked to higher carbon dioxide production rates in comparison to glucose (Dominguez, H., C. Rollin, A. Guyonvarch, J. L. Guerquin-Kern, M. Cocaign-Bousquet and N. D. Lindley. 1998. Eur. J. Biochem. 254:96-102; Kiefer, P., E. Heinzle and C. Wittmann. 2002. J. Ind. Microbiol. Biotechnol. 28:338-43). This coincides with the elevated flux through the TCA cycle observed in the present work for this carbon source. Substrate specific differences were also observed for byproducts. The formation of trehalose was lower on fructose compared to glucose. This may be related to different entry points of glucose and fructose into glycolysis (Kiefer, P., E. Heinzle and C. Wittmann. 2002. J. Ind. Microbiol. Biotechnol. 28:338-43). Considering the uptake systems in *C. glutamicum*, utilization of glucose leads to the formation of the trehalose precursor glucose 6-phosphate, whereas fructose is converted into fructose 1,6-bisphosphatase and thus enters the central metabolism downstream from glucose 6-phosphate (Dominguez, H., C. Rollin, A. Guyonvarch, J. L. Guerquin-Kern, M. Cocaign-Bousquet and N. D. Lindley. 1998. Eur. J. Biochem. 254:96-102). Other byproducts such as dihydroxyacetone, glycerol, and lactate were strongly increased, when fructose was applied as carbon source. From the viewpoint of lysine production, this is not desired, because a substantial fraction of carbon is withdrawn from the central metabolism into the formed byproducts. The specific substrate uptake on fructose ($1.93$ mmol g$^{-1}$ h$^{-1}$) was higher than on glucose ($1.77$ mmol g$^{-1}$ h$^{-1}$). This result differs from a previous study on exponentially growing *C. melassecola* ATCC 17965 (Dominguez, H., C. Rollin, A. Guyonvarch, J. L. Guerquin-Kern, M. Cocaign-Bousquet and N. D. Lindley. 1998. Eur. J. Biochem. 254:96-102), where similar specific uptake rates on fructose and glucose were observed. The higher uptake rate for fructose observed in our study might be due to the fact that the studied strains are different. *C. melassecola* and *C. glutamicum* are related species, but might differ in certain metabolic properties. The strain studied in the present work was previously derived by classical strain optimization. This could have introduced mutations influencing substrate uptake. Another explanation is the difference in cultivation conditions. Fructose might be more effectively utilized under conditions of limited growth and lysine production.

B. Metabolic Flux Distributions

The obtained intracellular flux distributions for lysine-producing *C. glutamicum* on glucose and fructose revealed tremendous differences. Statistical evaluation of the obtained fluxes revealed narrow 90% confidence intervals, so that the observed flux differences can be clearly attributed to the applied carbon sources. One of the most remarkable differences concerns the flux partitioning between glycolysis and PPP. On glucose 62.3% of carbon was channeled through the PPP. The predominance of the PPP of lysine-producing *C. glutamicum* on this substrate has been previously observed in different studies (Marx, A., A. A. de Graaf, W. Wiechert, L. Eggeling and H. Sahm. 1996. Biotechnol. Bioeng. 49:111-129; Wittmann, C. and E. Heinzle. 2001. Eur. J. Biochem. 268:2441-2455; Wittmann, C. and E. Heinzle. 2002. Appl. Environ. Microbiol. 68:5843-5859). On fructose the flux into the PPP was reduced to 14.4%. As identified by the performed metabolic flux analysis, this was mainly due to the unfavourable combination of the entry of fructose at the level of fructose 1,6-bisphosphatate and the inactivity of fructose-1,6-bisphosphatase. The observed inactivity of fructose-1,6-bisphosphatase agrees well with enzymatic measurements of *C. melassecola* ATCC 17965 during exponential growth on fructose and on glucose, respectively (Dominguez, H., C. Rollin, A. Guyonvarch, J. L. Guerquin-Kern, M. Cocaign-Bousquet and N. D. Lindley. 1998, Eur. J. Biochem. 254:96-102).

Surprisingly, the flux through glucose 6-phosphate isomerase and PPP was about twice as high as the flux through the PTS$_{Mannose}$, when *C. glutamicum* was cultivated on fructose. Due to the inactivity of fructose-1,6-bisphosphatase this was not caused by a gluconeogenetic flux. In fact, *C. glutamicum* possesses an operating metabolic cycle via fructose 6-phosphate, glucose 6-phosphate, and ribose 5-phosphate. Additional flux into the PPP was supplied by transketolase 2, which recycled carbon stemming from the PPP back into this pathway, and by the action of transaldolase, which redirected glyceraldehyde 3-phosphate back into the PPP, thus bypassing gluconeogenesis. This cycling activity may help the cell to overcome NADPH limitation on fructose. The drastically reduced flux arriving at glucose 6-phosphate for fructose-grown *C. glutamicum* might also explain the reduced formation of trehalose on this substrate (Kiefer, P., E. Heinzle and C. Wittmann. 2002. J. Ind. Microbiol. Biotechnol. 28:338-43). Glucose 6-phosphate isomerase operated in opposite directions depending on the carbon source. In glucose-grown net flux was directed from glucose 6-phosphate to fructose 6-phosphate, whereas an inverse net flux was observed on fructose. This underlines the importance of the reversibility of this enzyme for metabolic flexibility in *C. glutamicum*.

C. NADPH Metabolism

The following calculations provide a comparison of the NADPH metabolism of lysine producing *C. glutamicum* on fructose and glucose. The overall supply of NADPH was calculated from the estimated flux through glucose 6-phosphate dehydrogenase, 6-phosphogluconate dehydrogenase, and isocitrate dehydrogenase. On glucose, the PPP enzymes glucose 6-phosphate dehydrogenase (62.0%) and glucose 6-phosphate dehydrogenase (62.0%) supplied the major fraction of NADPH. Isocitrate dehydrogenase (52.9%) contributed only to a minor extent. A completely different contribution of PPP and TCA cycle to NADPH supply was observed on fructose, where isocitrate dehydrogenase (83.3%) was the major source for NADPH. Glucose 6-phosphate dehydrogenase (14.4%) and glucose 6-phosphate dehydrogenase (14.4%) produced much less NADPH on fructose. NADPH is required for growth and formation of lysine. The NADPH requirement for growth was calculated from a stoichiometric demand of 11.51 mmol NAPDH (g biomass)$^{-1}$, which was assumed to be identical for glucose and fructose (Dominguez, H., C. Rollin, A. Guyonvarch, J. L. Guerquin-Kern, M. Cocaien-Bousauet and N. D. Lindley. 1998. Eur. J. Biochem. 254:96-1021 and the experimental biomass yield of the present work (Tab. 1). *C. glutamicum* consumed 62.3% of NADPH for biomass production on glucose, which was much higher as compared to fructose as carbon source (32.8%). The amount of NADPH required for product synthesis was determined from the estimated flux into lysine (Tab. 1) and the corresponding stoichiometric NADPH demand of 4 mol (mol lysine)$^{-1}$. It was 112.4% for lysine production from glucose and 97.6% for lysine production from fructose. The overall NADPH supply on glucose was significantly higher (176.9%) compared to fructose (112.1%), which can be mainly attributed to the increased PPP flux on glucose. The NADPH balance was almost closed on glucose. In contrast a significant apparent deficiency for NADPH of 18.3% was observed on fructose. This raises the question for enzymes catalyzing metabolic reactions that could supply NADPH in addition to the above mentioned enzymes glucose 6-phosphate dehydrogenase, 6-phosphogluconate dehydrogenase and isocitrate dehydrogenase. A likely candidate seems NADPH-dependent malic enzyme. Previously an increased specific activity of this enzyme was detected on fructose-grown *C. melassecola* in comparison to glucose-grown cells (Dominguez, H., C. Rollin, A. Guyonvarch, J. L. Guerquin-Kern, M. Cocaign-Bousquet and N. D. Lindley. 1998. Eur. J. Biochem. 254:96-102). However, the flux through this particular enzyme could not be resolved by the experimental setup in the present work. Assuming malic enzyme as missing NADPH generating enzyme, a flux of 18.3% would be sufficient to supply the apparently missing NADPH. Detailed flux studies of *C. glutamicum* with glucose as carbon source revealed no significant activity of malic enzyme (Petersen, S., A. A. de Graaf, L. Eggeling, M. Möllney, W. Wiechert and H. Sahm. 2000. J. Biol. Chem. 75:35932-35941). The situation on fructose might however be coupled to elevated in vivo activity of this enzyme.

D. NADH Metabolism

On fructose *C. glutamicum* revealed increased activity of NADH forming enzymes. 421.2% NADH were formed on fructose by glyceraldehyde 3-phosphate dehydrogenase, pyruvate dehydrogenase, 2-oxoglutarate dehydrogenase, and malate dehydrogenase. On glucose the NADH production was only 322.4%. Additionally, the anabolic NADH demand was significantly lower on fructose than on glucose. The significantly enhanced NADH production coupled to a reduced metabolic demand could lead to an increased NADH/NAD ratio. For *C. melassecola* it was previously shown that fructose leads to increased NADH/NAD ratio compared to glucose (Dominguez, H., C. Rollin, A. Guyonvarch, J. L. Guerquin-Kern, M. Cocaign-Bousquet and N. D. Lindley. 1998. Eur. J. Biochem. 254:96-102). This raises the question for NADH regenerating mechanisms during lysine production on fructose. Fructose-grown cells exhibited an enhanced secretion of dihydroxyacetone, glycerol, and lactate. The increased formation of dihydroxyacetone and glycerol could be due a higher NADH/NAD ratio. NADH was previously shown to inhibit glyceraldehyde dehydrogenase, so that overflow of dihydroxyacetone and glycerol might be related to a reduction of the flux capacity of this enzyme. The reduction of dihydroxyacetone to glycerol could additionally be favored by the high NADH/NAD ratio and thus contribute to regeneration of excess NADH. The NADH demanding lactate formation from pyruvate could have a similar background as the production of glycerol. In comparison to exponential growth, NADH excess under lysine producing conditions, characterized by relatively high TCA cycle activity and reduced biomass yield, might be even higher.

E. Potential Targets for Optimization of Lysine-Producing *C. glutamicum* on Fructose Based on the obtained flux patterns, several potential targets for the optimization of lysine production by *C. glutamicum* on fructose can be formulated. A central point is the supply of NADPH. Fructose-1,6-bisphosphatase is one target for increasing the supply of NADPH. Deregulation, e.g., amplification of its activity leads to a higher flux through the PPP, resulting in increased NADPH generation and increased lysine yield. An increase of the flux through the PPP via amplification of fructose 1,6-bisphosphatase is also be beneficial for aromatic amino acid production (Ikeda, M. 2003. Adv. Biochem, Eng. Biotechnol. 79: 1-36). The inactivity of fructose 1,6-bisphosphatase during growth on fructose is detrimental from the viewpoint of lysine production but not surprising, because this gluconeogenetic enzyme is not required during growth on sugars and probably suppressed. In prokaryotes, this enzyme is under efficient metabolic control by e.g. fructose 1,6-bisphosphatase, fructose-2,6 bisphosphatase, metal ions and AMP (Skrypal, I. G. and O. V. Iastrebova. 2002. Mikrobiol Z. 64:82-94). It is known that *C. glutamicum* can grow on acetate (Wendisch, V. F., A. A. de Graaf, H. Sahm H. and B. Eikmans. 2000. J. Bacteriol. 182:3088-3096), where this enzyme is essential to maintain gluconeogenesis. Another potential target to increase the flux through the PPP is the PTS for fructose uptake. Modification of flux partitioning between $PTS_{fructose}$ and $PTS_{Mannose}$ could yield a higher proportion of fructose, which enters at the level of fructose 6-phosphate and thus also lead to an increased PPP flux. Additionally amplification of malic enzyme that probably contributes significantly to NADPH supply on fructose could be an interesting target.

Another bottleneck comprises the strong secretion of dihydroxyacetone, glycerol, and lactate. The formation of dihydroxyacetone and glycerol could be blocked by deregulation, e.g., deletion of the corresponding enzymes. The conversion of dihydroxyacetone phosphate to dihydroxyacetone could be catalyzed by a corresponding phosphatase. A dihydroxyacetone phosphatase has however vet not been annotated in *C. glutamicum* (see the National Center for Biotechnology Information (NCBI) Taxonomy website: http://www3.ncbi.nlm.nih.gov/Taxonomy/). This reaction may be also catalyzed by a kinase, e.g., glycerol kinase. Currently two entries in the genome data base of *C. glutamicum* relate to dihydroxyacetone kinase (see the National Center for Biotechnology Information (NCBI) Taxonomy website: http://www3.ncbi.nlm.nih.gov/Taxonomy/).

Lactate secretion can also be avoided by deregulation, e.g., knockout, of lactate dehydrogenase. Since glycerol and lactate formation could be important for NADH regeneration, negative effects on the overall performance of the organism can however not be excluded. In case carbon flux through the lower glycolytic chain is limited by the capacity of glyceraldehyde 3-phosphate dehydrogenase as previously speculated (Dominguez, H., C. Rollin, A. Guyonvarch, J. L. Guerquin-Kern, M. Cocaign-Bousquet and N. D. Lindley. 1998. Eur. J. Biochem. 254:96-102), the suppression of dihydroxyacetone and glycerol production could eventually lead to an activation of fructose-1,6-bisphosphatase and a redirection of carbon flux through the PPP. It should be noticed that dihydroxyacetone is not reutilized during the cultivation of *C. glutamicum* and thus displays wasted carbon with respect to product synthesis, whereas this is not the case for lactate (Cocaign-Bousquet, M. and N. D. Lindley. 1995. Enz. Microbiol. Technol. 17:260-267).

In one embodiment, deregulation of one or more of the above genes in combination is useful in the production of a fine chemical, e.g., lysine.

In addition, sucrose is also useful as carbon source for lysine production by *C. glutamicum*, e.g., used in conjunction with the methods of the invention. Sucrose is the major carbon source in molasses. As shown previously, the fructose unit of sucrose enters glycolysis at the level of fructose 1,6-bisphosphatase (Dominguez, H. and N. D. Lindley. 1996. Appl. Environ. Microbiol. 62:3878-3880). Therefore this part of the sucrose molecule—assuming an inactive fructose 1,6-bisphosphatase—probably does not enter into the PPP, so that NADPH supply in lysine producing strains could be limited.

Example V

Construction of Plasmid pCIS lysC

The first step of strain construction calls for an allelic replacement of the lysC wild-type gene in *C. glutamicum* ATCC 13032. In it, a nucleotide replacement in the lysC gene is carried out, so that, the resulting protein, the amino acid Thr in position 311 is replaced by an Ile. Starting from the chromosomal DNA from ATCC13032 as template for a PCR reaction and using the oligonucleotide primers SEQ ID NO:3 and SEQ ID NO:4, lysC is amplified by use of the Pfu Turbo PCR system (Stratagene USA) in accordance with the instructions of the manufacturer. Chromosomal DNA from *C. glutamicum* ATCC 13032 is prepared according to Tauch et al. (1995) Plasmid 33:168-179 or Eikmanns et al. (1994) Microbiology 140:1817-1828. The amplified fragment is flanked at its 5' end by a SaiI restriction cut and at its 3' end by a MluI restriction cut. Prior to the cloning, the amplified fragment is digested by these two restriction enzymes and purified using the GFX™ PCR DNA and Gel Band Purification Kit (Amersham Pharmacia, Freiburg).

SEQ ID NO: 3
5'-GAGAGAGAGACGCGTCCCAGTGGCTGAGACGCATC-3'

SEQ ID NO: 4
5'-CTCTCTCTGTCGACGAATTCAATCTTACGGCCTG-3'

The obtained polynucleotide is cloned through the SaiI and MM restriction cuts in pCLIK5 MCS with integrated SacB, referred to in the following as pCIS (SEQ ID NO: 5) and transformed in *E. coli* XL-1 blue. A selection for plasmid-carrying cells is accomplished by plating out on kanamycin (20 µg/mL)-containing LB agar (Lennox, 1955, Virology, 1:190). The plasmid is isolated and the expected nucleotide sequence is confirmed by sequencing. The preparation of the plasmid DNA is carried out according to methods of and using materials of the company Quiagen. Sequencing reactions are carried out according to Sanger et al. (1977) Proceedings of the National Academy of Sciences USA 74:5463-5467. The sequencing reactions are separated by means of ABI Prism 377 (PE Applied Biosystems, Weiterstadt) and analyzed. The obtained plasmid pCIS lysC is listed as SEQ ID NO:6.

Example VI

Mutagenesis of the lysC Gene from *C. glutamicum*

The targeted mutagenesis of the lysC gene from *C. glutamicum* is carried out using the QuickChange Kit (Company: Stratagene/USA) in accordance with the instructions of the manufacturer. The mutagenesis is carried out in the plasmid pCIS lysC, SEQ ID NO:6. The following oligonucleotide primers are synthesized for the replacement of thr 311 by 311ile by use of the QuickChange method (Stratagene):

SEQ ID NO: 7
5'-CGGCACCACCGACATCATCTTCACCTGCCCTCGTTCCG-3'

SEQ ID NO: 8
5'-CGGAACGAGGGCAGGTGAAGATGATGTCGGTGGTGCCG-3'

The use of these oligonucleotide primers in the QuickChange reaction leads, in the lysC gene (SEQ ID NO:9), to the replacement of the nucleotide in position 932 (from C to T). The resulting amino acid replacement Thr311Ile in the lysC gene is confirmed, after transformation in *E. coli* XL1-blue and plasmid preparation, by [a] sequencing reaction. The plasmid is given the designation pCIS lysC thr311 ile and is listed as SEQ ID NO:10.

The plasmid pCIS lysC thr311ile is transformed in *C. glutamicum* ATCC13032 by means of electroporation, as described in Liebl, et al. (1989) FEMS Microbiology Letters 53:299-303. Modifications of the protocol are described in DE 10046870. The chromosomal arrangement of the lysC locus of individual transformants is checked using standard methods by Southern blot and hybridization, as described in Sambrook et al. (1989), Molecular Cloning, A Laboratory Manual, Cold Spring Harbor. It is thereby established that the transformants involved are those that have integrated the transformed plasmid by homologous recombination at the lysC locus. After growth of such colonies overnight in media containing no antibiotic, the cells are plated out on a saccharose CM agar medium (10% saccharose) and incubated at 30° C. for 24 hours.

Because the sacB gene contained in the vector pCIS lysC thr311ile converts saccharose into a toxic product, only those colonies can grow that have deleted the sacB gene by a second homologous recombination step between the wild-type lysC gene and the mutated gene lysC thr311ile. During the homologous recombination, either the wild-type gene or the mutated gene together with the sacB gene can be deleted. If the sacB gene together with the wild-type gene is removed, a mutated transformant results.

Growing colonies are picked and examined for a kanamycin-sensitive phenotype. Clones with deleted SacB gene must simultaneously show kanamycin-sensitive growth behavior. Such kanamycin-sensitive clones are investigated in a shaking flask for their lysine productivity (see Example 6). For comparison, the non-treated *C. glutamicum* ATCC13032 is taken. Clones with an elevated lysine production in comparison to the control are selected, chromosomal DNA are recovered, and the corresponding region of the lysC gene is amplified by a PCR reaction and sequenced. One such clone with the property of elevated lysine synthesis and detected mutation in lysC at position 932 is designated as ATCC13032 lysCfbr.

Example VII

Preparation of the Plasmid PK19 MOB SacB Peftu Fructose-1,6 Bisphosphatase

Chromosomal DNA from *C. glutamicum* ATCC 13032 is prepared according to Tauch et al. (1995) Plasmid 33:168-179 or Eikmanns et al. (1994) Microbiology 140:1817-1828.

PCR 1: With the oligonucleotide primers SEQ ID NO 11 and SEQ ID NO 12, the chromosomal DNA as template, and Pfu Turbo polymerase (Company: Stratagene), a region lying upstream of the start codon of the elongation factor TU is amplified by use of the polymerase chain reaction (PCR) according to standard methods, as described in Innis et al. (1990) PCR Protocols. A Guide to Methods and Applications, Academic Press.

```
5'-TGGCCGTTACCCTGCGAATG-3'                SEQ ID NO 11
and

5'-TGTATGTCCTCCTGGACTTC-3'                SEQ ID NO 12
```

The obtained DNA fragment of approximately 200 bp size is purified using the GFX™ PCR DNA and Gel Band Purification Kit (Amersham Pharmacia, Freiburg) in accordance with the instructions of the manufacturer.

PCR 2: With the oligonucleotide primers SEQ ID NO 13 and SEQ ID NO 14, the chromosomal DNA as template, and Pfu Turbo polymerase (Company: Stratagene), the 5' region of the gene for fructose-1,6-bisphosphatase is amplified by use of the polymerase chain reaction (PCR) according to standard methods, as described in Innis et al. (1990) PCR Protocols. A Guide to Methods and Applications, Academic Press.

```
                                          SEQ ID NO 13
5'-GAAGTCCAGGAGGACATACAATGAACCTAAAGAACCCCGA-3'
and

SEQ ID NO 14
5'-ATCTACGTCGACCCAGGATGCCCTGGATTTC-3'
```

The obtained DNA fragment of approximately 740 bp size is purified using the GFX™ PCR DNA and Gel Band Purification Kit (Amersham Pharmacia, Freiburg) in accordance with the instructions of the manufacturer.

PCR 3: With the oligonucleotide primers SEQ ID NO 15 and SEQ ID NO 16, the chromosomal DNA as template, and Pfu Turbo polymerase (Company: Stratagene), a region lying upstream of the start codon of fructose-1,6-bisphosphatase is amplified by use of the polymerase chain reaction (PCR) according to standard methods, as described in Innis et al. (1990) PCR Protocols. A Guide to Methods and Applications, Academic Press.

```
                                          SEQ ID NO 15
5'-TATCAACGCGTTCTTCATCGGTAGCAGCACC-3'
and

SEQ ID NO 16
5'-CATTCGCAGGGTAACGGCCACTGAAGGGCCTCCTGGG-3'
```

The obtained DNA fragment of approximately 720 bp size is purified using the GFX™ PCR DNA and Gel Band Purification Kit (Amersham Pharmacia, Freiburg) in accordance with the instructions of the manufacturer.

PCR 4: With the oligonucleotide primers SEQ TD NO 17 and SEQ ID NO 14, the PCR products from PCR 1 and 2 as template, and Pfu Turbo polymerase (Company: Stratagene), a fusion PCR is carried out by use of the polymerase chain reaction (PCR) according to standard methods, as described in Innis et al. (1990) PCR Protocols. A Guide to Methods and Applications, Academic Press.

The obtained DNA fragment of approximately 920 bp size is purified using the GFX™ PCR DNA and Gel Band Purification Kit (Amersham Pharmacia, Freiburg) in accordance with the instructions of the manufacturer.

PCR 5: With the oligonucleotide primers SEQ ID NO 15 and SEQ ID NO 14, the PCR products from PCR 3 and 4 as template, and Pfu Turbo polymerase (Company: Stratagene), a fusion PCR is carried out by use of the polymerase chain reaction (PCR) according to standard methods, as described in Innis et al. (1990) PCR Protocols. A Guide to Methods and Applications, Academic Press.

The obtained DNA fragment of approximately 1640 bp size is purified using the GFX™ PCR DNA and Gel Band Purification Kit (Amersham Pharmacia, Freiburg) in accordance with the instructions of the manufacturer. Following this, it is cleaved using the restriction enzymes MluI and SaiI (Roche Diagnostics, Mannheim) and the DNA fragment is purified using the GFX™ PCR DNA and Gel Band Purification Kit.

The vector pCIS is cut with the restriction enzymes MluI and SaiI and a fragment of 4.3 kb size is isolated, after electrophoretic separation, by use of the GFX™ PCR DNA and Gel Band Purification Kit.

The vector fragment is ligated together with the PCR fragment from PCR 5 by use of the Rapid DNA Ligation Kit (Roche Diagnostics, Mannheim) in accordance with the instructions of the manufacturer and the ligation batch is transformed in competent *E. coli* XL-1 Blue (Stratagene, La Jolla, USA) according to standard methods, as described in Sambrook et al. (Molecular Cloning. A Laboratory Manual, Cold Spring Harbor, (1989)). A selection for plasmid-carrying cells is accomplished by plating out on kanamycin (20 µg/mL)-containing LB agar (Lennox, 1955, Virology, 1:190).

The preparation of the plasmid DNA is carded out according to methods of and using materials of the company Qiagen. Sequencing reactions are carried out according to Sanger et al. (1977) Proceedings of the National Academy of Sciences USA 74:5463-5467. The sequencing reactions are separated by means of ABI Prism 377 (PE Applied Biosystems, Weiterstadt) and analyzed.

The resulting plasmid pCIS Peftu fructose-1,6-bisphosphatase is listed as SEQ ID NO: 17.

Example VIII

Production of Lysine

The plasmid pCIS Peftu fructose-1,6-bisphosphatase is transformed in *C. glutamicum* ATCC13032 lysCfbr by means of electroporation, as described in Liebl, et al. (1989) FEMS Microbiology Letters 53:299-303. Modifications of the protocol are described in DE 10046870. The chromosomal arrangement of the fructose-1,6-bisphosphatase gene locus of individual transformants is checked using standard methods by Southern blot and hybridization, as described in Sambrook et al. (1989), Molecular Cloning. A Laboratory Manual, Cold Spring Harbor. It is thereby established that the transformants involve those that have integrated the transformed plasmid by homologous recombination at the fructose-1,6-bisphosphatase gene locus. After growth of such colonies overnight in media containing no antibiotic, the cells are plated out on a saccharose CM agar medium (10% saccharose) and incubated at 30° C. for 24 hours.

Because the sacB gene contained in the vector pCIS Peftu fructose-1,6-bisphosphatase converts saccharose into a toxic product, only those colonies can grow that have deleted the sacB gene by a second homologous recombination step between the wild-type fructose-1,6-bisphosphatase gene and the Peftu fructose-1,6-bisphosphatase fusion. During the homologous recombination, either the wild-type gene or the fusion together with the sacB gene can be deleted, if the sacB gene together with the wild-type gene is removed, a mutated transform ant results.

Growing colonies are picked and examined for a kanamycin-sensitive phenotype. Clones with deleted SacB gene must simultaneously show kanamycin-sensitive growth behavior. Whether the desired replacement of the natural promoter by the Peftu promoter had also taken place is checked by means of the polymerase chain reaction (PCR). For this analysis, chromosomal DNA from the starting strain and the resulting clones is isolated. To this end, the respective clones are removed from the agar plate with a toothpick and suspended in 100 µL of H2O and boiled up for 10 min at 95° C. In each case, 10 µL of the resulting solution is used as template in the PCR. Used as primers are oligonucleotides that are homologous to the Peftu promoter and to the fructose-1,6-bisphosphatase gene. The PCR conditions are selected as follows: initial denaturation: 5 min at 95° C.; denaturation 30 see at 95° C.; hybridization 30 sec at 55° C.; amplification 2 min at 72° C.; 30 cycles; end extension 5 min at 72° C. In the batch with the DNA of the starting strain, no PCR product could form owing to the selection of the oligonucleotide. Only for clones that had completed the replacement of the natural promoter by Peftu through the 2nd recombination are a band with a size of 340 bp expected. Overall, of the tested clones, 2 clones are positive. The clones are designated as ATCC13032 lysCfbr Peftu fructose-1,6-bisphosphatase 1 and 2.

In order to investigate the effect of the Peftu fructose-1,6-bisphosphatase construct on the lysine production, the strains ATCC 13032. ATCC 13032 lysCfbr, and ATCC13032 lysCfbr Peftu fructose-1,6-bisphosphatase 1 are cultivated on CM plates (10.0 g/L D-glucose, 2.5 g/L NaCl, 2.0 g/L urea, 10.0 g/L bacto pepton (Difco), 5.0 g/L yeast extract (Difco), 5.0 g/L beef extract (Difco), 22.0 g/L agar (Difco), autoclaved (20 min. 121° C.)) for 2 days at 30° C. Subsequently, the cells are scraped off the plate and resuspended in saline. For the main culture, 10 mL of medium 1 and 0.5 g of autoclaved CaCO3 (Riedel de Haen) are inoculated in a 100 mL Erlenmeyer flask with the cell suspension up to an OD600 of 1.5 and incubated for 39 h on a [shaking incubator] of the type Infors AJ118 (Company: Infors, Bottmingen, Switzerland) at 220 rpm. Subsequently, the concentration of the lysine that separated out in the medium is determined.

| Medium I: | |
|---|---|
| 40 g/L | saccharose |
| 60 g/L | Molasses (calculated with respect to 100% sugar content) |
| 10 g/L | $(NH_4)_2SO_4$ |
| 0.4 g/L | $MgSO_4*7H_2O$ |
| 0.6 g/L | $KH_2PO_4$ |
| 0.3 mg/L | thiamine*HCl |
| 1 mg/L | biotin (from a 1 mg/mL sterile-filtered stock solution that is adjusted with $NH_4OH$ to pH 8.0) |
| 2 mg/L | $FeSO_4$ |
| 2 mg/L | $MnSO_4$ |
| adjusted with $NH_4OH$ to pH 7.8, autoclaved (121° C., 20 min). | |

In addition, vitamin B12 (hydroxycobalamin Sigma Chemicals) from a stock solution (200 µg/mL, sterile-filtered) is added up to a final concentration of 100 µg/L.

The determination of the amino acid concentration is conducted by means of high pressure liquid chromatography according to Agilent on an Agilent 1100 Series LC System HPLC. A precolumn derivatization with ortho-phthalaldehyde permits the quantification of the amino acids that are formed; the separation of the amino acid mixture takes place on a Hypersil AA column (Agilent).

Example IX

Preparation of the Plasmid pCIS Psod Fructose-1,6 Bisphosphatase

Chromosomal DNA from C. glutamicum ATCC 13032 is prepared according to Tauch et al. (1995) Plasmid 33:168-179 or Eikmanns et al. (1994) Microbiology 140:1817-1828.

PCR 1: With the oligonucleotide primers SEQ ID NO 18 and SEQ ID NO 19, the chromosomal DNA as template, and Pfu Turbo polymerase (Company: Stratagene), a region lying upstream of the start codon of the superoxid dismutase is amplified by use of the polymerase chain reaction (PCR) according to standard methods, as described in Innis et al. (1990) PCR Protocols. A Guide to Methods and Applications, Academic Press.

```
5'-tagctgccaattattccggg-3'          SEQ ID NO 18
and

5'-GGGTAAAAAATCCTTTCGTA-3'          SEQ ID NO 19
```

The obtained DNA fragment of approximately 200 bp size is purified using the GFX™ PCR DNA and Gel Band Purification Kit (Amersham Pharmacia, Freiburg) in accordance with the instructions of the manufacturer.

PCR 2: With the oligonucleotide primers SEQ ID NO 20 and SEQ ID NO 21, the chromosomal DNA as template, and Pfu Turbo polymerase (Company: Stratagene), the 5' region of the gene for fructose-1,6-bisphosphatase is amplified by use of the polymerase chain reaction (PCR) according to standard methods, as described in Innis et al. (1990) PCR Protocols. A Guide to Methods and Applications, Academic Press.

```
                                    SEQ ID NO 20
5'-CCCGGAATAATTGGCAGCTACTGAAGGGCCTCCTGGG-3'
and
                                    SEQ ID NO 21
5'-TATCAACGCGTTCTTCATCGGTAGCAGCACC-3'
```

The obtained DNA fragment of approximately 720 bp size is purified using the GFX™ PCR DNA and Gel Band Purification Kit (Amersham Pharmacia, Freiburg) in accordance with the instructions of the manufacturer.

PCR 3: With the oligonucleotide primers SEQ ID NO 22 and SEQ ID NO 23, the chromosomal DNA as template, and Pfu Turbo polymerase (Company: Stratagene), a region lying upstream of the start codon of fructose-1,6-bisphosphatase is amplified by use of the polymerase chain reaction (PCR) according to standard methods, as described in Innis et al. (1990) PCR Protocols. A Guide to Methods and Applications, Academic Press.

```
                                              SEQ ID NO 22
5'-TACGAAAGGATTTTTTACCCATGAACCTAAAGAACCCCGA-3'
and
                                              SEQ ID NO 23
5'-ATCTACGTCGACCCAGGATGCCCTGGATTTC-3'
```

The obtained DNA fragment of approximately 740 bp size is purified using the GFX™ PCR DNA and Gel Band Purification Kit (Amersham Pharmacia, Freiburg) in accordance with the instructions of the manufacturer.

PCR 4: With the oligonucleotide primers SEQ ID NO 18 and SEQ ID NO 23, the PCR products from PCR 1 and 3 as template, and Pfu Turbo polymerase (Company: Stratagene), a fusion PCR is carried out by use of the polymerase chain reaction (PCR) according to standard methods, as described in Innis et al. (1990) PCR Protocols. A Guide to Methods and Applications, Academic Press.

The obtained DNA fragment of approximately 930 bp size is purified using the GFX™ PCR DNA and Gel Band Purification Kit (Amersham. Pharmacia, Freiburg) in accordance with the instructions of the manufacturer.

PCR 5: With the oligonucleotide primers SEQ ID NO 21 and SEQ ID NO 23, the PCR products from PCR 2 and 4 as template, and Pfu Turbo polymerase (Company: Stratagene), a fusion PCR is carried out by use of the polymerase chain reaction (PCR) according to standard methods, as described in Innis et al. (1990) PCR Protocols. A Guide to Methods and Applications, Academic Press.

The obtained DNA fragment of approximately 1650 bp size is purified using the GFX™ PCR DNA and Gel Band Purification Kit (Amersham Pharmacia, Freiburg) in accordance with the instructions of the manufacturer. Following this, it is cleaved using the restriction enzymes MluI and SaiI (Roche Diagnostics, Mannheim) and the DNA fragment is purified using the GFX™ PCR DNA and Gel Band Purification Kit.

The vector pCIS is cut with the restriction enzymes MluI and SaiI and a fragment of 4.3 kb size is isolated, after electrophoretic separation, by use of the GFX™ PCR DNA and Gel Band Purification Kit.

The vector fragment is ligated together with the PCR fragment from PCR 5 by use of the Rapid DNA Ligation Kit (Roche Diagnostics, Mannheim) in accordance with the instructions of the manufacturer and the ligation batch is transformed in competent E. coli XL-1 Blue (Stratagene, La Jolla, USA) according to standard methods, as described in Sambrook et al. (Molecular Cloning. A Laboratory Manual, Cold Spring Harbor, (1989)). A selection for plasmid-carrying cells is accomplished by plating out on kanamycin (20 µg/mL)-containing LB agar (Lennox, 1955, Virology, 1:190).

The preparation of the plasmid DNA is carried out according to methods of and using materials of the company Qiagen. Sequencing reactions are carried out according to Sanger et al. (1977) Proceedings of the National Academy of Sciences USA 74:5463-5467. The sequencing reactions are separated by means of ABI Prism 377 (PE Applied Biosystems, Weiterstadt) and analyzed.

The resulting plasmid pCIS Psod fructose-1,6-bisphosphatase is listed as SEQ ID NO: 24.

Example X

Production of Lysine

The plasmid pCIS Psod fructose-1,6-bisphosphatase is transformed in C. glutamicum ATCC 13032 lysCfbr by means of electroporation, as described in Liebl, et al. (1989) FEMS Microbiology Letters 53:299-303. Modifications of the protocol are described in DE 10046870. The chromosomal arrangement of the fructose-1,6-bisphosphatase gene locus of individual transformants is checked using standard methods by Southern blot and hybridization, as described in Sambrook et al. (1989), Molecular Cloning. A Laboratory Manual, Cold Spring Harbor. It is thereby established that the transformants involve those that have integrated the transformed plasmid by homologous recombination at the fructose-1,6-bisphosphatase gene locus. After growth of such colonies overnight in media containing no antibiotic, the cells are plated out on a saccharose CM agar medium (10% saccharose) and Incubated at 30° C. for 24 hours.

Because the sacB gene contained in the vector pCIS Psod fructose-1,6-bisphosphatase converts saccharose into a toxic product, only those colonies can grow that have deleted the sacB gene by a second homologous recombination step between the wild-type fructose-1,6-bisphosphatase gene and the Psod fructose-1,6-bisphosphatase fusion. During the homologous recombination, either the wild-type gene or the fusion together with the sacB gene can be deleted. If the sacB gene together with the wild-type gene is removed, a mutated transformant results.

Growing colonies are picked and examined for a kanamycin-sensitive phenotype. Clones with deleted SacB gene must simultaneously show kanamycin-sensitive growth behavior. Whether the desired replacement of the natural promoter by the Psod promoter had also taken place is checked by means of the polymerase chain reaction (PCR). For this analysis, chromosomal DNA from the starting strain and the resulting clones is isolated. To this end, the respective clones are removed from she agar plate with a toothpick and suspended in 100 µL of H2O and boiled up for 10 min at 95° C. In each case, 10 µL of the resulting solution is used as template in the PCR. Used as primers are oligonucleotides that are homologous to the Psod promoter and to the fructose-1,6-bisphosphatase gene. The PCR conditions are selected as follows: initial denaturation: 5 min at 95° C.; denaturation 30 sec at 95° C.; hybridization 30 sec at 55° C.; amplification 2 min at 72° C.; 30 cycles; end extension 5 min at 72° C. In the batch with the DNA of the starting strain, no PCR product could form owing to the selection of the oligonucleotide. Only three clones that had completed the replacement of the natural promoter by Psod through the 2nd recombination are a band with a size of 350 bp expected. Overall, of the tested clones, 3 clones are positive. The clones are designated as ATCC13032 lysCfbr Psod fructose-1,6-bisphosphatase 1, 2 and 3.

In order to investigate the effect of the Psod fructose-1,6-bisphosphatase construct on the lysine production, the strains ATCC13032, ATCC13032 lysCfbr, and ATCC13032 lysCfbr Psod fructose-1,6-bisphosphatase 1 are cultivated on CM plates (10.0 g/L D-glucose, 2.5 g/L NaCl, 2.0 g/L urea, 10.0 g/L bacto pepton (Difco), 5.0 g/L yeast extract (Difco), 5.0 g/L beef extract (Difco), 22.0 g/L agar (Difco), autoclaved (20 min. 121° C.)) for 2 days at 30° C. Subsequently, the cells are scraped off the plate and resuspended in saline. For the main culture, 10 mL of medium 1 and 0.5 g of autoclaved CaCO3 (Riedel de Haen) are inoculated in a 100 mL Erlenmeyer flask with the cell suspension up to an OD600 of 1.5 and incubated for 39 h on a shaking incubator of the type Infors AJ118 (Company: Infors, Bottmingen, Switzerland) at 220 rpm. Subsequently, the concentration of the lysine that separated out in the medium is determined.

Medium I:

| | |
|---|---|
| 40 g/L | saccharose |
| 60 g/L | Molasses (calculated with respect to 100% sugar content) |
| 10 g/L | $(NH_4)_2SO_4$ |
| 0.4 g/L | $MgSO_4*7H_2O$ |
| 0.6 g/L | $KH_2PO_4$ |
| 0.3 mg/L | thiamine*HCl |
| 1 mg/L | biotin (from a 1 mg/mL sterile-filtered stock solution that is adjusted with $NH_4OH$ to pH 8.0) |

Medium I:

| | |
|---|---|
| 2 mg/L | $FeSO_4$ |
| 2 mg/L | $MnSO_4$ |
| adjusted with $NH_4OH$ to pH 7.8, autoclaved (121° C., 20 min). | |

In addition, vitamin B12 (hydroxycobalamin Sigma Chemicals) from a stock solution (200 µg/mL, sterile-filtered) is added up to a final concentration of 100 µg/L.

The determination of the amino acid concentration is conducted by means of high pressure liquid chromatography according to Agilent on an Agilent 1100 Series LC System HPLC. A precolumn derivatization with ortho-phthalaldehyde permits the quantification of the amino acids that are formed; the separation of the amino acid mixture takes place on a Hypersil AA column (Agilent).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing an L-amino acid comprising:
   a) culturing a microorganism in which fructose-1,6-bisphosphatase is overexpressed for a sufficient time to produce at least 15 to 20 g/L of the L-amino acid;
   b) accumulating the L-amino acid in the medium or in the cells of the microorganism; and
   c) recovering the L-amino acid, thereby producing the L-amino acid.

2. A method for producing an L-amino acid comprising culturing a microorganism in which at least fructose-1,6-bisphosphatase expression is increased under conditions and for a sufficient time to produce at least 15 to 20 g/L of the L-amino acid and recovering the L-amino acid.

3. The method of claim 2, wherein one or more additional gene is overexpressed.

4. The method of claim 3, wherein the one or more additional overexpressed gene encodes a protein selected from the group consisting of a feed-back resistant aspartokinase, a dihydrodipicolinate synthase, an aspartate semialdehyde dehydrogenase, a dihydrodipicolinate reductase, a diaminopimelate dehydrogenase, a diaminopimelate epimerase, a lysine exporter, a pyruvate carboxylase, a glucose-6-phosphate dehydrogenase, a phosphoenolpyruvate carboxylase, a glyceraldedyde-3-phosphate dehydrogenase, a resuscitation promoting factor protein precursor, a transketolase, a transaldolase, a menaquinine oxidoreductase, a triosephosphate isomerase, a 3-phosphoglycerate kinase, and an RNA-polymerase sigma factor sigC.

5. The method of claim 4, wherein the protein has increased activity.

6. The method of claim 2, wherein the expression of one or more additional gene is attenuated, decreased or repressed and the one or more additional gene encodes a protein selected from the group consisting of a phosphoenolpyruvate carboxykinase, a malic enzyme, a glycogen synthase, a glucose-6-phosphate isomerase, an ATP dependent RNA helicase, an o-succinylbenzoic acid-CoA ligase, a citrate lyase beta chain, a transcriptional regulator, a pyruvate dehydrogenase, a resuscitation promoting factor protein precursor, and a Succinyl-CoA-Synthetase.

7. The method of claim 2, wherein the microorganism is a Gram positive microorganism.

8. The method of claim 2, wherein the microorganism belongs to the genus *Corynebacterium*.

9. The method of claim 8, wherein the microorganism is *Corynebacterium glutamicum*.

10. The method of claim 2, wherein fructose or sucrose is used as a carbon source.

11. The method of claim 2, wherein fructose is used as a carbon source.

12. The method of claim 2, wherein fructose-1,6-bisphosphatase comprises the nucleotide sequence of SEQ ID NO:1.

13. The method of claim 2, wherein fructose-1,6-bisphosphatase encodes a polypeptide comprising the amino acid sequence of SEQ ID NO:2.

* * * * *